United States Patent [19]
Fischer et al.

[11] Patent Number: 5,186,737
[45] Date of Patent: Feb. 16, 1993

[54] PESTICIDAL 3-ARYL-PYRROLIDINE-2,4-DIONES

[75] Inventors: Reiner Fischer, Monheim; Bernd Baasner, Bergisch-Gladbach; Hermann Hageman, Leverkusen; Andreas Krebs, Odehthal-Holz; Albrecht Marhold; Hans-Joachim Santel, both of Leverkusen; Robert R. Schmidt; Klaus Lürssen, both of Bergisch-Gladbach, all of Fed. Rep. of Germany; Benedikt Becker, Bolzano, Italy; Klaus Schaller, Wuppertal; Harry Strang, Duesseldorf, both of Fed. Rep. of Germany

[73] Assignee: Bayer Aktiengesellschaft, Leverkusen, Fed. Rep. of Germany

[21] Appl. No.: 678,479

[22] Filed: Apr. 1, 1991

Related U.S. Application Data

[62] Division of Ser. No. 460,208, Jan. 2, 1990, Pat. No. 5,045,560.

[30] Foreign Application Priority Data

Jan. 7, 1989 [DE] Fed. Rep. of Germany ....... 3900301
Aug. 18, 1989 [DE] Fed. Rep. of Germany ....... 3927222

[51] Int. Cl.$^5$ .............................. D01N 43/36
[52] U.S. Cl. ................... 504/283; 548/544; 504/252; 504/266; 504/280; 504/239; 504/166
[58] Field of Search ............................ 71/95

[56] References Cited

U.S. PATENT DOCUMENTS 3,401,176  9/1968  Hottman ............................. 598/544

FOREIGN PATENT DOCUMENTS 0262399  4/1988  European Pat. Off. .
0377893  7/1990  European Pat. Off. ............ 548/544

OTHER PUBLICATIONS

Schmierer et al, "Cyclisierung von N-Acylalanin- und N-Acylglycinestern", Liebigs Ann. Chem. 1985, pp. 1095–1098.

*Primary Examiner*—David B. Springer
*Attorney, Agent, or Firm*—Sprung Horn Kramer & Woods

[57] ABSTRACT

Insecticidal, acaricidal, herbicidal and antimycotic 3-aryl-pyrrolidine-2,4-diones of the formula

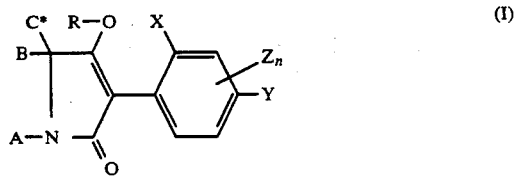

in which
X represents alkyl, halogen or alkoxy,
Y represents hydrogen, alkyl, halogen, alkoxy or halogenoalkyl,
Z represents alkyl, halogen or alkoxy,
n represents a number from 0–3,
R represents hydrogen or represents the groups —CO—R$^1$ or —CO—O—R$^2$,
  in which
  R$^1$ represents alkyl, alkenyl, alkoxyalkyl, alkylthioalkyl, polyalkoxyalkyl or cycloalkyl which can be interrupted by hetero atoms, each of which radicals is optionally substituted by halogen, or represents optionally substituted phenyl, optionally substituted phenylalkyl, substituted hetaryl, substituted phenoxyalkyl or substituted hetaryloxyalkyl, or represents optionally substituted phenyl, optionally substituted phenylalkyl, substituted hetaryl, substituted phenoxyalkyl and substituted hetaryloxyalkyl, and
  R$^2$ represents alkyl, alkenyl, alkoxyalkyl, polyalkoxyalkyl or optionally substituted phenyl or cycloalkyl, each of which radicals is optionally substituted by halogen,
A represents alkyl, alkenyl, alkinyl, alkoxyalkyl, polyalkoxyalkyl, alkylthioalkyl, or cycloalkyl which is optionally interrupted by a hetero atom, each of which radicals is optionally subsituted by halogen, or represents arylalkyl which is optionally substituted by halogen, alkyl, halogenoalkyl, alkoxy or nitro,
B and C* independently of one another represent hydrogen, alkyl or alkoxyalkyl.

12 Claims, No Drawings

PESTICIDAL 3-ARYL-PYRROLIDINE-2,4-DIONES

This is a division of application Ser. No. 460,208, filed Jan. 2, 1990, now U.S. Pat. No. 5,045,560.

The invention relates to new 3-aryl-pyrrolidine-2,4-dione derivatives, to several processes for their preparation, and to their use as insecticides, acaricides and herbicides.

Pharmaceutical properties have previously been described of 3-acyl-pyrrolidine-2,4-diones (S. Suzuki et al. Chem. Pharm. Bull. 15 1120 (1967)). Furthermore, N-phenylpyrrolidine-2,4-diones were synthesized by R. Schmierer and H. Mildenberger Liebigs Ann. Chem. 1985 1095. A biological activity of these compounds has not been described.

Compounds of a similar structure (3-aryl-pyrrolidine-2,4-diones) are disclosed in EP-A 0,262,399, but a herbicidal, insecticidal or acaricidal action is not known in these cases.

New 3-aryl-pyrrolidine-2,4-dione derivatives have now been found, which are represented by the formula (I)

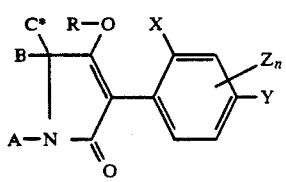

in which
X represents alkyl, halogen and alkoxy,
Y represents hydrogen, alkyl, halogen, alkoxy and halogenoalkyl,
Z represents alkyl, halogen and alkoxy,
n represents a number from 0-3,
R represents hydrogen or represents the groups $-CO-R^1$, $-CO-O-R^2$
in which
R$^1$ represents alkyl, alkenyl, alkoxyalkyl, alkylthioalkyl, polyalkoxyalkyl and cycloalkyl which can be interrupted by hetero atoms, each of which radicals is optionally substituted by halogen, or represents optionally substituted phenyl, optionally substituted phenylalkyl, substituted hetaryl, substituted phenoxyalkyl and substituted hetaryloxyalkyl, and
R$^2$ represents alkyl, alkenyl, alkoxyalkyl, polyalkoxyalkyl and optionally substituted phenyl or cycloalkyl, each of which radicals is optionally substituted by halogen,
A represents alkyl, alkenyl, alkinyl, alkoxyalkyl, polyalkoxyalkyl, alkylthioalkyl, or cycloalkyl which is optionally interrupted by hetero atoms, each of which radicals is optionally substituted by halogen, or represents arylalkyl which is optionally substituted by halogen, alkyl, halogenoalkyl, alkoxy or nitro,
B and C* independently of one another represent hydrogen, alkyl or alkoxyalkyl,
and the enantiomerically pure forms of compounds of the formula (I).

The following sub-groups may be as defined below:
(Ia): Compounds of the formula (I) where R is hydrogen,
(Ib): Compounds of the formula (I) where R is COR$^1$,
(Ic): Compounds of the formula (I) where R is COOR$^2$.

Furthermore, it has been found that 3-arylpyrrolidine-2,4-diones or the enols thereof, of the formula (Ia)

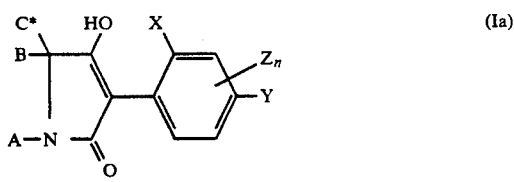

in which A, B, C*, X, Y, Z and n have the abovementioned meanings, are obtained when
(A)
N-acylamino acid esters of the formula (II)

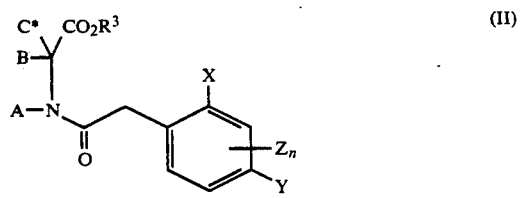

in which A, B, C*, X, Y, Z and n have the abovementioned meanings and R$^3$ represents alkyl, are subjected to intramolecular condensation in the presence of a diluent and in the presence of a base.
(B)
Moreover, it has been found that compounds of the formula (Ib)

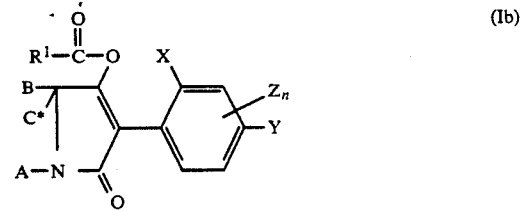

in which A, B, C*, X, Y, Z, R$^1$ and n have the abovementioned meanings, are obtained when compounds of the formula (Ia)

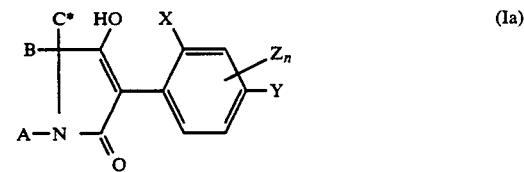

in which A, B, C*, X, Y, Z and n have the abovementioned meanings, are reacted
a) with acid halides of the general formula (III)

in which R$^1$ has the abovementioned meaning and Hal represents halogen, in particular chlorine and bromine, if appropriate in the presence of a diluent and if appropriate in the presence of an acid-binding agent, or b) with carboxylic anhydrides of the general formula (IV)

$$R^1\text{-CO-O-CO-}R^1 \qquad \text{(IV)}$$

in which $R^1$ has the abovementioned meaning, if appropriate in the presence of a diluent and if appropriate in the presence of an acid-binding agent.

(C)

Furthermore, it has been found that compounds of the formula (Ic)

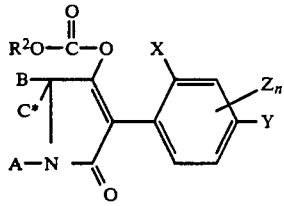

in which A, B, C*, X, Y, Z, $R^2$ and n have the abovementioned meanings, are obtained when compounds of the formula (Ia)

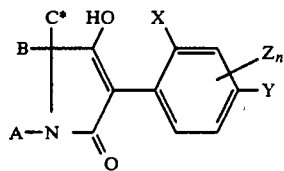

in which A, B, C*, X, Y, Z and n have the abovementioned meanings, are reacted with chloroformic acid esters of the general formula (V)

$$R^2\text{-O-CO-Cl} \qquad \text{(V)}$$

in which $R^2$ has the abovementioned meaning, if appropriate in the presence of a diluent and if appropriate in the presence of an acid-binding agent.

Surprisingly, it has been found that the new 3-aryl-pyrrolidine-2,4-dione derivatives of the formula (I) are distinguished by outstanding insecticidal, acaricidal, herbicidal and antimycotic actions.

Preferred 3-aryl-pyrrolidine-2,4-dione derivatives of the formula (I) are those in which X represents $C_1$-$C_6$-alkyl, halogen and $C_1$-$C_6$-alkoxy,
Y represents hydrogen, $C_1$-$C_6$-alkyl, halogen, $C_1$-$C_6$-alkoxy, and $C_1$-$C_3$-halogenoalkyl,
Z represents $C_1$-$C_6$-alkyl, halogen and $C_1$-$C_6$-alkoxy,
n represents a number from 0–3,
R represents hydrogen (Ia) or represents the groups of the formula $$-\text{CO}-R^1 \text{ (Ib) or } -\text{CO}-\text{O}-R^2 \text{ (Ic)}$$

in which
$R^1$ represents $C_1$-$C_{20}$-alkyl, $C_2$-$C_{20}$-alkenyl, $C_1$-$C_8$-alkoxy-$C_2$-$C_8$-alkyl, $C_1$-$C_8$-alkylthio-$C_2$-$C_8$-alkyl, $C_1$-$C_8$-polyalkoxy-$C_2$-$C_8$-alkyl and cycloalkyl which has 3–8 ring atoms and which can be interrupted by oxygen and/or sulphur, each of which radicals is optionally substituted by halogen, or represents phenyl which is optionally substituted by halogen, nitro, $C_1$-$C_6$-alkyl, $C_1$-$C_6$-alkoxy, $C_1$-$C_6$-halogenoalkyl or $C_1$-$C_6$-halogenoalkoxy; or represents phenyl-$C_1$-$C_6$-alkyl which is optionally substituted by halogen, $C_1$-$C_6$-alkyl, $C_1$-$C_6$-alkoxy, $C_1$-$C_6$-halogenoalkyl or $C_1$-$C_6$-halogenoalkoxy, or represents hetaryl which is optionally substituted by halogen and $C_1$-$C_6$-alkyl, or represents phenoxy-$C_1$-$C_6$-alkyl which is optionally substituted by halogen and $C_1$-$C_6$-alkyl, or represents hetaryloxy-$C_1$-$C_6$-alkyl which is optionally substituted by halogen, amino and $C_1$-$C_6$-alkyl,
$R^2$ represents $C_1$-$C_{20}$-alkyl, $C_2$-$C_{20}$-alkenyl, $C_1$-$C_8$-alkoxy-$C_2$-$C_8$-alkyl and $C_1$-$C_8$-polyalkoxy-$C_2$-$C_8$-alkyl, each of which radicals is optionally substituted by halogen, or represents phenyl or cycloalkyl which has 3–8 ring atoms, each of which radicals is optionally substituted by halogen nitro, $C_1$-$C_6$-alkyl, $C_1$-$C_6$-alkoxy or $C_1$-$C_6$-halogenoalkyl,
A represents straight-chain or branched $C_1$-$C_{12}$-alkyl, $C_3$-$C_8$-alkenyl, $C_3$-$C_8$-alkinyl, $C_1$-$C_{10}$-alkoxy-$C_2$-$C_8$-alkyl, $C_1$-$C_8$-polyalkoxy-$C_2$-$C_8$-alkyl, $C_1$-$C_{10}$-alkylthio-$C_2$-$C_8$-alkyl or cycloalkyl which has 3–8 ring atoms and which can be interrupted by oxygen and/or sulphur, each of which radicals is optionally substituted by halogen, or represents aryl-$C_1$-$C_6$-alkyl which is optionally substituted by halogen, $C_1$-$C_6$-alkyl-$C_1$-$C_6$-haloalkyl, $C_1$-$C_6$-alkoxy or nitro,
B and C* independently of one another represent hydrogen, straight-chain or branched $C_1$-$C_{12}$-alkyl or $C_1$-$C_8$-alkoxyalkyl,
and the enantiomerically pure forms of compounds of the formula (I).

Particularly preferred compounds of the formula (I) are those in which

X represents $C_1$-$C_4$-alkyl, halogen and $C_1$-$C_4$-alkoxy,
Y represents hydrogen, $C_1$-$C_6$-alkyl, halogen, $C_1$-$C_4$-alkoxy and $C_1$-$C_2$-halogenoalkyl,
Z represents $C_1$-$C_4$-alkyl, halogen and $C_1$-$C_4$-alkoxy,
n represents a number from 0–3,
R represents hydrogen (Ia) or represents the groups of the formula $$-\text{CO}-R^1 \text{ (Ib) or } -\text{CO}-\text{O}-R^2 \text{ (Ic)}$$

in which
$R^1$ represents $C_1$-$C_{16}$-alkyl, $C_2$-$C_{16}$-alkenyl, $C_1$-$C_6$-alkoxy-$C_2$-$C_6$-alkyl, $C_1$-$C_6$-alkylthio-$C_2$-$C_6$-alkyl, $C_1$-$C_6$-polyalkoxy-$C_2$-$C_6$-alkyl and cycloalkyl which has 3–7 ring atoms and which can be interrupted by 1–2 oxygen and/or sulphur atoms, each of which radicals is optionally substituted by halogen, or represents phenyl which is optionally substituted by halogen, nitro, $C_1$-$C_4$-alkyl, $C_1$-$C_4$-alkoxy, $C_1$-$C_3$-halogenoalkyl or $C_1$-$C_3$-halogenoalkoxy, or represents phenyl-$C_1$-$C_4$-alkyl which is optionally substituted by halogen, $C_1$-$C_4$-alkyl, $C_1$-$C_4$-alkoxy, $C_1$-$C_3$-halogenoalkyl or $C_1$-$C_3$-halogenoalkoxy, or represents hetaryl which is optionally substituted by halogen and $C_1$-$C_6$-alkyl, or represents phenoxy-$C_1$-$C_5$-alkyl which is optionally substituted by halogen and $C_1$-$C_4$-alkyl, or represents hetaryloxy-$C_1$-$C_5$-alkyl which is optionally substituted by halogen, amino and $C_1$-$C_4$-alkyl,
$R^2$ represents $C_1$-$C_{16}$-alkyl, $C_2$-$C_{16}$-alkenyl, $C_1$-$C_{16}$-alkoxy-$C_2$-$C_6$-alkyl and $C_1$-$C_6$-polyalkoxy-$C_2$-$C_6$-alkyl, each of which radicals is optionally substituted by halogen, or represents phenyl or cycloalkyl which has 3-7 ring atoms each of which radicals is optionally substituted by halogen, nitro, $C_1$-$C_4$-alkyl, $C_1$-$C_3$-alkoxy or $C_1$-$C_3$-halogenoalkyl, A represents straight-chain or branched $C_1$-$C_{10}$-alkyl, $C_3$-$C_6$-alkenyl, $C_3$-$C_6$-alkinyl, $C_1$-$C_8$-alkoxy-$C_2$-$C_6$-alkyl, $C_1$-$C_6$-polyalkoxy-$C_2$-$C_6$-alkyl, $C_1$-$C_8$-alkylthio-$C_2$-$C_6$-alkyl or cycloalkyl which has 3-7 ring atoms and which can be interrupted by 1-2 oxygen and/or sulphur atoms, each of which radicals is optionally substituted by halogen, or represents aryl-$C_1$-$C_4$-alkyl which is optionally substituted by halogen, $C_1$-$C_4$-alkyl, $C_1$-$C_4$-haloalkyl-$C_1$-$C_4$-alkoxy or nitro, B and C* independently of one another represent hydrogen, straight-chain or branched $C_1$-$C_{10}$-alkyl and $C_1$-$C_6$-alkoxyalkyl, and the enantiomerically pure forms of compounds of the formula (I).

Very particularly preferred compounds of the formula (I) are those in which

X represents methyl, ethyl, propyl, i-propyl, fluorine, chlorine, bromine, methoxy and ethoxy, Y represents hydrogen, methyl, ethyl, propyl, i-propyl, butyl, i-butyl, tert.-butyl, fluorine, chlorine, bromine, methoxy, ethoxy and trifluoromethyl, Z represents methyl, ethyl, i-propyl, butyl, i-butyl, tert.-butyl, fluorine, chlorine, bromine, methoxy and ethoxy, n represents a number from 0-3, R represents hydrogen (Ia) or represents the groups of the formula —CO—$R^1$ (Ib) or —CO—O—$R^2$ (Ic)

in which $R^1$ represents $C_1$-$C_{14}$-alkyl, $C_2$-$C_{14}$-alkenyl, $C_1$-$C_4$-alkoxy-$C_2$-$C_6$-alkyl, $C_1$-$C_4$-alkylthio-$C_2$-$C_6$-alkyl, $C_1$-$C_4$-polyalkoxyl-$C_2$-$C_4$-alkyl and cycloalkyl which has 3-6 ring atoms and which can be interrupted by 1-2 oxygen and/or sulphur atoms, each of which radicals is optionally substituted by fluorine or chlorine, or represents phenyl which is optionally substituted by fluorine, chlorine, bromine, methyl, ethyl, propyl, i-propyl, methoxy, ethoxy, trifluoromethyl, trifluoromethoxy or nitro, or represents phenyl-$C_1$-$C_3$-alkyl which is optionally substituted by fluorine, chlorine, bromine, methyl, ethyl, propyl, i-propyl, methoxy, ethoxy, trifluoromethyl or trifluoromethoxy, or represents pyridyl, pyrimidyl, thiazolyl and pyrazolyl, each of which radicals is optionally substituted by fluorine, chlorine, bromine, methyl or ethyl, or represents phenoxy-$C_1$-$C_4$-alkyl which is optionally substituted by fluorine, chlorine, methyl or ethyl, or represents pyridyloxy-$C_1$-$C_4$-alkyl, pyrimidyloxy-$C_1$-$C_4$-alkyl and thiazolyloxy-$C_1$-$C_4$-alkyl, each of which radicals is optionally substituted by fluorine, chlorine, amino, methyl or ethyl, $R^2$ represents $C_1$-$C_{14}$-alkyl, $C_2$-$C_{14}$-alkenyl, $C_1$-$C_4$-alkoxy-$C_2$-$C_6$-alkyl and $C_1$-$C_4$-polyalkoxy-$C_2$-$C_6$-alkyl, each of which radicals is optionally substituted by fluorine or chlorine, or represents phenyl or cycloalkyl which has 3-6 ring atoms, each of which radicals is optionally substituted by fluorine, chlorine, nitro, methyl, ethyl, propyl, i-propyl, methoxy, ethoxy or trifluoromethyl, A represents straight-chain or branched $C_1$-$C_4$-alkyl, $C_3$-$C_4$-alkenyl, $C_3$-$C_4$-alkinyl, $C_1$-$C_6$-alkoxy-$C_2$-$C_4$-alkyl, $C_1$-$C_4$-polyalkoxy-$C_2$-$C_4$-alkyl, $C_1$-$C_6$-alkylthio-$C_2$-$C_4$-alkyl and cycloalkyl which has 3-6 ring atoms and which can be interrupted by 1-2 oxygen and/or sulphur atoms, each of which radicals is optionally substituted by halogen, or represents aryl-$C_1$-$C_3$-alkyl which is optionally substituted by fluorine, chlorine, bromine, methyl, ethyl, propyl, isopropyl, methoxy, ethoxy, trifluoromethyl or nitro, B and C* independently of one another represent hydrogen, straight-chain or branched $C_1$-$C_8$-alkyl and $C_1$-$C_4$-alkoxyalkyl, and the enantiomerically pure forms of compounds of the formula I.

If, in accordance with process (A), N-2,6-dichlorophenyl-acetyl-N-methyl-alanine ethyl ester is used, the procedure of the process according to the invention can be represented by the following equation:

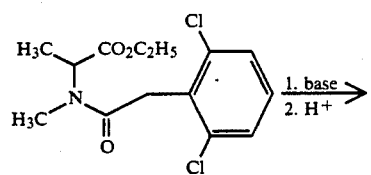

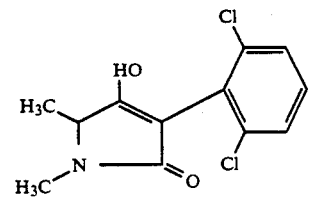

If, in accordance with process (B) (variant a), 3-(2,4,6-trimethylphenyl)-1-isopropyl-pyrrolidin-2,4-dione and pivaloyl chloride are used as the starting substances, the course of the process according to the invention can be represented by the following equation:

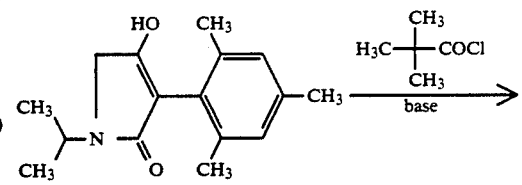

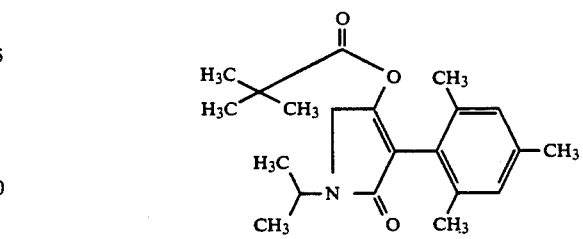

If, in accordance with process (B) (variant b), 3-(2,4,6-trimethylphenyl)-1-cyclopentyl-pyrrolidine-2,4-dione and acetic anhydride are used, the course of the process according to the invention can be represented by the following equation.

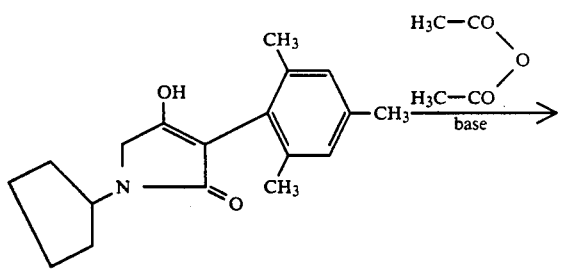

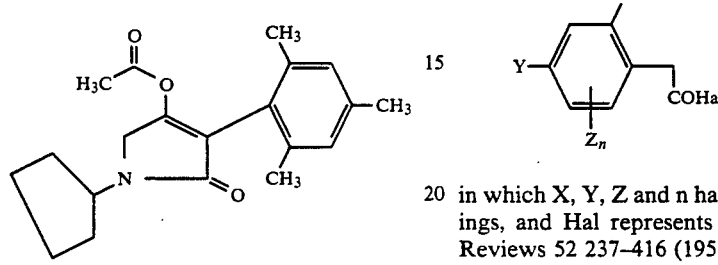

If, in accordance with process C, 3-(2,4-6-trimethyl-phenyl)-1-methoxyethyl-5-methyl-pyrrolidine-2,4-dione and ethoxyethyl chloroformate are used, the course of the process according to the invention can be represented by the following equation.

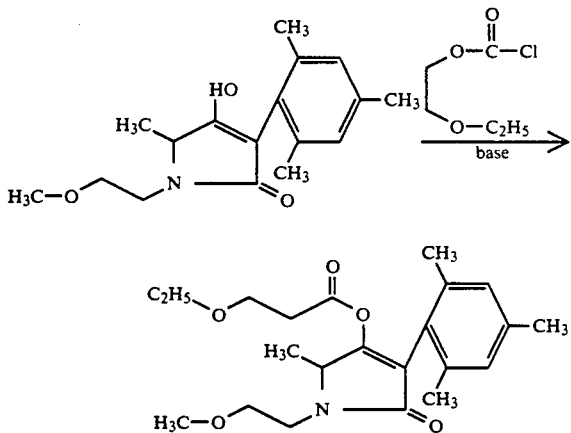

The compounds of the formula (II)

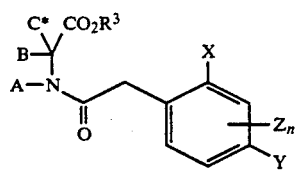
(II)

in which A, B, C*, X, Y, Z, n and $R^3$ have the abovementioned meanings and which are required as starting substances in the above process (A) are known in some cases, or they can be prepared in a simple manner by methods which are known in principle. Thus, for example, acylamino acid esters of the formula (II) are obtained when a) amino acid esters of the formula (VI)

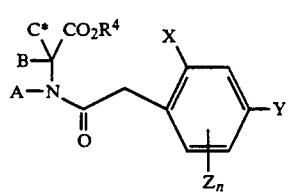
(VI)

in which $R^4$ represents hydrogen (VIa) and alkyl (VIb) and A, B and C* have the abovementioned meanings, are acylated with phenylacetic acid halides of the formula (VII)

$$\text{(VII)}$$

in which X, Y, Z and n have the abovementioned meanings, and Hal represents chlorine or bromine (Chem. Reviews 52 237–416 (1953));

or when acylamino acids of the formula (IIa)

$$\text{(IIa)}$$

in which A, B, C*, X, Y, Z and n have the abovementioned meanings and $R^4$ represents hydrogen, are esterified (Chem. Ind. (London) 1568 (1968).

Exemplary are the following compounds of the formula (II)

1. N-isopropyl-N-(2,4-dichlorophenyl-acetyl)-glycin-ethylester
2. N-isopropyl-N-(2,6-dichlorophenyl-acetyl)-glycin-ethylester
3. N-(2,6-dichlorophenyl-acetyl)-sarkosine-methylester
4. N-isopropyl-N-(2,6-dichlorophenyl-acetyl)-alanin-ethylester
5. N-methoxyethyl-N-(2,6-dichlorophenyl-acetyl)-glycin-ethylester
6. N-methoxyethyl-N-(2,6-dichlorophenyl-acetyl)-alanin-ethylester
7. N-tert-butyl-N-(2,6-dichlorophenyl-acetyl)-glycin-ethylester
8. N-methyl-N-(2,6-dichlorophenyl-acetyl)-alanin-ethylester
9. N-2-(2,4,4-trimethyl-pentyl)-N-(2,6-dichlorophenyl-acetyl)-glycin-ethylester
10. N-(2,4,6,-trimethylphenyl-acetyl)-sarkosine-ethylester
11. N-ethyl-N-(2,4,6-trimethylphenyl-acetyl)-glycin-methylester
12. N-isopropyl-N-(2,4,6-trimethylphenyl-acetyl)-glycin-ethylester
13. N-tert.-butyl-N-(2,4,6-trimethylphenyl-acetyl)-glycin-ethylester
14. N-iso-butyl-N-(2,4,6-trimethylphenyl-acetyl)-glycin-ethylester
15. N-sec-butyl-N-(2,4,6-trimethylphenyl-acetyl)-glycin-ethylester 16. N-neo-pentyl-N-(2,4,6-trimethylphenyl-acetyl)-glycin-ethylester
17. N-2-(2,3-dimethyl-butyl)-N-(2,4,6-trimethylphenyl-acetyl)-glycin-ethylester
18. N-2-(2,2,3-trimethyl-butyl)-N-(2,4,6-trimethylphenyl-acetyl)-glycin-ethylester
19. N-cyclopropyl-N-(2,4,6-trimethylphenyl-acetyl)-glycin-ethylester
20. N-cyclopentyl-N-(2,4,6-trimethylphenyl-acetyl)-glycin-ethylester
21. N-cyclohexyl-N-(2,4,6-trimethylphenyl-acetyl)-glycin-ethylester
22. N-alkyl-N-(2,4,6-trimethylphenyl-acetyl)-glycin-ethylester
23. N-benzyl-N-(2,4,6-trimethylphenyl-acetyl)-glycin-ethylester
24. N-2-(2,4,4-trimethyl-pentyl)-N-(2,4,6-trimethyl-phenyl-acetyl)-glycin-ethylester
25. N-methoxyethyl-N-(2,4,6-trimethylphenyl-acetyl)-glycin-ethylester
26. N-methoxypropyl-N-(2,4,6-trimethylphenyl-acetyl)-glycin-ethylester
27. N-methoxy-2-methyl-propyl-N-(2,4,6-trimethylphenyl-acetyl)-glycin-ethylester
28. N-2-(ethoxy-butyl)-N-(2,4,6-trimethylphenyl-acetyl)-glycin-ethylester
29. N-2-(methoxy-propyl)-N-(2,4,6-trimethylphenyl-acetyl)-glycin-ethylester
30. N-ethyl-mercaptoethyl-N-(2,4,6-trimethylphenyl-acetyl)-glycin-ethylester
31. N-methyl-N-(2,4,6-trimethylphenyl-acetyl)-alanin-ethylester
32. N-ethyl-N-(2,4,6-trimethylEpP098Ahenyl-acetyl)-alanin-ethylester
33. N-isopropyl-N-(2,4,6-trimethylphenyl-acetyl)-alanin-ethylester
34. N-isobutyl-N-(2,4,6-trimethylphenyl-acetyl)-alanin-ethylester
35. N-sec-butyl-N-(2,4,6-trimethylphenyl-acetyl)-alanin-ethylester
36. N-cyclopropyl-N-(2,4,6-trimethylphenyl-acetyl)-alanin-ethylester
37. N-cyclopropyl-N-(2,4,6-trimethylphenyl-acetyl)-alanin-ethylester
38. N-cyclohexyl-N-(2,4,6-trimethylphenyl-acetyl)-alanin-ethylester
39. N-methoxyethyl-N-(2,4,6-trimethylphenyl-acetyl)-alanin-ethylester
40. N-methoxypropyl-N-(2,4,6-trimethylphenyl-acetyl)-alanin-ethylester
41. N-methyl-N-(2,4,6-trimethylphenyl-acetyl)-2-amino-butyric acid-ethylester
42. N-ethyl-N-(2,4,6-trimethylphenyl-acetyl)-2-amino-butyric acid-ethylester
43. N-methyl-N-(2,4,6-trimethylphenyl-acetyl)-2-amino-valerian acid-ethylester
44. N-methyl-N-(2,4,6-trimethylphenyl-acetyl)-2-amino-iso-valerian acid-ethylester
45. N-ethyl-N-(2,4,6-trimethylphenyl-acetyl)-2-amino-valerian acid-ethylester
46. N-ethyl-N-(2,4,6-trimethylphenyl-acetyl)-2-amino-iso-valerian acid-ethylester
47. N-methyl-N-(2,4,6-trimethylphenyl-acetyl)-2-methyl-alanin-ethylester
48. N-ethyl-N-(2,4,6-trimethylphenyl-acetyl)-2-methyl-alanin-ethylester
49. N-isopropyl-N-(2,4,6-trimethylphenyl-acetyl)-2-methylalanin-ethylester Compounds of the formula (IIa) can be obtained, for example, from the phenylacetic acid halides of the formula (VII) and amino acids of the formula (VIa) by the method of Schotten-Baumann (Organikum [Laboratory Practical Organic Chemistry]9th Edition 446 (1970) VEB Deutscher Verlag der Wissenschaften, Berlin).

Compounds of the formula VI in which A, B, C and $R^4$ have the abovementioned meaning can be obtained by processes which are known from the literature, from a-halogenocarboxylic acids or esters and amines (Advanced Organic Chemistry, J. March p. 377, McGraw-Hill Inc. 1977).

Process (A) is characterized in that compounds of the formula (II) in which A, B, C, X, Y, Z, m, n and $R^3$ have the abovementioned meanings are subjected to intramolecular condensation in the presence of bases.

Diluents which can be employed in process (A) according to the invention are all customary inert organic solvents. Hydrocarbons, such as toluene and xylene, furthermore ethers, such as dibutyl ether, tetrahydrofuran, dioxane, glycol dimethyl ether and diglycol dimethyl ether, and also polar solvents, such as dimethyl sulphoxide, sulpholane, dimethylformamide and N-methyl-pyrrolidone, can preferably be used.

Deprotonating agents which can be employed when carrying out process (A) according to the invention are all customary proton acceptors. The oxides, hydroxides and carbonates of alkali metals and alkaline earth metals, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide, Adogen 464 (methyltrialkyl ($C_8$–$C_{10}$)ammonium chloride) or TDA 1 (tris-(methoxyethoxylethyl)-amine), can preferably be used. Furthermore, amides and hydrides of alkali metals and alkaline earth metals, such as sodium amide, sodium hydride and calcium hydride, and additionally also alkali metal alkoxides, such as sodium methoxide, sodium methoxide and potassium tert.-butoxide, can also be employed.

When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formulae (II) and the deprotonating bases are generally employed in approximately equimolar amounts. However, it is also possible to use one or the other components in a substantial excess (up to 3 moles).

Process (Ba) is characterized in that compounds of the formula (Ia) are reacted with carboxylic acid halides of the formula (III).

When the acid halides are used, the diluents which can be employed in process (Ba) according to the invention are all solvents which are inert towards these compounds. Hydrocarbons, such as benzine, benzene, toluene, xylene and tetralin, furthermore halogenohydrocarbons, such as methylene chloride, chloroform, carbon tetrachloride, chlorobenzene and o-dichlorobenzene, and additionally ketones, such as acetone and methyl isopropyl ketone, furthermore ethers, such as diethyl ether, tetrahydrofuran and dioxane, moreover carboxylic acid esters, such as ethyl acetate, and also strongly polar solvents, such as dimethyl sulphoxide and sulpholane, can preferably be used. If the stability of the acid halide towards hydrolysis permits, the reaction can also be carried out in the presence of water.

If the corresponding carboxylic acid halides are used, suitable acid-binding agents in the reaction of process (Ba) according to the invention are all customary acid acceptors. Tertiary amines, such as triethylamine, pyridine, diazabicyclooctane (DABCO), diazabicycloundecene (DBU), diazabicyclononbene (DBN), Hünig base and N,N-dimethyl-aniline, furthermore, alkaline earth metal oxides, such as magnesium oxide and calcium oxide, additionally alkali metal carbonates and alkaline earth metal carbonates, such as sodium carbonate, potassium carbonate and calcium carbonate, can preferably be used.

In process (Ba) according to the invention, the reaction temperatures can be varied within a substantial range, also when carboxylic acid halides are used. In general, the process is carried out at temperatures between −20° C. and +150° C., preferably between 0° C. and 100° C.

When carrying out process (Ba) according to the invention, the starting substances of the formula (Ia) and the carboxylic acid halide of the formula (III) are generally used in approximately equivalent amounts. However, it is also possible to employ the carboxylic anhydride in a substantial excess (up to 5 moles). Working up is carried out by customary methods.

Process (Bb) is characterized in that compounds of the formula (Ia) are reacted with carboxylic acid anhydrides of the formula (IV).

If, in process (Bb) according to the invention, carboxylic anhydrides are used as the reactant of the formula (IV), the diluents which can preferably be used are those diluents which are also preferably suitable when acid halides are used. Besides, a carboxylic acid anhydride, employed in excess, can also simultaneously act as the diluent.

When carrying out process (Bb) according to the invention, the reaction temperatures can be varied within a substantial range, also when carboxylic anhydrides are used. In general, the process is carried out at temperatures between −20° C. and +150° C., preferably between 0° C. and 100° C.

When the process according to the invention is carried out, the starting substances of the formula (Ia) and the carboxylic anhydride of the formula (IV) are generally used in approximately equivalent amounts. However, it is also possible to employ the carboxylic anhydride in a substantial excess (up to 5 moles). Working up is carried out by customary methods.

In general, a procedure is followed in which the diluent and any carboxylic anhydride which is present in excess as well as the carboxylic acid which forms are removed by distillation or by washing with an organic solvent or with water.

Process (C) is characterized in that compounds of the formula (Ia) are reacted with chloroformic acid esters of the formula (V).

If the corresponding chloroformic acit esters are used, suitable acid-binding agents in the reaction in process (C) according to the invention are all customary acid acceptors. Tertiary amines, such as triethylamine, pyridine, DABCO, DBC, DBA, Hünig base and N,N-dimethylaniline, furthermore alkaline earth metal oxides, such as magnesium oxide and calcium oxide, and additionally alkali metal carbonates and alkaline earth metal carbonates, such as sodium carbonate, potassium carbonate and calcium carbonate, can preferably be used.

When the chloroformic acid esters are used, the diluents which can be employed in process (C) according to the invention are all solvents which are inert towards these compounds. Hydrocarbons, such as benzine, benzene, toluene, xylene and tetralin, furthermore halogenohydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, moreover carboxylic acid esters, such as ethyl acetate, and also strongly polar solvents, such as dimethyl sulphoxide and sulpholane, can preferably be used.

When the chloroformic acid esters are used as carboxylic acid derivatives of the formula (V), the reaction temperatures can be varied within a substantial range when process (C) is carried out. If the process is carried out in the presence of a diluent and of an acid-binding agent, the reaction temperatures are generally between −20° C. and +100° C., preferably between 0° C. and 50° C.

Process (C) according to the invention is generally carried out under atmospheric pressure.

When process (C) according to the invention is carried out, the starting substances of the formula (Ia) and the corresponding chloroformic acid ester of the formula (V) are generally used in approximately equivalent amounts. However, it is also possible to employ one or the other component in a substantial excess (up to 2 moles). Working up is then carried out by customary methods. In general, a procedure is followed in which the salts which have precipitated are removed and the reaction mixture which remains is concentrated by stripping off the diluent.

EXAMPLE 1

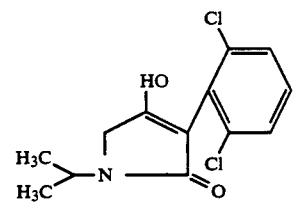

3.9 g (0.13 mol) of sodium hydride (80% strength) are initially introduced into 70 ml of absolute toluene. After 36.2 g (0.107 mol) of N-2,6-dichlorophenylacetyl-N-isopropyl-glycine ethyl ester in 160 ml of absolute toluene have been added dropwise, the mixture is refluxed for 6 hours. 20 ml of ethanol are added dropwise while cooling in an ice bath, the batch is evaporated in vacuo on a rotary evaporator, the residue is dissolved in 1 N NaOH, and 3-(2,6-dichlorophenyl)-1-isopropyl-pyrrolidine-2,4-dione is precipitated at 0°–20° C. using concentrated hydrochloric acid. For purification, the product is boiled in chloroform, n-hexane is subsequently added, and the colorless product which has precipitated is filtered off with suction.

Yield: 25.42 g (83 % of theory) m.p. >230° C.

EXAMPLE 2

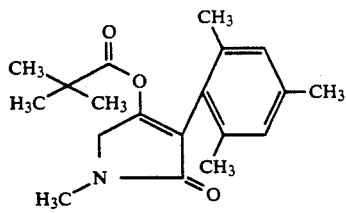

3.42 g (15 mmol) of 3-(2,4,6-trimethylphenyl)-1-methyl-pyrrolidine-2,4-dione are suspended in 50 ml of absolute tetrahydrofuran (THF), and 1.22 ml (15 mmol) of absolute pyridine and 2.54 ml (15 mmol) of ethyl-diisopropylamine are added. To this, 1.88 ml (15 mmol) of pivaloyl chloride dissolved in 5 ml of absolute THF are added dropwise at 0°–10° C., and stirring is continued for 30 minutes. The precikpitate is filtered off, the solution is evaporated in vacuo on a rotary evaporator, and the residue is chromatographed on silica gel using cyclohexane/ethyl acetate 1:1.

Crystallization from ether/n-hexane gives 3.8 g (80.4% of theory) of 4-(pivaloyloxy)-3-(2,4,6-trimethyl-phenyl)-1-methyl-3-pyrrolidine-2-one of melting point 75° C.

EXAMPLE 3

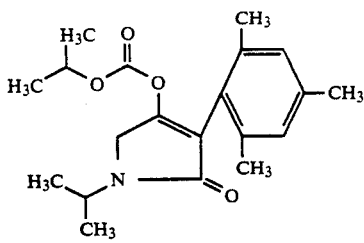

5.18 g (20 mmol) of 3-(2,4,6-trimethyl-phenyl)-1-iso-propyl-pyrrolidine-2,4-dione are suspended in 70 ml of tert.butyl-methyl ether (MTB-ether). After addition of 1.63 ml (20 mmol) of absolute pyridine and 3.4 ml (20 mmol) of ethyl-diisopropylamine 2.45 g (20 mmol) chloroformic acid-iso-propylester dissolved in 5 ml of MTB-ether are added dropwise at 0° to 10° C. and stirring is continued for 30 minutes. The precipitate is filtered off, the solution is evaporated in vacuo on a rotary evaporator and the residue is chromatographed on silica gel using cyclohexane/ethylacetate 1:1. Crystallization from n-hexane gives 4.67 g (67.6% of theory) of 4-iso-propoxy-carbonyloxy-3-(2,4,6-trimethylphenyl)-1-iso-propyl-3-pyrrolin-2-one of melting point 81° C. The 3-aryl-pyrrolidine-2,4-dione derivatives of the formula (Ia)–(Ic), which are listed in Tables 1–3 below by way of their formulae, are obtained analogously to the Preparation Examples and following the general preparation instructions.

TABLE 1

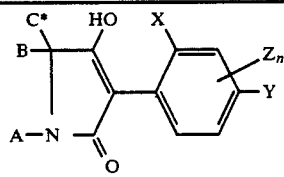

(Ia)

| Ex. No. | X | Y | $Z_n$ | A | B | C* | mp °C. |
|---|---|---|---|---|---|---|---|
| 4 | Cl | Cl | H | $(CH_3)_2CH-$ | H | H | 198 |
| 5 | Cl | H | 6-Cl | $CH_3-$ | H | H | 230 |
| 6 | Cl | H | 6-Cl | $CH_3-$ | $CH_3-$ | H | 221 |
| 7 | Cl | H | 6-Cl | $(CH_3)_2CH-$ | $CH_3-$ | $CH_3-$ | 180 |
| 8 | Cl | H | 6-Cl | $(CH_3)_3C-$ | H | H | >230 |
| 9 | Cl | H | 6-Cl | $(CH_3)_3C-CH_2-C(CH_3)_2-$ | H | H | >235 |
| 10 | Cl | H | 6-Cl | $(CH_3O-(CH_2)_2-$ | H | H | >230 |
| 11 | Cl | H | 6-Cl | $CH_3-O-(CH_2)_2-$ | H | H | 128 |
| 12 | $CH_3$ | $CH_3$ | $6-CH_3$ | $CH_3-$ | H | H | >230 |
| 13 | $CH_3$ | $CH_3$ | $6-CH_3$ | $CH_3-$ | $CH_3-$ | H | >230 |
| 14 | $CH_3$ | $CH_3$ | $6-CH_3$ | $CH_3-$ | $C_2H_5$ | H | 210 |
| 15 | $CH_3$ | $CH_3$ | $6-CH_3$ | $CH_3-$ | $C_3H_7$ | H | |
| 16 | $CH_3$ | $CH_3$ | $6-CH_3$ | $CH_3-$ | $(CH_3)_2CH-$ | H | |
| 17 | $CH_3$ | $CH_3$ | $6-CH_3$ | $CH_3-$ | $CH_3-$ | $CH_3-$ | |
| 18 | $CH_3$ | $CH_3$ | $6-CH_3$ | $C_2H_5$ | H | H | >230 |
| 19 | $CH_3$ | $CH_3$ | $6-CH_3$ | $C_2H_5$ | $CH_3-$ | H | 227 |
| 20 | $CH_3$ | $CH_3$ | $6-CH_3$ | $C_2H_5$ | $C_2H_5-$ | H | 184 |
| 21 | $CH_3$ | $CH_3$ | $6-CH_3$ | $C_2H_5$ | $C_3H_7-$ | H | |
| 22 | $CH_3$ | $CH_3$ | $6-CH_3$ | $C_2H_5$ | $(CH_3)_2CH-$ | H | |
| 23 | $CH_3$ | $CH_3$ | $6-CH_3$ | $C_2H_5$ | $CH_3-$ | $CH_3-$ | |
| 24 | $CH_3$ | $CH_3$ | $6-CH_3$ | $C_3H_7$ | H | H | |
| 25 | $CH_3$ | $CH_3$ | $6-CH_3$ | $C_3H_7$ | $CH_3-$ | H | |
| 26 | $CH_3$ | $CH_3$ | $6-CH_3$ | $C_3H_7$ | $C_2H_5-$ | H | |
| 27 | $CH_3$ | $CH_3$ | $6-CH_3$ | $C_3H_7$ | $C_3H_7$ | H | |
| 28 | $CH_3$ | $CH_3$ | $6-CH_3$ | $C_3H_7$ | $(CH_3)_2CH-$ | H | |
| 29 | $CH_3$ | $CH_3$ | $6-CH_3$ | $C_3H_7$ | $CH_3-$ | $CH_3-$ | |
| 30 | $CH_3$ | $CH_3$ | $6-CH_3$ | $(CH_3)_2CH-$ | H | H | >220 |
| 31 | $CH_3$ | $CH_3$ | $6-CH_3$ | $(CH_3)_2CH-$ | $CH_3-$ | H | 228 |
| 32 | $CH_3$ | $CH_3$ | $6-CH_3$ | $(CH_3)_2CH-$ | $C_2H_5$ | H | |
| 33 | $CH_3$ | $CH_3$ | $6-CH_3$ | $(CH_3)_2CH-$ | $C_3H_7$ | H | |
| 34 | $CH_3$ | $CH_3$ | $6-CH_3$ | $(CH_3)_2CH-$ | $(CH_3)_2CH-$ | H | |
| 35 | $CH_3$ | $CH_3$ | $6-CH_3$ | $(CH_3)_2CH-$ | $CH_3-$ | $CH_3-$ | |

TABLE 1-continued

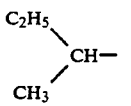
(Ia)

| Ex. No. | X | Y | $Z_n$ | A | B | C* | mp °C. |
|---|---|---|---|---|---|---|---|
| 36 | CH₃ | CH₃ | 6-CH₃ | C₄H₉ | H | H | |
| 37 | CH₃ | CH₃ | 6-CH₃ | C₄H₉ | CH₃— | H | |
| 38 | CH₃ | CH₃ | 6-CH₃ | (CH₃)₂CH—CH₂— | H | H | 209 |
| 39 | CH₃ | CH₃ | 6-CH₃ | (CH₃)₂CH—CH₂— | CH₃— | H | 189 |
| 40 | CH₃ | CH₃ | 6-CH₃ | C₂H₅\CH—/CH₃ | H | H | 262 |
| 41 | CH₃ | CH₃ | 6-CH₃ | C₂H₅\CH—/CH₃ | CH₃— | H | 205 |
| 42 | CH₃ | CH₃ | 6-CH₃ | (CH₃)₃C— | H | H | >230 |
| 43 | CH₃ | CH₃ | 6-CH₃ | (CH₃)₃C—CH₂— | H | H | >230 |
| 44 | CH₃ | CH₃ | 6-CH₃ | (CH₃)₂CH—CH(CH₃)— | H | H | >230 |
| 45 | CH₃ | CH₃ | 6-CH₃ | (CH₃)₃C—CH(CH₃)— | H | H | >230 |
| 46 | CH₃ | CH₃ | 6-CH₃ | (CH₃)₃C—CH₂—C(CH₃)₂— | H | H | >230 |
| 47 | CH₃ | CH₃ | 6-CH₃ | CH₂=CH—CH₂— | H | H | 212 |
| 48 | CH₃ | CH₃ | 6-CH₃ | CH₂=CH—CH₂— | CH₃— | H | |
| 49 | CH₃ | CH₃ | 6-CH₃ | 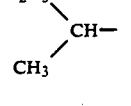 | H | H | >230 |
| 50 | CH₃ | CH₃ | 6-CH₃ |  | CH₃— | H | >230 |
| 51 | CH₃ | CH₃ | 6-CH₃ |  | C₂H₅— | H | |
| 52 | CH₃ | CH₃ | 6-CH₃ |  | C₃H₇— | H | |
| 53 | CH₃ | CH₃ | 6-CH₃ |  | (CH₃)₂CH— | H | |
| 54 | CH₃ | CH₃ | 6-CH₃ |  | CH₃— | CH₃— | |
| 55 | CH₃ | CH₃ | 6-CH₃ |  | H | H | >230 |
| 56 | CH₃ | CH₃ | 6-CH₃ | 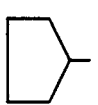 | CH₃— | H | 223 |
| 57 | CH₃ | CH₃ | 6-CH₃ | 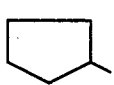 | C₂H₅— | H | |
| 58 | CH₃ | CH₃ | 6-CH₃ | 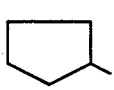 | C₃H₇— | H | |

TABLE 1-continued

 (Ia)

| Ex. No. | X | Y | $Z_n$ | A | B | C* | mp °C. |
|---|---|---|---|---|---|---|---|
| 59 | CH₃ | CH₃ | 6-CH₃ |  | (CH₃)₂CH— | H | |
| 60 | CH₃ | CH₃ | 6-CH₃ | 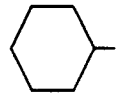 | CH₃— | CH₃— | |
| 61 | CH₃ | CH₃ | 6-CH₃ |  | H | H | >230 |
| 62 | CH₃ | CH₃ | 6-CH₃ |  | CH₃— | H | ·>230 |
| 63 | CH₃ | CH₃ | 6-CH₃ |  | C₂H₅— | H | |
| 64 | CH₃ | CH₃ | 6-CH₃ |  | C₃H₇— | H | |
| 65 | CH₃ | CH₃ | 6-CH₃ |  | (CH₃)₂CH— | H | |
| 66 | CH₃ | CH₃ | 6-CH₃ | 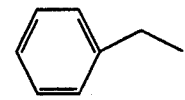 | CH₃— | CH₃— | |
| 67 | CH₃ | CH₃ | 6-CH₃ | 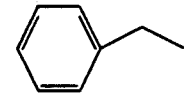 | H | H | >230 |
| 68 | CH₃ | CH₃ | 6-CH₃ |  | CH₃— | H | |
| 69 | CH₃ | CH₃ | 6-CH₃ | CH₃—O—(CH₂)₂— | H | H | 179 |
| 70 | CH₃ | CH₃ | 6-CH₃ | CH₃—O—(CH₂)₂— | CH₃— | H | 165 |
| 71 | CH₃ | CH₃ | 6-CH₃ | CH₃—O—CH₂—CH(CH₃)— | H | H | 220 |
| 72 | CH₃ | CH₃ | 6-CH₃ | CH₃—O—CH₂—CH(CH₃)— | CH₃— | H | |
| 73 | CH₃ | CH₃ | 6-CH₃ | CH₃—O—(CH₂)₃— | H | H | 190 |
| 74 | CH₃ | CH₃ | 6-CH₃ | CH₃—O—(CH₂)₃— | CH₃— | H | 175 |
| 75 | CH₃ | CH₃ | 6-CH₃ | C₂H₅—O—(CH₂)₂—CH(CH₃)— | H | H | 220 |
| 76 | CH₃ | CH₃ | 6-CH₃ | C₂H₅—O—(CH₂)₂—CH(CH₃)— | CH₃— | H | |
| 77 | CH₃ | CH₃ | 6-CH₃ | CH₃—O—CH₂—CH(CH₃)—CH₂— | H | H | 156 |
| 78 | CH₃ | CH₃ | 6-CH₃ | C₂H₅—S—(CH₂)₂— | H | H | 165 |

TABLE 2

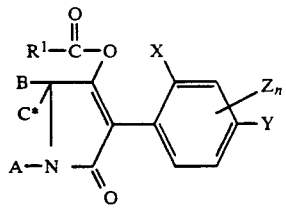
(Ib)

| Ex. No. | X | Y | $Z_n$ | A | B | C* | $R^1$ | mp °C. |
|---|---|---|---|---|---|---|---|---|
| 79 | Cl | Cl | H | $(CH_3)_2CH-$ | H | H | $CH_3-$ | 128 |
| 80 | Cl | H | 6-Cl | $CH_3-$ | $CH_3-$ | H | $CH_3-$ | 125 |
| 81 | Cl | H | 6-Cl | $CH_3-$ | $CH_3-$ | H | $(CH_3)_2CH-$ | Öl |
| 82 | Cl | H | 6-Cl | $CH_3-$ | $CH_3-$ | H | $(CH_3)_3C-$ | 68 |
| 83 | Cl | H | 6-Cl | $(CH_3)_2CH-$ | H | H | $CH_3-$ | 113 |
| 84 | Cl | H | 6-Cl | $(CH_3)_2CH-$ | H | H | $(CH_3)_2CH-$ | 105 |
| 85 | Cl | H | 6-Cl | $(CH_3)_2CH-$ | H | H | $(CH_3)_3C-$ | 122 |
| 86 | Cl | H | 6-Cl | $(CH_3)_2CH-$ | H | H | $(CH_3)_2CH-C(CH_3)_2-$ | 112 |
| 87 | Cl | H | 6-Cl | $(CH_3)_3C-$ | H | H | $CH_3-$ | 113 |
| 88 | Cl | H | 6-Cl | $(CH_3)_3C-$ | H | H | $(CH_3)_2CH-$ | 117 |
| 89 | Cl | H | 6-Cl | $(CH_3)_3C-$ | H | H | $(CH_3)_3C-$ | 158 |
| 90 | $CH_3$ | $CH_3$ | 6-$CH_3$ | $CH_3-$ | H | H | $CH_3-$ | Öl |
| 91 | $CH_3$ | $CH_3$ | 6-$CH_3$ | $CH_3-$ | H | H | $(CH_3)_2CH-$ | Öl |
| 92 | $CH_3$ | $CH_3$ | 6-$CH_3$ | $CH_3-$ | H | H | $(CH_3)_2CH-C(CH_3)_2-$ | 45 |
| 93 | $CH_3$ | $CH_3$ | 6-$CH_3$ | $CH_3-$ | $CH_3-$ | H | $CH_3-$ | 75 |
| 94 | $CH_3$ | $CH_3$ | 6-$CH_3$ | $CH_3-$ | $CH_3-$ | H | $(CH_3)_2CH-$ | Öl |
| 95 | $CH_3$ | $CH_3$ | 6-$CH_3$ | $CH_3-$ | $CH_3-$ | H | $(CH_3)_3C-$ | Öl |
| 96 | $CH_3$ | $CH_3$ | 6-$CH_3$ | $CH_3-$ | $CH_3-$ | H | $(CH_3)_2CH-C(CH_3)_2-$ | |
| 97 | $CH_3$ | $CH_3$ | 6-$CH_3$ | $CH_3-$ | $CH_3-$ | H | $(CH_3)_3C-CH_2-$ | oil |
| 98 | $CH_3$ | $CH_3$ | 6-$CH_3$ | $CH_3-$ | $CH_3-$ | H | $CH_3O-CH_2-C(CH_3)_2-$ | oil |
| 99 | $CH_3$ | $CH_3$ | 6-$CH_3$ | $CH_3-$ | $CH_3-$ | H | $ClCH_2-C(CH_3)_2-$ | oil |
| 100 | $CH_3$ | $CH_3$ | 6-$CH_3$ | $CH_3-$ | $CH_3-$ | H | $CH_3O-CH_2-C(CH_3)(CH_3)-CH_2-OCH_3$ | |
| 101 | $CH_3$ | $CH_3$ | 6-$CH_3$ | $CH_3-$ | $CH_3-$ | H | $(CH_3)_2C=CH-$ | |
| 102 | $CH_3$ | $CH_3$ | 6-$CH_3$ | $CH_3-$ | $CH_3-$ | H | dioxane-$CH_3$ | |
| 103 | $CH_3$ | $CH_3$ | 6-$CH_3$ | $CH_3-$ | $C_2H_5-$ | H | $CH_3-$ | |
| 104 | $CH_3$ | $CH_3$ | 6-$CH_3$ | $CH_3-$ | $C_2H_5-$ | H | $(CH_3)_2CH-$ | |
| 105 | $CH_3$ | $CH_3$ | 6-$CH_3$ | $CH_3-$ | $C_2H_5-$ | H | $(CH_3)_3C-$ | |
| 106 | $CH_3$ | $CH_3$ | 6-$CH_3$ | $CH_3-$ | $C_2H_5-$ | H | $(CH_3)_2CH-C(CH_3)_2-$ | |
| 107 | $CH_3$ | $CH_3$ | 6-$CH_3$ | $CH_3-$ | $C_2H_5-$ | H | $(CH_3)_3C-CH_2-$ | |
| 108 | $CH_3$ | $CH_3$ | 6-$CH_3$ | $CH_3-$ | $C_2H_5-$ | H | $CH_3O-CH_2-C(CH_3)_2-$ | |
| 109 | $CH_3$ | $CH_3$ | 6-$CH_3$ | $CH_3-$ | $C_2H_5-$ | H | $ClCH_2-C(CH_3)_2-$ | |
| 110 | $CH_3$ | $CH_3$ | 6-$CH_3$ | $CH_3-$ | $C_2H_5-$ | H | $CH_3O-CH_2-C(CH_3)(CH_3)-CH_2-OCH_3$ | |
| 111 | $CH_3$ | $CH_3$ | 6-$CH_3$ | $CH_3-$ | $C_2H_5-$ | H | $(CH_3)_2C=CH-$ | |
| 112 | $CH_3$ | $CH_3$ | 6-$CH_3$ | $CH_3-$ | $C_2H_5-$ | H | dioxane-$CH_3$ | |
| 113 | $CH_3$ | $CH_3$ | 6-$CH_3$ | $CH_3-$ | $C_3H_7-$ | H | $CH_3-$ | |
| 114 | $CH_3$ | $CH_3$ | 6-$CH_3$ | $CH_3-$ | $C_3H_7-$ | H | $(CH_3)_2CH-$ | |
| 115 | $CH_3$ | $CH_3$ | 6-$CH_3$ | $CH_3-$ | $C_3H_7-$ | H | $(CH_3)_3C-$ | |
| 116 | $CH_3$ | $CH_3$ | 6-$CH_3$ | $CH_3-$ | $C_3H_7-$ | H | $(CH_3)_2CH-C(CH_3)_2-$ | |
| 117 | $CH_3$ | $CH_3$ | 6-$CH_3$ | $CH_3-$ | $(CH_3)_2CH-$ | H | $CH_3-$ | |
| 118 | $CH_3$ | $CH_3$ | 6-$CH_3$ | $CH_3-$ | $(CH_3)_2CH-$ | H | $(CH_3)_2CH-$ | |
| 119 | $CH_3$ | $CH_3$ | 6-$CH_3$ | $CH_3-$ | $(CH_3)_2CH-$ | H | $(CH_3)_3C-$ | |
| 120 | $CH_3$ | $CH_3$ | 6-$CH_3$ | $CH_3-$ | $(CH_3)_2CH-$ | H | $(CH_3)_2CH-C(CH_3)_2-$ | |
| 121 | $CH_3$ | $CH_3$ | 6-$CH_3$ | $CH_3-$ | $CH_3-$ | $CH_3-$ | $CH_3-$ | |
| 122 | $CH_3$ | $CH_3$ | 6-$CH_3$ | $CH_3-$ | $CH_3-$ | $CH_3-$ | $(CH_3)_2CH-$ | |
| 123 | $CH_3$ | $CH_3$ | 6-$CH_3$ | $CH_3-$ | $CH_3-$ | $CH_3-$ | $(CH_3)_3C-$ | |

TABLE 2-continued

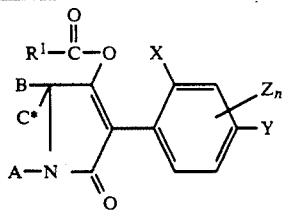
(Ib)

| Ex. No. | X | Y | $Z_n$ | A | B | C* | $R^1$ | mp °C. |
|---|---|---|---|---|---|---|---|---|
| 124 | $CH_3$ | $CH_3$ | 6-$CH_3$ | $CH_3-$ | $CH_3-$ | $CH_3-$ | $(CH_3)_2-CH-C(CH_3)_2-$ | |
| 125 | $CH_3$ | $CH_3$ | 6-$CH_3$ | $C_2H_5$ | H | H | $CH_3-$ | 85 |
| 126 | $CH_3$ | $CH_3$ | 6-$CH_3$ | $C_2H_5$ | H | H | $(CH_3)_2CH-$ | |
| 127 | $CH_3$ | $CH_3$ | 6-$CH_3$ | $C_2H_5$ | H | H | $(CH_3)_3C-$ | 99 |
| 128 | $CH_3$ | $CH_3$ | 6-$CH_3$ | $C_2H_5$ | H | H | $(CH_3)_2-CH-C(CH_3)_2-$ | |
| 129 | $CH_3$ | $CH_3$ | 6-$CH_3$ | $C_2H_5$ | H | H | $(CH_3)_3C-CH_2-$ | |
| 130 | $CH_3$ | $CH_3$ | 6-$CH_3$ | $C_2H_5$ | H | H | $CH_3O-CH_2-C(CH_3)_2-$ | |
| 131 | $CH_3$ | $CH_3$ | 6-$CH_3$ | $C_2H_5$ | H | H | $ClCH_2-C(CH_3)_2-$ | |
| 132 | $CH_3$ | $CH_3$ | 6-$CH_3$ | $C_2H_5$ | H | H | $\begin{array}{c}CH_3O\\CH_3O\end{array}\!\!\!\!\!\!\!\!\!\!\!\!\succ\!\!\!\!\!\!\!\!\!\!CH_3$ | |
| 133 | $CH_3$ | $CH_3$ | 6-$CH_3$ | $C_2H_5-$ | H | H | $(CH_3)_2C=CH-$ | |
| 134 | $CH_3$ | $CH_3$ | 6-$CH_3$ | $C_2H_5-$ | H | H | (dioxane-$CH_3$) | |
| 135 | $CH_3$ | $CH_3$ | 6-$CH_3$ | $C_2H_5-$ | $CH_3-$ | H | $CH_3-$ | oil |
| 136 | $CH_3$ | $CH_3$ | 6-$CH_3$ | $C_2H_5-$ | $CH_3-$ | H | $(CH_3)_2CH-$ | |
| 137 | $CH_3$ | $CH_3$ | 6-$CH_3$ | $C_2H_5-$ | $CH_3-$ | H | $(CH_3)_3C-$ | oil |
| 138 | $CH_3$ | $CH_3$ | 6-$CH_3$ | $C_2H_5-$ | $CH_3-$ | H | $(CH_3)_2-CH-C(CH_3)_2-$ | |
| 139 | $CH_3$ | $CH_3$ | 6-$CH_3$ | $C_2H_5-$ | $CH_3-$ | H | $(CH_3)_3C-CH_2-$ | oil |
| 140 | $CH_3$ | $CH_3$ | 6-$CH_3$ | $C_2H_5-$ | $CH_3-$ | H | $CH_3O-CH_2-C(CH_3)_2-$ | |
| 141 | $CH_3$ | $CH_3$ | 6-$CH_3$ | $C_2H_5-$ | $CH_3-$ | H | $ClCH_2-C(CH_3)_2-$ | |
| 142 | $CH_3$ | $CH_3$ | 6-$CH_3$ | $C_2H_5-$ | $CH_3-$ | H | $\begin{array}{c}CH_3O\\CH_3O\end{array}\!\!\!\!\!\!\!\!\!\!\!\!\succ\!\!\!\!\!\!\!\!\!\!CH_3$ | |
| 143 | $CH_3$ | $CH_3$ | 6-$CH_3$ | $C_2H_5-$ | $CH_3-$ | H | $(CH_3)_2C=CH-$ | |
| 144 | $CH_3$ | $CH_3$ | 6-$CH_3$ | $C_2H_5-$ | $CH_3-$ | H | (dioxane-$CH_3$) | |
| 145 | $CH_3$ | $CH_3$ | 6-$CH_3$ | $C_2H_5-$ | $C_2H_5-$ | H | $CH_3-$ | |
| 146 | $CH_3$ | $CH_3$ | 6-$CH_3$ | $C_2H_5-$ | $C_2H_5-$ | H | $(CH_3)_2CH-$ | |
| 147 | $CH_3$ | $CH_3$ | 6-$CH_3$ | $C_2H_5-$ | $C_2H_5-$ | H | $(CH_3)_3C-$ | |
| 148 | $CH_3$ | $CH_3$ | 6-$CH_3$ | $C_2H_5-$ | $C_2H_5-$ | H | $(CH_3)_2-CH-C(CH_3)_2-$ | |
| 149 | $CH_3$ | $CH_3$ | 6-$CH_3$ | $C_2H_5-$ | $C_2H_5-$ | H | $(CH_3)_3C-CH_2-$ | |
| 150 | $CH_3$ | $CH_3$ | 6-$CH_3$ | $C_2H_5-$ | $C_2H_5-$ | H | $CH_3O-CH_2-C(CH_3)_2-$ | |
| 151 | $CH_3$ | $CH_3$ | 6-$CH_3$ | $C_2H_5-$ | $C_2H_5-$ | H | $ClCH_2-C(CH_3)_2-$ | |
| 152 | $CH_3$ | $CH_3$ | 6-$CH_3$ | $C_2H_5-$ | $C_2H_5-$ | H | $\begin{array}{c}CH_3O\\CH_3O\end{array}\!\!\!\!\!\!\!\!\!\!\!\!\succ\!\!\!\!\!\!\!\!\!\!CH_3$ | |
| 153 | $CH_3$ | $CH_3$ | 6-$CH_3$ | $C_2H_5-$ | $C_2H_5-$ | H | $(CH_3)_2C=CH-$ | |
| 154 | $CH_3$ | $CH_3$ | 6-$CH_3$ | $C_2H_5-$ | $C_2H_5-$ | H | (dioxane-$CH_3$) | |
| 155 | $CH_3$ | $CH_3$ | 6-$CH_3$ | $C_2H_5-$ | $C_3H_7-$ | H | $CH_3-$ | |
| 156 | $CH_3$ | $CH_3$ | 6-$CH_3$ | $C_2H_5-$ | $C_3H_7-$ | H | $(CH_3)_2CH-$ | |

TABLE 2-continued

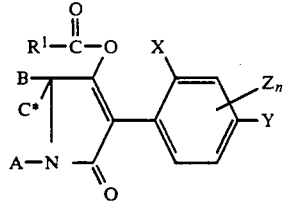
(Ib)

| Ex. No. | X | Y | $Z_n$ | A | B | C* | $R^1$ | mp °C. |
|---|---|---|---|---|---|---|---|---|
| 157 | $CH_3$ | $CH_3$ | 6-$CH_3$ | $C_2H_5-$ | $C_3H_7-$ | H | $(CH_3)_3C-$ | |
| 158 | $CH_3$ | $CH_3$ | 6-$CH_3$ | $C_2H_5-$ | $C_3H_7-$ | H | $(CH_3)_2CH-C(CH_3)_2-$ | |
| 159 | $CH_3$ | $CH_3$ | 6-$CH_3$ | $C_2H_5-$ | $(CH_3)_2CH-$ | H | $CH_3-$ | |
| 160 | $CH_3$ | $CH_3$ | 6-$CH_3$ | $C_2H_5-$ | $(CH_3)_2CH-$ | H | $(CH_3)_2CH-$ | |
| 161 | $CH_3$ | $CH_3$ | 6-$CH_3$ | $C_2H_5-$ | $(CH_3)_2CH-$ | H | $(CH_3)_3C-$ | |
| 162 | $CH_3$ | $CH_3$ | 6-$CH_3$ | $C_2H_5-$ | $(CH_3)_2CH-$ | H | $(CH_3)_2CH-C(CH_3)_2-$ | |
| 163 | $CH_3$ | $CH_3$ | 6-$CH_3$ | $C_2H_5-$ | $CH_3-$ | $CH_3-$ | $CH_3-$ | |
| 164 | $CH_3$ | $CH_3$ | 6-$CH_3$ | $C_2H_5-$ | $CH_3-$ | $CH_3-$ | $(CH_3)_2CH-$ | |
| 165 | $CH_3$ | $CH_3$ | 6-$CH_3$ | $C_2H_5-$ | $CH_3-$ | $CH_3-$ | $(CH_3)_3C-$ | |
| 166 | $CH_3$ | $CH_3$ | 6-$CH_3$ | $C_2H_5-$ | $CH_3-$ | $CH_3-$ | $(CH_3)_2CH-C(CH_3)_2-$ | |
| 167 | $CH_3$ | $CH_3$ | 6-$CH_3$ | $C_3H_7$ | H | H | $CH_3-$ | |
| 168 | $CH_3$ | $CH_3$ | 6-$CH_3$ | $C_3H_7-$ | H | H | $(CH_3)_2CH-$ | |
| 169 | $CH_3$ | $CH_3$ | 6-$CH_3$ | $C_3H_7-$ | H | H | $(CH_3)_3C-$ | |
| 170 | $CH_3$ | $CH_3$ | 6-$CH_3$ | $C_3H_7-$ | H | H | $(CH_3)_2-CH-C(CH_3)_2-$ | |
| 171 | $CH_3$ | $CH_3$ | 6-$CH_3$ | $C_3H_7-$ | H | H | $(CH_3)_3C-CH_3-$ | |
| 172 | $CH_3$ | $CH_3$ | 6-$CH_3$ | $C_3H_7-$ | H | H | $CH_3O-CH_2-C(CH_3)_2-$ | |
| 173 | $CH_3$ | $CH_3$ | 6-$CH_3$ | $C_3H_7-$ | H | H | $ClCH_2-C(CH_3)_2-$ | |
| 174 | $CH_3$ | $CH_3$ | 6-$CH_3$ | $C_3H_7-$ | H | H | $CH_3O-CH_2-C(CH_3)(CH_3)-CH_2-OCH_3$ | |
| 175 | $CH_3$ | $CH_3$ | 6-$CH_3$ | $C_3H_7-$ | H | H | $(CH_3)_2C=CH-$ | |
| 176 | $CH_3$ | $CH_3$ | 6-$CH_3$ | $C_3H_7-$ | H | H | (1,3-dioxane-CH_3) | |
| 177 | $CH_3$ | $CH_3$ | 6-$CH_3$ | $C_3H_7-$ | $CH_3-$ | H | $CH_3-$ | |
| 178 | $CH_3$ | $CH_3$ | 6-$CH_3$ | $C_3H_7-$ | $CH_3-$ | H | $(CH_3)_2CH-$ | |
| 179 | $CH_3$ | $CH_3$ | 6-$CH_3$ | $C_3H_7-$ | $CH_3-$ | H | $(CH_3)_3C-$ | |
| 180 | $CH_3$ | $CH_3$ | 6-$CH_3$ | $C_3H_7-$ | $CH_3-$ | H | $(CH_3)_2-CH-C(CH_3)_2-$ | |
| 181 | $CH_3$ | $CH_3$ | 6-$CH_3$ | $C_3H_7-$ | $CH_3-$ | H | $(CH_3)_3C-CH_2-$ | |
| 182 | $CH_3$ | $CH_3$ | 6-$CH_3$ | $C_3H_7-$ | $CH_3-$ | H | $CH_3O-CH_2-C(CH_3)_2-$ | |
| 183 | $CH_3$ | $CH_3$ | 6-$CH_3$ | $C_3H_7-$ | $CH_3-$ | H | $ClCH_2-C(CH_3)_2-$ | |
| 184 | $CH_3$ | $CH_3$ | 6-$CH_3$ | $C_3H_7-$ | $CH_3-$ | H | $CH_3O-CH_2-C(CH_3)(CH_3)-CH_2-OCH_3$ | |
| 185 | $CH_3$ | $CH_3$ | 6-$CH_3$ | $C_3H_7-$ | $CH_3-$ | H | $(CH_3)_2C=CH-$ | |
| 186 | $CH_3$ | $CH_3$ | 6-$CH_3$ | $C_3H_7-$ | $CH_3-$ | H | (1,3-dioxane-CH_3) | |
| 187 | $CH_3$ | $CH_3$ | 6-$CH_3$ | $C_3H_7-$ | $C_2H_5-$ | H | $CH_3-$ | |
| 188 | $CH_3$ | $CH_3$ | 6-$CH_3$ | $C_3H_7-$ | $C_2H_5-$ | H | $(CH_3)_2CH-$ | |
| 189 | $CH_3$ | $CH_3$ | 6-$CH_3$ | $C_3H_7-$ | $C_2H_5-$ | H | $(CH_3)_3C-$ | |
| 190 | $CH_3$ | $CH_3$ | 6-$CH_3$ | $C_3H_7-$ | $C_2H_5-$ | H | $(CH_3)_2-CH-C(CH_3)_2-$ | |
| 191 | $CH_3$ | $CH_3$ | 6-$CH_3$ | $C_3H_7-$ | $C_2H_5-$ | H | $(CH_3)_3C-CH_2-$ | |
| 192 | $CH_3$ | $CH_3$ | 6-$CH_3$ | $C_3H_7-$ | $C_2H_5-$ | H | $CH_3O-CH_2-C(CH_3)_2-$ | |
| 193 | $CH_3$ | $CH_3$ | 6-$CH_3$ | $C_3H_7-$ | $C_2H_5-$ | H | $ClCH_2-C(CH_3)_2-$ | |
| 194 | $CH_3$ | $CH_3$ | 6-$CH_3$ | $C_3H_7-$ | $C_2H_5-$ | H | $CH_3O-CH_2-C(CH_3)(CH_3)-CH_2-OCH_3$ | |
| 195 | $CH_3$ | $CH_3$ | 6-$CH_3$ | $C_3H_7-$ | $C_2H_5-$ | H | $(CH_3)_2C=CH-$ | |

TABLE 2-continued (Ib)

| Ex. No. | X | Y | $Z_n$ | A | B | C* | $R^1$ | mp °C. |
|---|---|---|---|---|---|---|---|---|
| 196 | $CH_3$ | $CH_3$ | 6-$CH_3$ | $C_3H_7$— | $C_2H_5$— | H | (4-methyl-1,3-dioxan-4-yl) | |
| 197 | $CH_3$ | $CH_3$ | 6-$CH_3$ | $C_3H_7$— | $C_3H_7$— | H | $CH_3$— | |
| 198 | $CH_3$ | $CH_3$ | 6-$CH_3$ | $C_3H_7$— | $C_3H_7$— | H | $(CH_3)_2CH$— | |
| 199 | $CH_3$ | $CH_3$ | 6-$CH_3$ | $C_3H_7$— | $C_3H_7$— | H | $(CH_3)_3C$— | |
| 200 | $CH_3$ | $CH_3$ | 6-$CH_3$ | $C_3H_7$— | $C_3H_7$— | H | $(CH_3)_2CH$—$C(CH_3)_2$— | |
| 201 | $CH_3$ | $CH_3$ | 6-$CH_3$ | $C_3H_7$— | $(CH_3)_2CH$— | H | $CH_3$— | |
| 202 | $CH_3$ | $CH_3$ | 6-$CH_3$ | $C_3H_7$— | $(CH_3)_2CH$— | H | $(CH_3)_2CH$— | |
| 203 | $CH_3$ | $CH_3$ | 6-$CH_3$ | $C_3H_7$— | $(CH_3)_2CH$— | H | $(CH_3)_3C$— | |
| 204 | $CH_3$ | $CH_3$ | 6-$CH_3$ | $C_3H_7$— | $(CH_3)_2CH$— | H | $(CH_3)_2CH$—$C(CH_3)_2$— | |
| 205 | $CH_3$ | $CH_3$ | 6-$CH_3$ | $C_3H_7$— | $CH_3$— | $CH_3$— | $CH_3$— | |
| 206 | $CH_3$ | $CH_3$ | 6-$CH_3$ | $C_3H_7$— | $CH_3$— | $CH_3$— | $(CH_3)_2CH$— | |
| 207 | $CH_3$ | $CH_3$ | 6-$CH_3$ | $C_3H_7$— | $CH_3$— | $CH_3$— | $(CH_3)_3C$— | |
| 208 | $CH_3$ | $CH_3$ | 6-$CH_3$ | $C_3H_7$— | $CH_3$— | $CH_3$— | $(CH_3)_2CH$—$C(CH_3)_2$— | |
| 209 | $CH_3$ | $CH_3$ | 6-$CH_3$ | $(CH_3)_2CH$— | H | H | $CH_3$— | 75 |
| 210 | $CH_3$ | $CH_3$ | 6-$CH_3$ | $(CH_3)_2CH$— | H | H | $(CH_3)_2CH$— | 80 |
| 211 | $CH_3$ | $CH_3$ | 6-$CH_3$ | $(CH_3)_2CH$— | H | H | $(CH_3)_3C$— | 86 |
| 212 | $CH_3$ | $CH_3$ | 6-$CH_3$ | $(CH_3)_2CH$— | H | H | $(CH_3)_2CH$—$C(CH_3)_2$— | 108 |
| 213 | $CH_3$ | $CH_3$ | 6-$CH_3$ | $(CH_3)_2CH$— | H | H | $(CH_3)_3C$—$CH_2$— | 74 |
| 214 | $CH_3$ | $CH_3$ | 6-$CH_3$ | $(CH_3)_2CH$— | H | H | $CH_3O$—$CH_2$—$C(CH_3)_2$— | 68 |
| 215 | $CH_3$ | $CH_3$ | 6-$CH_3$ | $(CH_3)_2CH$— | H | H | $ClCH_2$—$C(CH_3)_2$— | 153 |
| 216 | $CH_3$ | $CH_3$ | 6-$CH_3$ | $(CH_3)_2CH$— | H | H | $(CH_3O-CH_2)_2C(CH_3)$— | |
| 217 | $CH_3$ | $CH_3$ | 6-$CH_3$ | $(CH_3)_2CH$— | H | H | $(CH_3)_2C$=$CH$— | 67 |
| 218 | $CH_3$ | $CH_3$ | 6-$CH_3$ | $(CH_3)_2CH$— | H | H | (4-methyl-1,3-dioxan-4-yl) | |
| 219 | $CH_3$ | $CH_3$ | 6-$CH_3$ | $(CH_3)_2CH$— | H | H | 2-$NO_2$-$C_6H_4$— | |
| 220 | $CH_3$ | $CH_3$ | 6-$CH_3$ | $(CH_3)_2CH$— | H | H | 3-$NO_2$-$C_6H_4$— | |
| 221 | $CH_3$ | $CH_3$ | 6-$CH_3$ | $(CH_3)_2CH$— | H | H | 4-$NO_2$-$C_6H_4$— | |
| 222 | $CH_3$ | $CH_3$ | 6-$CH_3$ | $(CH_3)_2CH$— | H | H | 2-Cl-$C_6H_4$— | |

TABLE 2-continued

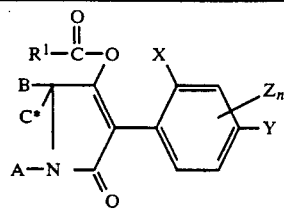
(Ib)

| Ex. No. | X | Y | $Z_n$ | A | B | C* | $R^1$ | mp °C. |
|---|---|---|---|---|---|---|---|---|
| 223 | CH₃ | CH₃ | 6-CH₃ | (CH₃)₂CH— | H | H | 3-Cl-C₆H₄— | |
| 224 | CH₃ | CH₃ | 6-CH₃ | (CH₃)₂CH— | H | H | 4-Cl-C₆H₄— | |
| 225 | CH₃ | CH₃ | 6-CH₃ | (CH₃)₂CH— | H | H | 2-CH₃-C₆H₄— | |
| 226 | CH₃ | CH₃ | 6-CH₃ | (CH₃)₂CH— | H | H | 3-CH₃-C₆H₄— | |
| 227 | CH₃ | CH₃ | 6-CH₃ | (CH₃)₂CH— | H | H | 4-CH₃-C₆H₄— | |
| 228 | CH₃ | CH₃ | 6-CH₃ | (CH₃)₂CH— | H | H | 2-OCH₃-C₆H₄— | |
| 229 | CH₃ | CH₃ | 6-CH₃ | (CH₃)₂CH— | H | H | 3-OCH₃-C₆H₄— | |
| 230 | CH₃ | CH₃ | 6-CH₃ | (CH₃)₂CH— | H | H | 4-OCH₃-C₆H₄— | |
| 231 | CH₃ | CH₃ | 6-CH₃ | (CH₃)₂CH— | CH₃ | H | CH₃— | oil |
| 232 | CH₃ | CH₃ | 6-CH₃ | (CH₃)₂CH— | CH₃ | H | (CH₃)₂CH— | |
| 233 | CH₃ | CH₃ | 6-CH₃ | (CH₃)₂CH— | CH₃ | H | (CH₃)₃C— | 94 |
| 234 | CH₃ | CH₃ | 6-CH₃ | (CH₃)₂CH— | CH₃ | H | (CH₃)₂—CH—C(CH₃)₂— | |
| 235 | CH₃ | CH₃ | 6-CH₃ | (CH₃)₂CH— | CH₃ | H | (CH₃)₃C—CH₂— | oil |
| 236 | CH₃ | CH₃ | 6-CH₃ | (CH₃)₂CH— | CH₃ | H | CH₃O—CH₂—C(CH₃)₂— | |
| 237 | CH₃ | CH₃ | 6-CH₃ | (CH₃)₂CH— | CH₃ | H | ClCH₂—C(CH₃)₂— | 112 |
| 238 | CH₃ | CH₃ | 6-CH₃ | (CH₃)₂CH— | CH₃ | H | (CH₃O-CH₂)₂C(CH₃)— | |
| 239 | CH₃ | CH₃ | 6-CH₃ | (CH₃)₂CH— | CH₃ | H | (CH₃)₂C=CH— | |

TABLE 2-continued

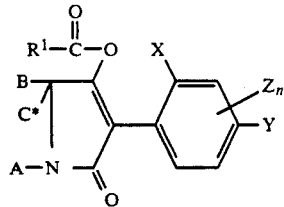
(Ib)

| Ex. No. | X | Y | $Z_n$ | A | B | C* | $R^1$ | mp °C. |
|---|---|---|---|---|---|---|---|---|
| 240 | $CH_3$ | $CH_3$ | 6-$CH_3$ | $(CH_3)_2CH-$ | $CH_3$ | H | (dioxane-$CH_3$ ring) | |
| 241 | $CH_3$ | $CH_3$ | 6-$CH_3$ | $(CH_3)_2CH-$ | $C_2H_5-$ | H | $CH_3-$ | |
| 242 | $CH_3$ | $CH_3$ | 6-$CH_3$ | $(CH_3)_2CH-$ | $C_2H_5-$ | H | $(CH_3)_2CH-$ | |
| 243 | $CH_3$ | $CH_3$ | 6-$CH_3$ | $(CH_3)_2CH-$ | $C_2H_5-$ | H | $(CH_3)_3C-$ | |
| 244 | $CH_3$ | $CH_3$ | 6-$CH_3$ | $(CH_3)_2CH-$ | $C_2H_5-$ | H | $(CH_3)_2-CH-C(CH_3)_2-$ | |
| 245 | $CH_3$ | $CH_3$ | 6-$CH_3$ | $(CH_3)_2CH-$ | $C_2H_5-$ | H | $(CH_3)_3C-CH_2-$ | |
| 246 | $CH_3$ | $CH_3$ | 6-$CH_3$ | $(CH_3)_2CH-$ | $C_2H_5-$ | H | $CH_3O-CH_2-C(CH_3)_2-$ | |
| 247 | $CH_3$ | $CH_3$ | 6-$CH_3$ | $(CH_3)_2CH-$ | $C_2H_5-$ | H | $ClCH_2-C(CH_3)_2-$ | |
| 248 | $CH_3$ | $CH_3$ | 6-$CH_3$ | $(CH_3)_2CH-$ | $C_2H_5-$ | H | $CH_3O-CH_2-C(CH_3)(CH_2OCH_3)-$ | |
| 249 | $CH_3$ | $CH_3$ | 6-$CH_3$ | $(CH_3)_2CH-$ | $C_2H_5-$ | H | $(CH_3)_2C=CH-$ | |
| 250 | $CH_3$ | $CH_3$ | 6-$CH_3$ | $(CH_3)_2CH-$ | $C_2H_5-$ | H | (dioxane-$CH_3$ ring) | |
| 251 | $CH_3$ | $CH_3$ | 6-$CH_3$ | $(CH_3)_2CH-$ | $C_3H_7-$ | H | $CH_3-$ | |
| 252 | $CH_3$ | $CH_3$ | 6-$CH_3$ | $(CH_3)_2CH-$ | $C_3H_7-$ | H | $(CH_3)_2CH-$ | |
| 253 | $CH_3$ | $CH_3$ | 6-$CH_3$ | $(CH_3)_2CH-$ | $C_3H_7-$ | H | $(CH_3)_3C-$ | |
| 254 | $CH_3$ | $CH_3$ | 6-$CH_3$ | $(CH_3)_2CH-$ | $C_3H_7-$ | H | $(CH_3)_2CH-C(CH_3)_2-$ | |
| 255 | $CH_3$ | $CH_3$ | 6-$CH_3$ | $(CH_3)_2CH-$ | $(CH_3)_2CH-$ | H | $CH_3-$ | |
| 256 | $CH_3$ | $CH_3$ | 6-$CH_3$ | $(CH_3)_2CH-$ | $(CH_3)_2CH-$ | H | $(CH_3)_2CH-$ | |
| 257 | $CH_3$ | $CH_3$ | 6-$CH_3$ | $(CH_3)_2CH-$ | $(CH_3)_2CH-$ | H | $(CH_3)_3C-$ | |
| 258 | $CH_3$ | $CH_3$ | 6-$CH_3$ | $(CH_3)_2CH-$ | $(CH_3)_2CH-$ | H | $(CH_3)_2CH-C(CH_3)_2-$ | |
| 259 | $CH_3$ | $CH_3$ | 6-$CH_3$ | $(CH_3)_2CH-$ | $CH_3-$ | $CH_3-$ | $CH_3-$ | |
| 260 | $CH_3$ | $CH_3$ | 6-$CH_3$ | $(CH_3)_2CH-$ | $CH_3-$ | $CH_3-$ | $(CH_3)_2CH-$ | |
| 261 | $CH_3$ | $CH_3$ | 6-$CH_3$ | $(CH_3)_2CH-$ | $CH_3-$ | $CH_3-$ | $(CH_3)_3C-$ | |
| 262 | $CH_3$ | $CH_3$ | 6-$CH_3$ | $(CH_3)_2CH-$ | $CH_3-$ | $CH_3-$ | $(CH_3)_2CH-C(CH_3)_2-$ | |
| 263 | $CH_3$ | $CH_3$ | 6-$CH_3$ | $C_4H_9-$ | H | H | $CH_3-$ | |
| 264 | $CH_3$ | $CH_3$ | 6-$CH_3$ | $C_4H_9-$ | H | H | $(CH_3)_2CH-$ | |
| 265 | $CH_3$ | $CH_3$ | 6-$CH_3$ | $C_4H_9-$ | H | H | $(CH_3)_3C-$ | |
| 266 | $CH_3$ | $CH_3$ | 6-$CH_3$ | $C_4H_9-$ | H | H | $(CH_3)_2CH-C(CH_3)_2-$ | |
| 267 | $CH_3$ | $CH_3$ | 6-$CH_3$ | $C_4H_9-$ | $CH_3-$ | H | $CH_3-$ | |
| 268 | $CH_3$ | $CH_3$ | 6-$CH_3$ | $C_4H_9-$ | $CH_3-$ | H | $(CH_3)_2CH-$ | |
| 269 | $CH_3$ | $CH_3$ | 6-$CH_3$ | $C_4H_9-$ | $CH_3-$ | H | $(CH_3)_3C-$ | |
| 270 | $CH_3$ | $CH_3$ | 6-$CH_3$ | $C_4H_9-$ | $CH_3-$ | H | $(CH_3)_2CH-C(CH_3)_2-$ | |
| 271 | $CH_3$ | $CH_3$ | 6-$CH_3$ | $(CH_3)_2CH-CH_2-$ | H | H | $CH_3-$ | oil |
| 272 | $CH_3$ | $CH_3$ | 6-$CH_3$ | $(CH_3)_2CH-CH_2-$ | H | H | $(CH_3)_2CH-$ | oil |
| 273 | $CH_3$ | $CH_3$ | 6-$CH_3$ | $(CH_3)_2CH-CH_2-$ | H | H | $(CH_3)_3C-$ | oil |
| 274 | $CH_3$ | $CH_3$ | 6-$CH_3$ | $(CH_3)_2CH-CH_2-$ | H | H | $(CH_3)_2CH-C(CH_3)_2-$ | oil |
| 275 | $CH_3$ | $CH_3$ | 6-$CH_3$ | $(CH_3)_2CH-CH_2-$ | $CH_3-$ | H | $CH_3-$ | 73 |
| 276 | $CH_3$ | $CH_3$ | 6-$CH_3$ | $(CH_3)_2CH-CH_2-$ | $CH_3-$ | H | $(CH_3)_3C-$ | oil |
| 277 | $CH_3$ | $CH_3$ | 6-$CH_3$ | $(CH_3)_2CH-CH_2-$ | $CH_3-$ | H | $(CH_3)_3C-CH_2-$ | oil |
| 278 | $CH_3$ | $CH_3$ | 6-$CH_3$ | $(CH_3)_2CH-CH_2-$ | $CH_3-$ | H | $(CH_3)_2CH-C(CH_3)_2-$ | |
| 279 | $CH_3$ | $CH_3$ | 6-$CH_3$ | $C_2H_5(CH_3)CH-$ | H | H | $CH_3-$ | oil |
| 280 | $CH_3$ | $CH_3$ | 6-$CH_3$ | $C_2H_5(CH_3)CH-$ | H | H | $(CH_3)_2CH-$ | 66 |

TABLE 2-continued

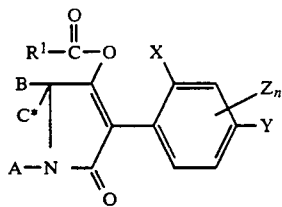
(Ib)

| Ex. No. | X | Y | $Z_n$ | A | B | C* | $R^1$ | mp °C. |
|---|---|---|---|---|---|---|---|---|
| 281 | $CH_3$ | $CH_3$ | 6-$CH_3$ | $C_2H_5$-CH(-)-$CH_3$ | H | H | $(CH_3)_3C-$ | 99 |
| 282 | $CH_3$ | $CH_3$ | 6-$CH_3$ | $C_2H_5$-CH(-)-$CH_3$ | H | H | $(CH_3)_2CH-C(CH_3)_2-$ | 66 |
| 283 | $CH_3$ | $CH_3$ | 6-$CH_3$ | $C_2H_5$-CH(-)-$CH_3$ | $CH_3-$ | H | $CH_3-$ | oil |
| 284 | $CH_3$ | $CH_3$ | 6-$CH_3$ | $C_2H_5$-CH(-)-$CH_3$ | $CH_3-$ | H | $(CH_3)_2CH-$ | |
| 285 | $CH_3$ | $CH_3$ | 6-$CH_3$ | $C_2H_5$-CH(-)-$CH_3$ | $CH_3-$ | H | $(CH_3)_3C-$ | 100 |
| 286 | $CH_3$ | $CH_3$ | 6-$CH_3$ | $C_2H_5$-CH(-)-$CH_3$ | $CH_3-$ | H | $(CH_3)_2CH-C(CH_3)_2-$ | |
| 287 | $CH_3$ | $CH_3$ | 6-$CH_3$ | $(CH_3)_3C-$ | H | H | $(CH_3)_2CH-$ | oil |
| 288 | $CH_3$ | $CH_3$ | 6-$CH_3$ | $(CH_3)_3C-$ | H | H | $(CH_3)_3C-$ | 85 |
| 289 | $CH_3$ | $CH_3$ | 6-$CH_3$ | $(CH_3)_3C-$ | H | H | $(CH_3)_2CH-C(CH_3)_2-$ | 107 |
| 290 | $CH_3$ | $CH_3$ | 6-$CH_3$ | $(CH_3)_3C-CH_2-$ | H | H | $CH_3-$ | oil |
| 291 | $CH_3$ | $CH_3$ | 6-$CH_3$ | $(CH_3)_3C-CH_2-$ | H | H | $(CH_3)_2CH-$ | |
| 292 | $CH_3$ | $CH_3$ | 6-$CH_3$ | $(CH_3)_3C-CH_2-$ | H | H | $(CH_3)_3C-$ | 83 |
| 293 | $CH_3$ | $CH_3$ | 6-$CH_3$ | $(CH_3)_3C-CH_2-$ | H | H | $(CH_3)_2CH-C(CH_3)_2-$ | |
| 294 | $CH_3$ | $CH_3$ | 6-$CH_3$ | $(CH_3)_2CH-CH(CH_3)-$ | H | H | $CH_3-$ | |
| 295 | $CH_3$ | $CH_3$ | 6-$CH_3$ | $(CH_3)_2CH-CH(CH_3)-$ | H | H | $(CH_3)_2CH-$ | |
| 296 | $CH_3$ | $CH_3$ | 6-$CH_3$ | $(CH_3)_2CH-CH(CH_3)-$ | H | H | $(CH_3)_3C-$ | |
| 297 | $CH_3$ | $CH_3$ | 6-$CH_3$ | $(CH_3)_2CH-CH(CH_3)-$ | H | H | $(CH_3)_2CH-C(CH_3)_2-$ | |
| 298 | $CH_3$ | $CH_3$ | 6-$CH_3$ | $(CH_3)_2CH-CH(CH_3)-$ | H | H | $CH_3-$ | oil |
| 299 | $CH_3$ | $CH_3$ | 6-$CH_3$ | $(CH_3)_2CH-CH(CH_3)-$ | H | H | $(CH_3)_2CH-$ | |
| 300 | $CH_3$ | $CH_3$ | 6-$CH_3$ | $(CH_3)_2CH-CH(CH_3)-$ | H | H | $(CH_3)_3C-$ | 92 |
| 301 | $CH_3$ | $CH_3$ | 6-$CH_3$ | $(CH_3)_2CH-CH(CH_3)-$ | H | H | $(CH_3)_2CH-C(CH_3)_2-$ | |
| 302 | $CH_3$ | $CH_3$ | 6-$CH_3$ | $CH_2=CH-CH_2-$ | H | H | $CH_3-$ | oil |
| 303 | $CH_3$ | $CH_3$ | 6-$CH_3$ | $CH_2=CH-CH_2-$ | H | H | $(CH_3)_2CH-$ | oil |
| 304 | $CH_3$ | $CH_3$ | 6-$CH_3$ | $CH_2=CH-CH_2-$ | H | H | $(CH_3)_3C-$ | oil |
| 305 | $CH_3$ | $CH_3$ | 6-$CH_3$ | $CH_2=CH-CH_2-$ | H | H | $(CH_3)_2CH-C(CH_3)_2-$ | oil |
| 306 | $CH_3$ | $CH_3$ | 6-$CH_3$ | $CH_2=CH-CH_2-$ | $CH_3-$ | H | $CH_3-$ | |
| 307 | $CH_3$ | $CH_3$ | 6-$CH_3$ | $CH_2=CH-CH_2-$ | $CH_3-$ | H | $(CH_3)_2CH-$ | |
| 308 | $CH_3$ | $CH_3$ | 6-$CH_3$ | $CH_2=CH-CH_2-$ | $CH_3-$ | H | $(CH_3)_3C-$ | |
| 309 | $CH_3$ | $CH_3$ | 6-$CH_3$ | $CH_2=CH-CH_2-$ | $CH_3-$ | H | $(CH_3)_2CH-C(CH_3)_2-$ | |
| 310 | $CH_3$ | $CH_3$ | 6-$CH_3$ | cyclopropyl | H | H | $CH_3-$ | oil |
| 311 | $CH_3$ | $CH_3$ | 6-$CH_3$ | cyclopropyl | H | H | $(CH_3)_2CH-$ | 35 |

TABLE 2-continued

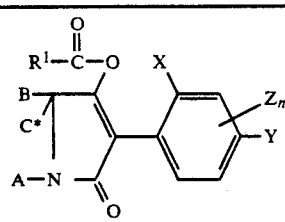

(Ib)

| Ex. No. | X | Y | $Z_n$ | A | B | C* | $R^1$ | mp °C. |
|---|---|---|---|---|---|---|---|---|
| 312 | $CH_3$ | $CH_3$ | 6-$CH_3$ | ▷ | H | H | $(CH_3)_3C-$ | 75 |
| 313 | $CH_3$ | $CH_3$ | 6-$CH_3$ | ▷ | H | H | $(CH_3)_2CH-C(CH_3)_2-$ | |
| 314 | $CH_3$ | $CH_3$ | 6-$CH_3$ | ▷ | H | H | $(CH_3)_3C-CH_2-$ | |
| 315 | $CH_3$ | $CH_3$ | 6-$CH_3$ | ▷ | H | H | $CH_3O-CH_2-C(CH_3)_2-$ | |
| 316 | $CH_3$ | $CH_3$ | 6-$CH_3$ | ▷ | H | H | $ClCH_2-C(CH_3)_2-$ | |
| 317 | $CH_3$ | $CH_3$ | 6-$CH_3$ | ▷ | H | H | $CH_3O-CH_2-C(CH_3)(CH_2OCH_3)-$ | |
| 318 | $CH_3$ | $CH_3$ | 6-$CH_3$ | ▷ | H | H | $(CH_3)_2C=CH-$ | |
| 319 | $CH_3$ | $CH_3$ | 6-$CH_3$ | ▷ | H | H | (1,3-dioxan-2-yl-methyl, $CH_3$) | |
| 320 | $CH_3$ | $CH_3$ | 6-$CH_3$ | ▷ | $CH_3$ | H | $CH_3-$ | 83 |
| 321 | $CH_3$ | $CH_3$ | 6-$CH_3$ | ▷ | $CH_3$ | H | $(CH_3)_2CH-$ | |
| 322 | $CH_3$ | $CH_3$ | 6-$CH_3$ | ▷ | $CH_3$ | H | $(CH_3)_3C-$ | oil |
| 323 | $CH_3$ | $CH_3$ | 6-$CH_3$ | ▷ | $CH_3$ | H | $(CH_3)_2-CH-C(CH_3)_2-$ | |
| 324 | $CH_3$ | $CH_3$ | 6-$CH_3$ | ▷ | $CH_3$ | H | $(CH_3)_3C-CH_2-$ | oil |
| 325 | $CH_3$ | $CH_3$ | 6-$CH_3$ | ▷ | $CH_3$ | H | $CH_3O-CH_2-C(CH_3)_2-$ | |
| 326 | $CH_3$ | $CH_3$ | 6-$CH_3$ | ▷ | $CH_3$ | H | $ClCH_2-C(CH_3)_2-$ | |
| 327 | $CH_3$ | $CH_3$ | 6-$CH_3$ | ▷ | $CH_3$ | H | $CH_3O-CH_2-C(CH_3)(CH_2OCH_3)-$ | |

TABLE 2-continued

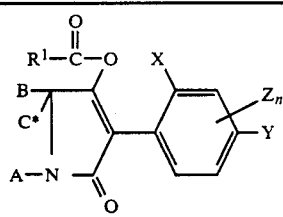
(Ib)

| Ex. No. | X | Y | $Z_n$ | A | B | C* | $R^1$ | mp °C. |
|---|---|---|---|---|---|---|---|---|
| 328 | $CH_3$ | $CH_3$ | 6-$CH_3$ | ▷ | $CH_3$ | H | $(CH_3)_2C=CH—$ | |
| 329 | $CH_3$ | $CH_3$ | 6-$CH_3$ | ▷ | $CH_3$ | H | (dioxane-CH3) | |
| 330 | $CH_3$ | $CH_3$ | 6-$CH_3$ | ▷ | $C_2H_5—$ | H | $CH_3—$ | |
| 331 | $CH_3$ | $CH_3$ | 6-$CH_3$ | ▷ | $C_2H_5—$ | H | $(CH_3)_2CH—$ | |
| 332 | $CH_3$ | $CH_3$ | 6-$CH_3$ | ▷ | $C_2H_5—$ | H | $(CH_3)_3C—$ | |
| 333 | $CH_3$ | $CH_3$ | 6-$CH_3$ | ▷ | $C_2H_5—$ | H | $(CH_3)_2—CH—C(CH_3)_2—$ | |
| 334 | $CH_3$ | $CH_3$ | 6-$CH_3$ | ▷ | $C_2H_5—$ | H | $(CH_3)_3C—CH_2—$ | |
| 335 | $CH_3$ | $CH_3$ | 6-$CH_3$ | ▷ | $C_2H_5—$ | H | $CH_3O—CH_2—C(CH_3)_2—$ | |
| 336 | $CH_3$ | $CH_3$ | 6-$CH_3$ | ▷ | $C_2H_5—$ | H | $ClCH_2—C(CH_3)_2—$ | |
| 337 | $CH_3$ | $CH_3$ | 6-$CH_3$ | ▷ | $C_2H_5—$ | H | $(CH_3O-CH_2)_2C(CH_3)—$ | |
| 338 | $CH_3$ | $CH_3$ | 6-$CH_3$ | ▷ | $C_2H_5—$ | H | $(CH_3)_2C=CH—$ | |
| 339 | $CH_3$ | $CH_3$ | 6-$CH_3$ | ▷ | $C_2H_5—$ | H | (dioxane-CH3) | |
| 340 | $CH_3$ | $CH_3$ | 6-$CH_3$ | ▷ | $C_3H_7—$ | H | $CH_3—$ | |
| 341 | $CH_3$ | $CH_3$ | 6-$CH_3$ | ▷ | $C_3H_7—$ | H | $(CH_3)_2CH—$ | |
| 342 | $CH_3$ | $CH_3$ | 6-$CH_3$ | ▷ | $C_3H_7—$ | H | $(CH_3)_3C—$ | |

TABLE 2-continued

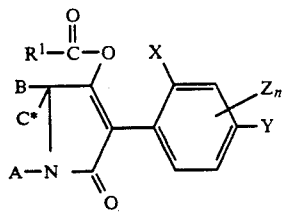
(Ib)

| Ex. No. | X | Y | $Z_n$ | A | B | C* | $R^1$ | mp °C. |
|---|---|---|---|---|---|---|---|---|
| 343 | $CH_3$ | $CH_3$ | 6-$CH_3$ | cyclopropyl | $C_3H_7$— | H | $(CH_3)_2CH$—$C(CH_3)_2$— | |
| 344 | $CH_3$ | $CH_3$ | 6-$CH_3$ | cyclopropyl | $(CH_3)_2CH$— | H | $CH_3$— | |
| 345 | $CH_3$ | $CH_3$ | 6-$CH_3$ | cyclopropyl | $(CH_3)_2CH$— | H | $(CH_3)_2CH$— | |
| 346 | $CH_3$ | $CH_3$ | 6-$CH_3$ | cyclopropyl | $(CH_3)_2CH$— | H | $(CH_3)_3C$— | |
| 347 | $CH_3$ | $CH_3$ | 6-$CH_3$ | cyclopropyl | $(CH_3)_2CH$— | H | $(CH_3)_2CH$—$C(CH_3)_2$— | |
| 348 | $CH_3$ | $CH_3$ | 6-$CH_3$ | cyclopropyl | $CH_3$— | $CH_3$— | $CH_3$— | |
| 349 | $CH_3$ | $CH_3$ | 6-$CH_3$ | cyclopropyl | $CH_3$— | $CH_3$— | $(CH_3)_2CH$— | |
| 350 | $CH_3$ | $CH_3$ | 6-$CH_3$ | cyclopropyl | $CH_3$— | $CH_3$— | $(CH_3)_3C$— | |
| 351 | $CH_3$ | $CH_3$ | 6-$CH_3$ | cyclopropyl | $CH_3$— | $CH_3$— | $(CH_3)_2CH$—$C(CH_3)_2$— | |
| 352 | $CH_3$ | $CH_3$ | 6-$CH_3$ | methylcyclopentyl | H | H | $CH_3$— | 60 |
| 353 | $CH_3$ | $CH_3$ | 6-$CH_3$ | methylcyclopentyl | H | H | $(CH_3)_2CH$— | oil |
| 354 | $CH_3$ | $CH_3$ | 6-$CH_3$ | methylcyclopentyl | H | H | $(CH_3)_3C$— | 80 |
| 355 | $CH_3$ | $CH_3$ | 6-$CH_3$ | methylcyclopentyl | H | H | $(CH_3)_2$—$CH$—$C(CH_3)_2$— | 85 |
| 356 | $CH_3$ | $CH_3$ | 6-$CH_3$ | methylcyclopentyl | H | H | $(CH_3)_3C$—$CH_2$— | 74 |
| 357 | $CH_3$ | $CH_3$ | 6-$CH_3$ | methylcyclopentyl | H | H | $CH_3O$—$CH_2$—$C(CH_3)_2$— | |

TABLE 2-continued

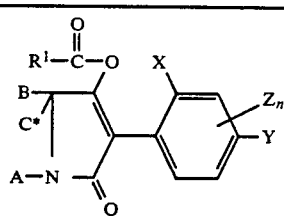
(Ib)

| Ex. No. | X | Y | $Z_n$ | A | B | C* | $R^1$ | mp °C. |
|---|---|---|---|---|---|---|---|---|
| 358 | $CH_3$ | $CH_3$ | 6-$CH_3$ | cyclopentyl | H | H | $ClCH_2-C(CH_3)_2-$ | 94 |
| 359 | $CH_3$ | $CH_3$ | 6-$CH_3$ | cyclopentyl | H | H | $CH_3OCH_2-C(CH_3)(CH_3)-CH_2OCH_3$ | 39 |
| 360 | $CH_3$ | $CH_3$ | 6-$CH_3$ | cyclopentyl | H | H | $(CH_3)_2C=CH-$ | oil |
| 361 | $CH_3$ | $CH_3$ | 6-$CH_3$ | cyclopentyl | H | H | 2-methyl-1,3-dioxan-2-yl | |
| 362 | $CH_3$ | $CH_3$ | 6-$CH_3$ | cyclopentyl | $CH_3-$ | H | $CH_3-$ | 96 |
| 363 | $CH_3$ | $CH_3$ | 6-$CH_3$ | cyclopentyl | $CH_3-$ | H | $(CH_3)_2CH-$ | oil |
| 364 | $CH_3$ | $CH_3$ | 6-$CH_3$ | cyclopentyl | $CH_3-$ | H | $(CH_3)_3C-$ | 63 |
| 365 | $CH_3$ | $CH_3$ | 6-$CH_3$ | cyclopentyl | $CH_3-$ | H | $(CH_3)_2CH-C(CH_3)_2-$ | |
| 366 | $CH_3$ | $CH_3$ | 6-$CH_3$ | cyclopentyl | $CH_3-$ | H | $(CH_3)_3C-CH_2-$ | |
| 367 | $CH_3$ | $CH_3$ | 6-$CH_3$ | cyclopentyl | $CH_3-$ | H | $CH_3O-CH_2-C(CH_3)_2-$ | |
| 368 | $CH_3$ | $CH_3$ | 6-$CH_3$ | cyclopentyl | $CH_3-$ | H | $ClCH_2-C(CH_3)_2-$ | |
| 369 | $CH_3$ | $CH_3$ | 6-$CH_3$ | cyclopentyl | $CH_3-$ | H | $CH_3OCH_2-C(CH_3)(CH_3)-CH_2OCH_3$ | |
| 370 | $CH_3$ | $CH_3$ | 6-$CH_3$ | cyclopentyl | $CH_3-$ | H | $(CH_3)_2C=CH-$ | |

TABLE 2-continued

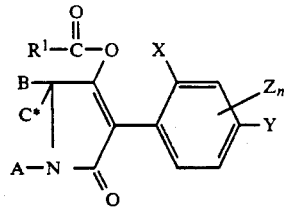
(Ib)

| Ex. No. | X | Y | $Z_n$ | A | B | C* | $R^1$ | mp °C. |
|---|---|---|---|---|---|---|---|---|
| 371 | $CH_3$ | $CH_3$ | 6-$CH_3$ | cyclopentyl | $CH_3-$ | H | dioxane-CH_3 | |
| 372 | $CH_3$ | $CH_3$ | 6-$CH_3$ | cyclopentyl | $C_2H_5-$ | H | $CH_3-$ | |
| 373 | $CH_3$ | $CH_3$ | 6-$CH_3$ | cyclopentyl | $C_2H_5-$ | H | $(CH_3)_2CH-$ | |
| 374 | $CH_3$ | $CH_3$ | 6-$CH_3$ | cyclopentyl | $C_2H_5-$ | H | $(CH_3)_3C-$ | |
| 375 | $CH_3$ | $CH_3$ | 6-$CH_3$ | cyclopentyl | $C_2H_5-$ | H | $(CH_3)_2-CH-C(CH_3)_2-$ | |
| 376 | $CH_3$ | $CH_3$ | 6-$CH_3$ | cyclopentyl | $C_2H_5-$ | H | $(CH_3)_3C-CH_2-$ | |
| 377 | $CH_3$ | $CH_3$ | 6-$CH_3$ | cyclopentyl | $C_2H_5-$ | H | $CH_3O-CH_2-C(CH_3)_2-$ | |
| 378 | $CH_3$ | $CH_3$ | 6-$CH_3$ | cyclopentyl | $C_2H_5-$ | H | $ClCH_2-C(CH_3)_2-$ | |
| 379 | $CH_3$ | $CH_3$ | 6-$CH_3$ | cyclopentyl | $C_2H_5-$ | H | $(CH_3OCH_2)_2C(CH_3)-$ | |
| 380 | $CH_3$ | $CH_3$ | 6-$CH_3$ | cyclopentyl | $C_2H_5-$ | H | $(CH_3)_2C=CH-$ | |
| 381 | $CH_3$ | $CH_3$ | 6-$CH_3$ | cyclopentyl | $C_2H_5-$ | H | dioxane-CH_3 | |
| 382 | $CH_3$ | $CH_3$ | 6-$CH_3$ | cyclopentyl | $C_3H_7-$ | H | $CH_3-$ | |
| 383 | $CH_3$ | $CH_3$ | 6-$CH_3$ | cyclopentyl | $C_3H_7-$ | H | $(CH_3)_2CH-$ | |

TABLE 2-continued

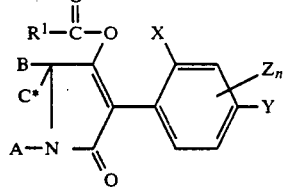
(Ib)

| Ex. No. | X | Y | $Z_n$ | A | B | C* | $R^1$ | mp °C. |
|---|---|---|---|---|---|---|---|---|
| 384 | $CH_3$ | $CH_3$ | 6-$CH_3$ | cyclopentyl | $C_3H_7-$ | H | $(CH_3)_3C-$ | |
| 385 | $CH_3$ | $CH_3$ | 6-$CH_3$ | cyclopentyl | $C_3H_7-$ | H | $(CH_3)_2CH-C(CH_3)_2-$ | |
| 386 | $CH_3$ | $CH_3$ | 6-$CH_3$ | cyclopentyl | $(CH_3)_2CH-$ | H | $CH_3-$ | |
| 387 | $CH_3$ | $CH_3$ | 6-$CH_3$ | cyclopentyl | $(CH_3)_2CH-$ | H | $(CH_3)_2CH-$ | |
| 388 | $CH_3$ | $CH_3$ | 6-$CH_3$ | cyclopentyl | $(CH_3)_2CH-$ | H | $(CH_3)_3C-$ | |
| 389 | $CH_3$ | $CH_3$ | 6-$CH_3$ | cyclopentyl | $(CH_3)_2CH-$ | H | $(CH_3)_2CH-C(CH_3)_2-$ | |
| 390 | $CH_3$ | $CH_3$ | 6-$CH_3$ | cyclopentyl | $CH_3-$ | $CH_3-$ | $CH_3-$ | |
| 391 | $CH_3$ | $CH_3$ | 6-$CH_3$ | cyclopentyl | $CH_3-$ | $CH_3-$ | $(CH_3)_2CH-$ | |
| 392 | $CH_3$ | $CH_3$ | 6-$CH_3$ | cyclopentyl | $CH_3-$ | $CH_3-$ | $(CH_3)_3C-$ | |
| 393 | $CH_3$ | $CH_3$ | 6-$CH_3$ | cyclopentyl | $CH_3-$ | $CH_3-$ | $(CH_3)_2CH-C(CH_3)_2-$ | |
| 394 | $CH_3$ | $CH_3$ | 6-$CH_3$ | cyclohexyl | H | H | $CH_3-$ | 78 |
| 395 | $CH_3$ | $CH_3$ | 6-$CH_3$ | cyclohexyl | H | H | $(CH_3)_2CH-$ | oil |
| 396 | $CH_3$ | $CH_3$ | 6-$CH_3$ | cyclohexyl | H | H | $(CH_3)_3C-$ | 97 |

TABLE 2-continued

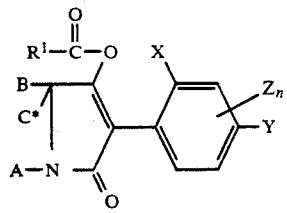
(Ib)

| Ex. No. | X | Y | $Z_n$ | A | B | C* | $R^1$ | mp °C. |
|---|---|---|---|---|---|---|---|---|
| 397 | $CH_3$ | $CH_3$ | 6-$CH_3$ | cyclohexyl | H | H | $(CH_3)_2CH-C(CH_3)_2-$ | 122 |
| 398 | $CH_3$ | $CH_3$ | 6-$CH_3$ | cyclohexyl | H | H | $(CH_3)_3C-CH_2-$ | |
| 399 | $CH_3$ | $CH_3$ | 6-$CH_3$ | cyclohexyl | H | H | $CH_3O-CH_2-C(CH_3)_2-$ | |
| 400 | $CH_3$ | $CH_3$ | 6-$CH_3$ | cyclohexyl | H | H | $ClCH_2-C(CH_3)_2-$ | |
| 401 | $CH_3$ | $CH_3$ | 6-$CH_3$ | cyclohexyl | H | H | $CH_3O-CH_2-C(CH_3)(CH_2-OCH_3)-$ | |
| 402 | $CH_3$ | $CH_3$ | 6-$CH_3$ | cyclohexyl | H | H | $(CH_3)_2C=CH-$ | |
| 403 | $CH_3$ | $CH_3$ | 6-$CH_3$ | cyclohexyl | H | H | 5-methyl-1,3-dioxan-5-yl | |
| 404 | $CH_3$ | $CH_3$ | 6-$CH_3$ | cyclohexyl | $CH_3-$ | H | $CH_3-$ | 84 |
| 405 | $CH_3$ | $CH_3$ | 6-$CH_3$ | cyclohexyl | $CH_3-$ | H | $(CH_3)_2CH-$ | oil |
| 406 | $CH_3$ | $CH_3$ | 6-$CH_3$ | cyclohexyl | $CH_3-$ | H | $(CH_3)_3C-$ | 72 |
| 407 | $CH_3$ | $CH_3$ | 6-$CH_3$ | cyclohexyl | $CH_3-$ | H | $(CH_3)_2-CH-C(CH_3)_2-$ | |

TABLE 2-continued (Ib)
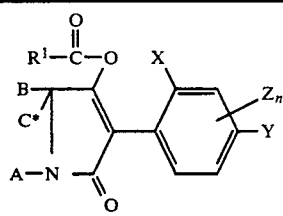

| Ex. No. | X | Y | $Z_n$ | A | B | C* | $R^1$ | mp °C. |
|---|---|---|---|---|---|---|---|---|
| 408 | $CH_3$ | $CH_3$ | 6-$CH_3$ | cyclohexyl | $CH_3-$ | H | $(CH_3)_3C-CH_2-$ | 118 |
| 409 | $CH_3$ | $CH_3$ | 6-$CH_3$ | cyclohexyl | $CH_3-$ | H | $CH_3O-CH_2-C(CH_3)_2-$ | |
| 410 | $CH_3$ | $CH_3$ | 6-$CH_3$ | cyclohexyl | $CH_3-$ | H | $ClCH_2-C(CH_3)_2-$ | 115 |
| 411 | $CH_3$ | $CH_3$ | 6-$CH_3$ | cyclohexyl | $CH_3-$ | H | $(CH_3OCH_2)_2C(CH_3)-$ | |
| 412 | $CH_3$ | $CH_3$ | 6-$CH_3$ | cyclohexyl | $CH_3-$ | H | $(CH_3)_2C=CH-$ | |
| 413 | $CH_3$ | $CH_3$ | 6-$CH_3$ | cyclohexyl | $CH_3-$ | H | 2-methyl-1,3-dioxan-2-yl | |
| 414 | $CH_3$ | $CH_3$ | 6-$CH_3$ | cyclohexyl | $C_2H_5-$ | H | $CH_3-$ | |
| 415 | $CH_3$ | $CH_3$ | 6-$CH_3$ | cyclohexyl | $C_2H_5-$ | H | $(CH_3)_2CH-$ | |
| 416 | $CH_3$ | $CH_3$ | 6-$CH_3$ | cyclohexyl | $C_2H_5-$ | H | $(CH_3)_3C-$ | |
| 417 | $CH_3$ | $CH_3$ | 6-$CH_3$ | cyclohexyl | $C_2H_5-$ | H | $(CH_3)_2CH-C(CH_3)_2-$ | |
| 418 | $CH_3$ | $CH_3$ | 6-$CH_3$ | cyclohexyl | $C_2H_5-$ | H | $(CH_3)_3C-CH_2-$ | |

TABLE 2-continued (Ib)
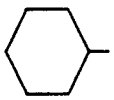

| Ex. No. | X | Y | $Z_n$ | A | B | C* | $R^1$ | mp °C. |
|---|---|---|---|---|---|---|---|---|
| 419 | $CH_3$ | $CH_3$ | 6-$CH_3$ | cyclohexyl | $C_2H_5-$ | H | $CH_3O-CH_2-C(CH_3)_2-$ | |
| 420 | $CH_3$ | $CH_3$ | 6-$CH_3$ | cyclohexyl | $C_2H_5-$ | H | $ClCH_2-C(CH_3)_2-$ | |
| 421 | $CH_3$ | $CH_3$ | 6-$CH_3$ | cyclohexyl | $C_2H_5-$ | H | 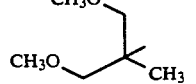 | |
| 422 | $CH_3$ | $CH_3$ | 6-$CH_3$ | cyclohexyl | $C_2H_5-$ | H | $(CH_3)_2C=CH-$ | |
| 423 | $CH_3$ | $CH_3$ | 6-$CH_3$ | cyclohexyl | $C_2H_5-$ | H | 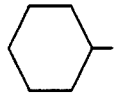 | |
| 424 | $CH_3$ | $CH_3$ | 6-$CH_3$ | cyclohexyl | $C_3H_7-$ | H | $CH_3-$ | |
| 425 | $CH_3$ | $CH_3$ | 6-$CH_3$ | cyclohexyl | $C_3H_7-$ | H | $(CH_3)_2CH-$ | |
| 426 | $CH_3$ | $CH_3$ | 6-$CH_3$ | cyclohexyl | $C_3H_7-$ | H | $(CH_3)_3C-$ | |
| 427 | $CH_3$ | $CH_3$ | 6-$CH_3$ | cyclohexyl | $C_3H_7-$ | H | $(CH_3)_2CH-C(CH_3)_2-$ | |
| 428 | $CH_3$ | $CH_3$ | 6-$CH_3$ | cyclohexyl | $(CH_3)_2CH-$ | H | $CH_3-$ | |
| 429 | $CH_3$ | $CH_3$ | 6-$CH_3$ | cyclohexyl | $(CH_3)_2CH-$ | H | $(CH_3)_2CH-$ | |

TABLE 2-continued

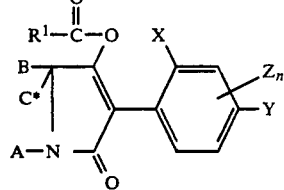
(Ib)

| Ex. No. | X | Y | $Z_n$ | A | B | C* | $R^1$ | mp °C. |
|---|---|---|---|---|---|---|---|---|
| 430 | $CH_3$ | $CH_3$ | 6-$CH_3$ | cyclohexyl | $(CH_3)_2CH-$ | H | $(CH_3)_3C-$ | |
| 431 | $CH_3$ | $CH_3$ | 6-$CH_3$ | cyclohexyl | $(CH_3)_2CH-$ | H | $(CH_3)_2CH-C(CH_3)_2-$ | |
| 432 | $CH_3$ | $CH_3$ | 6-$CH_3$ | cyclohexyl | $CH_3-$ | $CH_3-$ | $CH_3-$ | |
| 433 | $CH_3$ | $CH_3$ | 6-$CH_3$ | cyclohexyl | $CH_3-$ | $CH_3-$ | $(CH_3)_2CH-$ | |
| 434 | $CH_3$ | $CH_3$ | 6-$CH_3$ | cyclohexyl | $CH_3-$ | $CH_3-$ | $(CH_3)_3C-$ | |
| 435 | $CH_3$ | $CH_3$ | 6-$CH_3$ | cyclohexyl | $CH_3-$ | $CH_3-$ | $(CH_3)_2CH-C(CH_3)_2-$ | |
| 436 | $CH_3$ | $CH_3$ | 6-$CH_3$ | phenethyl | H | H | $CH_3-$ | oil |
| 437 | $CH_3$ | $CH_3$ | 6-$CH_3$ | phenethyl | H | H | $(CH_3)_2CH-$ | |
| 438 | $CH_3$ | $CH_3$ | 6-$CH_3$ | phenethyl | H | H | $(CH_3)_3C-$ | 104 |
| 439 | $CH_3$ | $CH_3$ | 6-$CH_3$ | phenethyl | H | H | $(CH_3)_2-CH-C(CH_3)_2-$ | |
| 440 | $CH_3$ | $CH_3$ | 6-$CH_3$ | $CH_3-O-CH_2-CH(CH_3)-$ | H | H | $CH_3-$ | 76 |
| 441 | $CH_3$ | $CH_3$ | 6-$CH_3$ | $CH_3-O-CH_2-CH(CH_3)-$ | H | H | $(CH_3)_2CH-$ | |
| 442 | $CH_3$ | $CH_3$ | 6-$CH_3$ | $CH_3-O-CH_2-CH(CH_3)-$ | H | H | $(CH_3)_3C-$ | oil |
| 443 | $CH_3$ | $CH_3$ | 6-$CH_3$ | $CH_3-O-CH_2-CH(CH_3)-$ | H | H | $(CH_3)_2CH-C(CH_3)_2-$ | |
| 444 | $CH_3$ | $CH_3$ | 6-$CH_3$ | $CH_3O-(CH_2)_2-$ | H | H | $CH_3-$ | oil |
| 445 | $CH_3$ | $CH_3$ | 6-$CH_3$ | $CH_3O-(CH_2)_2-$ | H | H | $(CH_3)_2CH-$ | oil |
| 446 | $CH_3$ | $CH_3$ | 6-$CH_3$ | $CH_3O-(CH_2)_2-$ | H | H | $(CH_3)_3C-$ | oil |
| 447 | $CH_3$ | $CH_3$ | 6-$CH_3$ | $CH_3O-(CH_2)_2-$ | H | H | $(CH_3)_2CH-C(CH_3)_2-$ | oil |
| 448 | $CH_3$ | $CH_3$ | 6-$CH_3$ | $CH_3O-(CH_2)_2-$ | $CH_3-$ | H | $CH_3-$ | oil |

TABLE 2-continued

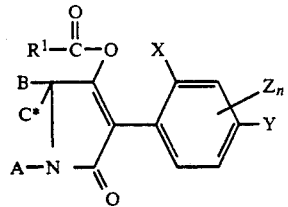

(Ib)

| Ex. No. | X | Y | $Z_n$ | A | B | C* | $R^1$ | mp °C. |
|---|---|---|---|---|---|---|---|---|
| 449 | $CH_3$ | $CH_3$ | 6-$CH_3$ | $CH_3O-(CH_2)_2-$ | $CH_3-$ | H | $(CH_3)_2CH-$ | oil |
| 450 | $CH_3$ | $CH_3$ | 6-$CH_3$ | $CH_3O-(CH_2)_2-$ | $CH_3-$ | H | $(CH_3)_3C-$ | oil |
| 451 | $CH_3$ | $CH_3$ | 6-$CH_3$ | $CH_3O-(CH_2)_2-$ | $CH_3-$ | H | $(CH_3)_2CH-C(CH_3)_2-$ | oil |
| 452 | $CH_3$ | $CH_3$ | 6-$CH_3$ | $CH_3O-(CH_2)_3-$ | H | H | $CH_3-$ | oil |
| 453 | $CH_3$ | $CH_3$ | 6-$CH_3$ | $CH_3O-(CH_2)_3-$ | H | H | $(CH_3)_2CH-$ | oil |
| 454 | $CH_3$ | $CH_3$ | 6-$CH_3$ | $CH_3O-(CH_2)_3-$ | H | H | $(CH_3)_3C-$ | oil |
| 455 | $CH_3$ | $CH_3$ | 6-$CH_3$ | $CH_3O-(CH_2)_3-$ | H | H | $(CH_3)_2CH-C(CH_3)_2-$ | oil |
| 455 | $CH_3$ | $CH_3$ | 6-$CH_3$ | $CH_3O-(CH_2)_3-$ | $CH_3-$ | H | $CH3-$ | oil |
| 457 | $CH_3$ | $CH_3$ | 6-$CH_3$ | $CH_3O-(CH_2)_3-$ | $CH_3-$ | H | $(CH_3)_2CH-$ | oil |
| 458 | $CH_3$ | $CH_3$ | 6-$CH_3$ | $CH_3O-(CH_2)_3-$ | $CH_3-$ | H | $(CH_3)_3C-$ | oil |
| 459 | $CH_3$ | $CH_3$ | 6-$CH_3$ | $CH_3O-(CH_2)_3-$ | $CH_3-$ | H | $(CH_3)_2CH-C(CH_3)_2-$ | oil |
| 460 | $CH_3$ | $CH_3$ | 6-$CH_3$ | $C_2H_5O-(CH_2)_2-CH(CH_3)-$ | H | H | $CH_3-$ | oil |
| 461 | $CH_3$ | $CH_3$ | 6-$CH_3$ | $C_2H_5O-(CH_2)_2-CH(CH_3)-$ | H | H | $(CH_3)_2CH-$ | oil |
| 462 | $CH_3$ | $CH_3$ | 6-$CH_3$ | $C_2H_5O-(CH_2)_2-CH(CH_3)-$ | H | H | $(CH_3)_3C-$ | oil |
| 463 | $CH_3$ | $CH_3$ | 6-$CH_3$ | $C_2H_5O-(CH_2)_2-CH(CH_3)-$ | H | H | $(CH_3)_2CH-C(CH_3)_2-$ | oil |
| 464 | $CH_3$ | $CH_3$ | 6-$CH_3$ | $CH_3O-CH_2-CH(CH_3)-CH-$ | H | H | $CH_3-$ | oil |
| 465 | $CH_3$ | $CH_3$ | 6-$CH_3$ | $CH_3O-CH_2-CH(CH_3)-CH-$ | H | H | $(CH_3)_2CH-$ | oil |
| 466 | $CH_3$ | $CH_3$ | 6-$CH_3$ | $CH_3O-CH_2-CH(CH_3)-CH-$ | H | H | $(CH_3)_3C-$ | oil |
| 467 | $CH_3$ | $CH_3$ | 6-$CH_3$ | $CH_3O-CH_2-CH(CH_3)-CH-$ | H | H | $(CH_3)_2CH-C(CH_3)_2-$ | oil |
| 468 | $CH_3$ | $CH_3$ | 6-$CH_3$ | $C_2H_5-S-(CH_2)_2-$ | H | H | $CH_3-$ | oil |
| 469 | $CH_3$ | $CH_3$ | 6-$CH_3$ | $C_2H_5-S-(CH_2)_2-$ | H | H | $(CH_3)_2CH-$ | oil |
| 470 | $CH_3$ | $CH_3$ | 6-$CH_3$ | $C_2H_5-S-(CH_2)_2-$ | H | H | $(CH_3)_3C-$ | oil |
| 471 | $CH_3$ | $CH_3$ | 6-$CH_3$ | $C_2H_5-S-(CH_2)_2-$ | H | H | $(CH_3)_2CH-C(CH_3)_2-$ | oil |

TABLE 3

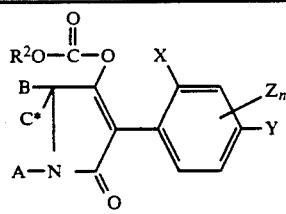

(Ic)

| Ex. No. | X | Y | $Z_n$ | A | B | C* | $R^1$ | mp °C. |
|---|---|---|---|---|---|---|---|---|
| 472 | $CH_3$ | $CH_3$ | 5-$CH_3$ | $CH_3-$ | H | H | $CH_3-$ | |
| 473 | $CH_3$ | $CH_3$ | 6-$CH_3$ | $CH_3-$ | H | H | $C_2H_5-$ | |
| 474 | $CH_3$ | $CH_3$ | 6-$CH_3$ | $CH_3-$ | H | H | $(CH_3)_2CH-$ | |
| 475 | $CH_3$ | $CH_3$ | 6-$CH_3$ | $CH_3-$ | H | H | $(CH_3)_2CH-CH_2-$ | |
| 476 | $CH_3$ | $CH_3$ | 6-$CH_3$ | $CH_3-$ | H | H | $\begin{matrix}C_2H_5\\ \phantom{xx}CH-\\ CH_3\end{matrix}$ | |
| 477 | $CH_3$ | $CH_3$ | 6-$CH_3$ | $CH_3-$ | H | H | $(CH_3)_3C-CH_2-$ | |
| 478 | $CH_3$ | $CH_3$ | 6-$CH_3$ | $CH_3-$ | H | H | cyclohexyl | |
| 479 | $CH_3$ | $CH_3$ | 6-$CH_3$ | $CH_3-$ | H | H | phenyl | |
| 480 | $CH_3$ | $CH_3$ | 6-$CH_3$ | $CH_3-$ | $CH_3-$ | H | $CH_3-$ | |
| 481 | $CH_3$ | $CH_3$ | 6-$CH_3$ | $CH_3-$ | $CH_3-$ | H | $C_2H_5-$ | oil |
| 482 | $CH_3$ | $CH_3$ | 6-$CH_3$ | $CH_3-$ | $CH_3-$ | H | $(CH_3)_2CH-$ | oil |
| 483 | $CH_3$ | $CH_3$ | 6-$CH_3$ | $CH_3-$ | $CH_3-$ | H | $(CH_3)_2CH-CH_2-$ | oil |

TABLE 3-continued (Ic)

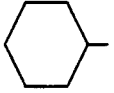

| Ex. No. | X | Y | $Z_n$ | A | B | C* | $R^1$ | mp °C. |
|---|---|---|---|---|---|---|---|---|
| 484 | $CH_3$ | $CH_3$ | 6-$CH_3$ | $CH_3-$ | $CH_3-$ | H | $CH(C_2H_5)CH_3$ | oil |
| 485 | $CH_3$ | $CH_3$ | 6-$CH_3$ | $CH_3-$ | $CH_3-$ | H | $(CH_3)_3C-CH_2-$ | 146 |
| 486 | $CH_3$ | $CH_3$ | 6-$CH_3$ | $CH_3-$ | $CH_3-$ | H | cyclohexyl | |
| 487 | $CH_3$ | $CH_3$ | 6-$CH_3$ | $CH_3-$ | $CH_3-$ | H | phenyl | |
| 488 | $CH_3$ | $CH_3$ | 6-$CH_3$ | $CH_3-$ | $C_2H_5-$ | H | $CH_3-$ | |
| 489 | $CH_3$ | $CH_3$ | 6-$CH_3$ | $CH_3-$ | $C_2H_5-$ | H | $C_2H_5-$ | |
| 490 | $CH_3$ | $CH_3$ | 6-$CH_3$ | $CH_3-$ | $C_2H_5-$ | H | $(CH_3)_2CH-$ | |
| 491 | $CH_3$ | $CH_3$ | 6-$CH_3$ | $CH_3-$ | $C_2H_5-$ | H | $(CH_3)_2CH-CH_2-$ | |
| 492 | $CH_3$ | $CH_3$ | 6-$CH_3$ | $CH_3-$ | $C_2H_5-$ | H | $CH(C_2H_5)CH_3$ | |
| 493 | $CH_3$ | $CH_3$ | 6-$CH_3$ | $CH_3-$ | $C_2H_5-$ | H | $(CH_3)_3C-CH_2-$ | |
| 494 | $CH_3$ | $CH_3$ | 6-$CH_3$ | $CH_3-$ | $C_2H_5-$ | H | cyclohexyl | |
| 495 | $CH_3$ | $CH_3$ | 6-$CH_3$ | $CH_3-$ | $C_2H_5-$ | H | phenyl | |
| 496 | $CH_3$ | $CH_3$ | 6-$CH_3$ | $CH_3-$ | $C_3H_7-$ | H | $C_2H_5-$ | |
| 497 | $CH_3$ | $CH_3$ | 6-$CH_3$ | $CH_3-$ | $C_3H_7-$ | H | $(CH_3)_2CH-$ | |
| 498 | $CH_3$ | $CH_3$ | 6-$CH_3$ | $CH_3-$ | $C_3H_7-$ | H | $(CH_3)_2CH-CH_2-$ | |
| 499 | $CH_3$ | $CH_3$ | 6-$CH_3$ | $CH_3-$ | $C_3H_7-$ | H | $CH(CH_3)C_2H_5$ | |
| 500 | $CH_3$ | $CH_3$ | 6-$CH_3$ | $CH_3-$ | $(CH_3)_2CH-$ | H | $(CH_3)_3C-CH_2-$ | |
| 501 | $CH_3$ | $CH_3$ | 6-$CH_3$ | $CH_3-$ | $(CH_3)_2CH-$ | H | $C_2H_5-$ | |
| 502 | $CH_3$ | $CH_3$ | 6-$CH_3$ | $CH_3-$ | $(CH_3)_2CH-$ | H | $(CH_3)_2CH-$ | |
| 503 | $CH_3$ | $CH_3$ | 6-$CH_3$ | $CH_3-$ | $(CH_3)_2CH-$ | H | $(CH_3)_2CH-CH_2-$ | |
| 504 | $CH_3$ | $CH_3$ | 6-$CH_3$ | $CH_3-$ | $(CH_3)_2CH-$ | H | $CH(CH_3)C_2H_5$ | |
| 505 | $CH_3$ | $CH_3$ | 6-$CH_3$ | $CH_3-$ | $(CH_3)_2CH-$ | H | $(CH_3)_3C-CH_2-$ | |
| 506 | $CH_3$ | $CH_3$ | 6-$CH_3$ | $C_2H_5-$ | H | H | $CH_3-$ | |
| 507 | $CH_3$ | $CH_3$ | 6-$CH_3$ | $C_2H_5-$ | H | H | $C_2H_5-$ | |

TABLE 3-continued (Ic)

Structure: $R^2O-C(=O)-O-$ attached to a vinyl group with substituents B and C*, where C* also bears A-N and a carbonyl (C=O); the vinyl is connected to a phenyl ring bearing X, Y, and $Z_n$ substituents.

| Ex. No. | X | Y | $Z_n$ | A | B | C* | $R^1$ | mp °C. |
|---|---|---|---|---|---|---|---|---|
| 508 | CH$_3$ | CH$_3$ | 6-CH$_3$ | C$_2$H$_5$— | H | H | (CH$_3$)$_2$CH— | oil |
| 509 | CH$_3$ | CH$_3$ | 6-CH$_3$ | C$_2$H$_5$— | H | H | (CH$_3$)$_2$CH—CH$_2$— | |
| 510 | CH$_3$ | CH$_3$ | 6-CH$_3$ | C$_2$H$_5$— | H | H | C$_2$H$_5$(CH$_3$)CH— | |
| 511 | CH$_3$ | CH$_3$ | 6-CH$_3$ | C$_2$H$_5$— | H | H | (CH$_3$)$_3$C—CH$_2$— | |
| 512 | CH$_3$ | CH$_3$ | 6-CH$_3$ | C$_2$H$_5$— | H | H | cyclohexyl | |
| 513 | CH$_3$ | CH$_3$ | 6-CH$_3$ | C$_2$H$_5$— | H | H | phenyl | |
| 514 | CH$_3$ | CH$_3$ | 6-CH$_3$ | C$_2$H$_5$— | CH$_3$— | H | CH$_3$— | |
| 515 | CH$_3$ | CH$_3$ | 6-CH$_3$ | C$_2$H$_5$— | CH$_3$ | H | C$_2$H$_5$— | oil |
| 516 | CH$_3$ | CH$_3$ | 6-CH$_3$ | C$_2$H$_5$— | CH$_3$ | H | (CH$_3$)$_2$CH— | |
| 517 | CH$_3$ | CH$_3$ | 6-CH$_3$ | C$_2$H$_5$— | CH$_3$— | H | (CH$_3$)$_2$CH—CH$_2$— | |
| 518 | CH$_3$ | CH$_3$ | 6-CH$_3$ | C$_2$H$_5$— | CH$_3$— | H | C$_2$H$_5$(CH$_3$)CH— | |
| 519 | CH$_3$ | CH$_3$ | 6-CH$_3$ | C$_2$H$_5$— | CH$_3$— | H | (CH$_3$)$_3$C—CH$_2$— | |
| 520 | CH$_3$ | CH$_3$ | 6-CH$_3$ | C$_2$H$_5$— | CH$_3$— | H | cyclohexyl | |
| 521 | CH$_3$ | CH$_3$ | 6-CH$_3$ | C$_2$H$_5$— | CH$_3$— | H | phenyl | |
| 522 | CH$_3$ | CH$_3$ | 6-CH$_3$ | C$_2$H$_5$— | C$_2$H$_5$— | H | CH$_3$— | |
| 523 | CH$_3$ | CH$_3$ | 6-CH$_3$ | C$_2$H$_5$— | C$_2$H$_5$— | H | C$_2$H$_5$— | |
| 524 | CH$_3$ | CH$_3$ | 6-CH$_3$ | C$_2$H$_5$— | C$_2$H$_5$— | H | (CH$_3$)$_2$CH— | |
| 525 | CH$_3$ | CH$_3$ | 6-CH$_3$ | C$_2$H$_5$— | C$_2$H$_5$— | H | (CH$_3$)$_2$CH—CH$_2$— | |
| 526 | CH$_3$ | CH$_3$ | 6-CH$_3$ | C$_2$H$_5$— | C$_2$H$_5$— | H | C$_2$H$_5$(CH$_3$)CH— | |
| 527 | CH$_3$ | CH$_3$ | 6-CH$_3$ | C$_2$H$_5$— | C$_2$H$_5$— | H | (CH$_3$)$_3$C—CH$_2$— | |
| 528 | CH$_3$ | CH$_3$ | 6-CH$_3$ | C$_2$H$_5$— | C$_2$H$_5$— | H | cyclohexyl | |

TABLE 3-continued

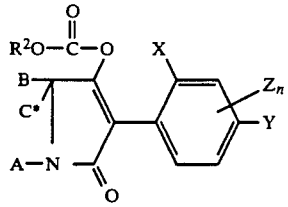
(Ic)

| Ex. No. | X | Y | $Z_n$ | A | B | C* | $R^1$ | mp °C. |
|---|---|---|---|---|---|---|---|---|
| 529 | $CH_3$ | $CH_3$ | 6-$CH_3$ | $C_2H_5-$ | $C_2H_5-$ | H | ⬡ | |
| 530 | $CH_3$ | $CH_3$ | 6-$CH_3$ | $C_2H_5-$ | $C_3H_7-$ | H | $C_2H_5-$ | |
| 531 | $CH_3$ | $CH_3$ | 6-$CH_3$ | $C_2H_5-$ | $C_3H_5-$ | H | $(CH_3)_2CH-$ | |
| 532 | $CH_3$ | $CH_3$ | 6-$CH_3$ | $C_2H_5-$ | $C_3H_7-$ | H | $(CH_3)_2CH-CH_2-$ | |
| 533 | $CH_3$ | $CH_3$ | 6-$CH_3$ | $C_2H_5-$ | $C_3H_7-$ | H | $CH_3$<br>   \\<br>    CH—<br>   /<br>$C_2H_5$ | |
| 534 | $CH_3$ | $CH_3$ | 6-$CH_3$ | $C_2H_5-$ | $(CH_3)_2CH-$ | H | $(CH_3)_3C-CH_2-$ | |
| 535 | $CH_3$ | $CH_3$ | 6-$CH_3$ | $C_2H_5-$ | $(CH_3)_2CH-$ | H | $C_2H_5-$ | |
| 536 | $CH_3$ | $CH_3$ | 6-$CH_3$ | $C_2H_5-$ | $(CH_3)_2CH-$ | H | $(CH_3)_2CH-$ | |
| 537 | $CH_3$ | $CH_3$ | 6-$CH_3$ | $C_2H_5-$ | $(CH_3)_2CH-$ | H | $(CH_3)_2CH-CH_2-$ | |
| 538 | $CH_3$ | $CH_3$ | 6-$CH_3$ | $C_2H_5-$ | $(CH_3)_2CH-$ | H | $CH_3$<br>   \\<br>    CH—<br>   /<br>$C_2H_5$ | |
| 539 | $CH_3$ | $CH_3$ | 6-$CH_3$ | $C_2H_5-$ | $(CH_3)_2CH-$ | H | $(CH_3)_3C-CH_2-$ | |
| 540 | $CH_3$ | $CH_3$ | 6-$CH_3$ | $C_3H_7-$ | H | H | $CH_3-$ | |
| 541 | $CH_3$ | $CH_3$ | 6-$CH_3$ | $C_3H_7-$ | H | H | $C_2H_5-$ | |
| 542 | $CH_3$ | $CH_3$ | 6-$CH_3$ | $C_3H_7-$ | H | H | $(CH_3)_2CH-$ | |
| 543 | $CH_3$ | $CH_3$ | 6-$CH_3$ | $C_3H_7-$ | H | H | $(CH_3)_2CH-CH_2-$ | |
| 544 | $CH_3$ | $CH_3$ | 6-$CH_3$ | $C_3H_7-$ | H | H | $C_2H_5$<br>   \\<br>    CH—<br>   /<br>$CH_3$ | |
| 545 | $CH_3$ | $CH_3$ | 6-$CH_3$ | $C_3H_7-$ | H | H | $(CH_3)_3C-CH_2-$ | |
| 546 | $CH_3$ | $CH_3$ | 6-$CH_3$ | $C_3H_7-$ | H | H | ⬡ (cyclohexyl) | |
| 547 | $CH_3$ | $CH_3$ | 6-$CH_3$ | $C_3H_7-$ | H | H | ⬡ (phenyl) | |
| 548 | $CH_3$ | $CH_3$ | 6-$CH_3$ | $C_3H_7-$ | $CH_3-$ | H | $CH_3-$ | |
| 549 | $CH_3$ | $CH_3$ | 6-$CH_3$ | $C_3H_7-$ | $CH_3-$ | H | $C_2H_5-$ | |
| 550 | $CH_3$ | $CH_3$ | 6-$CH_3$ | $C_3H_7-$ | $CH_3-$ | H | $(CH_3)_2CH-$ | |
| 551 | $CH_3$ | $CH_3$ | 6-$CH_3$ | $C_3H_7-$ | $CH_3-$ | H | $(CH_3)_2CH-CH_2-$ | |
| 552 | $CH_3$ | $CH_3$ | 6-$CH_3$ | $C_3H_7-$ | $CH_3-$ | H | $C_2H_5$<br>   \\<br>    CH—<br>   /<br>$CH_3$ | |
| 553 | $CH_3$ | $CH_3$ | 6-$CH_3$ | $C_3H_7-$ | $CH_3-$ | H | $(CH_3)_3C-CH_2-$ | |

TABLE 3-continued (Ic)
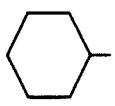

| Ex. No. | X | Y | $Z_n$ | A | B | C* | $R^1$ | mp °C. |
|---|---|---|---|---|---|---|---|---|
| 554 | $CH_3$ | $CH_3$ | 6-$CH_3$ | $C_2H_5-$ | $CH_3-$ | H | 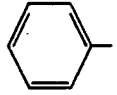 | |
| 555 | $CH_3$ | $CH_3$ | 6-$CH_3$ | $C_2H_5-$ | $CH_3-$ | H | 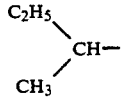 | |
| 556 | $CH_3$ | $CH_3$ | 6-$CH_3$ | $C_3H_7-$ | $C_2H_5$ | H | $CH_3-$ | |
| 557 | $CH_3$ | $CH_3$ | 6-$CH_3$ | $C_3H_7-$ | $C_2H_5-$ | H | $C_2H_5-$ | |
| 558 | $CH_3$ | $CH_3$ | 6-$CH_3$ | $C_3H_7-$ | $C_2H_5-$ | H | $(CH_3)_2CH-$ | |
| 559 | $CH_3$ | $CH_3$ | 6-$CH_3$ | $C_3H_7-$ | $C_2H_5-$ | H | $(CH_3)_2CH-CH_2-$ | |
| 560 | $CH_3$ | $CH_3$ | 6-$CH_3$ | $C_3H_7-$ | $C_2H_5-$ | H |  | |
| 561 | $CH_3$ | $CH_3$ | 6-$CH_3$ | $C_3H_7-$ | $C_2H_5-$ | H | $(CH_3)_3C-CH_2-$ | |
| 562 | $CH_3$ | $CH_3$ | 6-$CH_3$ | $C_3H_7-$ | $C_2H_5-$ | H |  | |
| 563 | $CH_3$ | $CH_3$ | 6-$CH_3$ | $C_3H_7-$ | $C_2H_5-$ | H | 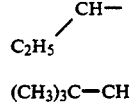 | |
| 564 | $CH_3$ | $CH_3$ | 6-$CH_3$ | $C_3H_7-$ | $C_3H_7-$ | H | $C_2H_5-$ | |
| 565 | $CH_3$ | $CH_3$ | 6-$CH_3$ | $C_3H_7-$ | $C_3H_7-$ | H | $(CH_3)_2CH-$ | |
| 566 | $CH_3$ | $CH_3$ | 6-$CH_3$ | $C_3H_7-$ | $C_3H_7-$ | H | $(CH_3)_2CH-CH_2-$ | |
| 567 | $CH_3$ | $CH_3$ | 6-$CH_3$ | $C_3H_7-$ | $C_3H_7-$ | H | 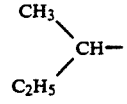 | |
| 568 | $CH_3$ | $CH_3$ | 6-$CH_3$ | $C_3H_7-$ | $C_3H_7-$ | H | $(CH_3)_3C-CH_2-$ | |
| 569 | $CH_3$ | $CH_3$ | 6-$CH_3$ | $C_3H_7-$ | $(CH_3)_2CH-$ | H | $C_2H_5-$ | |
| 570 | $CH_3$ | $CH_3$ | 6-$CH_3$ | $C_3H_7-$ | $(CH_3)_2CH-$ | H | $(CH_3)_2CH-$ | |
| 571 | $CH_3$ | $CH_3$ | 6-$CH_3$ | $C_3H_7-$ | $(CH_3)_2CH-$ | H | $(CH_3)_2CH-CH_2-$ | |
| 572 | $CH_3$ | $CH_3$ | 6-$CH_3$ | $C_3H_7-$ | $(CH_3)_2CH-$ | H | 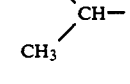 | |
| 573 | $CH_3$ | $CH_3$ | 6-$CH_3$ | $C_3H_7-$ | $(CH_3)_2CH-$ | H | $(CH_3)_3C-CH_2-$ | |
| 574 | $CH_3$ | $CH_3$ | 6-$CH_3$ | $(CH_3)_2CH-$ | H | H | $CH_3-$ | 67 |
| 575 | $CH_3$ | $CH_3$ | 6-$CH_3$ | $(CH_3)_2CH-$ | H | H | $C_2H_5-$ | 87 |
| 576 | $CH_3$ | $CH_3$ | 6-$CH_3$ | $(CH_3)_2CH-$ | H | H | $(CH_3)_2CH-CH_2$ | 41 |
| 577 | $CH_3$ | $CH_3$ | 6-$CH_3$ | $(CH_3)_2CH-$ | H | H | $\begin{array}{c}C_2H_5\\ \phantom{C_2H_5}\diagdown\\ CH- \\ \diagup\\ CH_3\end{array}$ | 83 |
| 578 | $CH_3$ | $CH_3$ | 6-$CH_3$ | $(CH_3)_2CH-$ | H | H | $(CH_3)_3C-CH_2-$ | oil |

TABLE 3-continued

(Ic)

| Ex. No. | X | Y | $Z_n$ | A | B | C* | $R^1$ | mp °C. |
|---|---|---|---|---|---|---|---|---|
| 579 | $CH_3$ | $CH_3$ | 6-$CH_3$ | $(CH_3)_2CH-$ | H | H |  | |
| 580 | $CH_3$ | $CH_3$ | 6-$CH_3$ | $(CH_3)_2CH-$ | $CH_3-$ | H | $CH_3-$ | |
| 581 | $CH_3$ | $CH_3$ | 6-$CH_3$ | $(CH_3)_2CH-$ | $CH_3-$ | H | $C_2H_5-$ | |
| 582 | $CH_3$ | $CH_3$ | 6-$CH_3$ | $(CH_3)_2CH-$ | $CH_3-$ | H | $(CH_3)_2CH-$ | |
| 583 | $CH_3$ | $CH_3$ | 6-$CH_3$ | $(CH_3)_2CH-$ | $CH_3-$ | H | $(CH_3)_2CH-CH_2-$ | |
| 584 | $CH_3$ | $CH_3$ | 6-$CH_3$ | $(CH_3)_2CH-$ | $CH_3-$ | H | $\begin{array}{c}C_2H_5\\ \diagdown\\ CH-\\ \diagup\\ CH_3\end{array}$ | |
| 585 | $CH_3$ | $CH_3$ | 6-$CH_3$ | $(CH_3)_2CH-$ | $CH_3-$ | H | $(CH_3)_3C-CH_2-$ | 83 |
| 586 | $CH_3$ | $CH_3$ | 6-$CH_3$ | $(CH_3)_2CH-$ | $CH_3-$ | H |  | |
| 587 | $CH_3$ | $CH_3$ | 6-$CH_3$ | $(CH_3)_2CH-$ | $CH_3-$ | H |  | |
| 588 | $CH_3$ | $CH_3$ | 6-$CH_3$ | $(CH_3)_2CH-$ | $C_2H_5-$ | H | $CH_3-$ | |
| 589 | $CH_3$ | $CH_3$ | 6-$CH_3$ | $(CH_3)_2CH-$ | $C_2H_5-$ | H | $C_2H_5-$ | |
| 590 | $CH_3$ | $CH_3$ | 6-$CH_3$ | $(CH_3)_2CH-$ | $C_2H_5-$ | H | $(CH_3)_2CH-$ | |
| 591 | $CH_3$ | $CH_3$ | 6-$CH_3$ | $(CH_3)_2CH-$ | $C_2H_5-$ | H | $(CH_3)_2CH-CH_2-$ | |
| 592 | $CH_3$ | $CH_3$ | 6-$CH_3$ | $(CH_3)_2CH-$ | $C_2H_5-$ | H | $\begin{array}{c}C_2H_5\\ \diagdown\\ CH-\\ \diagup\\ CH_3\end{array}$ | |
| 593 | $CH_3$ | $CH_3$ | 6-$CH_3$ | $(CH_3)_2CH-$ | $C_2H_5-$ | H | $(CH_3)_3C-CH_2-$ | |
| 594 | $CH_3$ | $CH_3$ | 6-$CH_3$ | $(CH_3)_2CH-$ | $C_2H_5-$ | H |  | |
| 595 | $CH_3$ | $CH_3$ | 6-$CH_3$ | $(CH_3)_2CH-$ | $C_2H_5-$ | H |  | |
| 596 | $CH_3$ | $CH_3$ | 6-$CH_3$ | $(CH_3)_2CH-$ | $C_3H_7-$ | H | $C_2H_5-$ | |
| 597 | $CH_3$ | $CH_3$ | 6-$CH_3$ | $(CH_3)_2CH-$ | $C_3H_7-$ | H | $(CH_3)_2CH-$ | |
| 598 | $CH_3$ | $CH_3$ | 6-$CH_3$ | $(CH_3)_2CH-$ | $C_3H_7-$ | H | $(CH_3)_2CH-CH_2-$ | |
| 599 | $CH_3$ | $CH_3$ | 6-$CH_3$ | $(CH_3)_2CH-$ | $C_3H_7-$ | H | $\begin{array}{c}CH_3\\ \diagdown\\ CH-\\ \diagup\\ C_2H_5\end{array}$ | |
| 600 | $CH_3$ | $CH_3$ | 6-$CH_3$ | $(CH_3)_2CH-$ | $C_3H_7-$ | H | $(CH_3)_3C-CH_2-$ | |
| 601 | $CH_3$ | $CH_3$ | 6-$CH_3$ | $(CH_3)_2CH-$ | $(CH_3)_2CH-$ | H | $C_2H_5-$ | |
| 602 | $CH_3$ | $CH_3$ | 6-$CH_3$ | $(CH_3)_2CH-$ | $(CH_3)_2CH-$ | H | $(CH_3)_2CH-$ | |

TABLE 3-continued $$\text{(Ic)}$$

Structure: R²O-C(=O)-O-C(B)=C(-C(=O)-N-A)-[aryl with X, Y, Z_n]; C* on B carbon.

| Ex. No. | X | Y | $Z_n$ | A | B | C* | $R^1$ | mp °C. |
|---|---|---|---|---|---|---|---|---|
| 603 | CH₃ | CH₃ | 6-CH₃ | (CH₃)₂CH— | (CH₃)₂CH— | H | (CH₃)₂CH—CH₂— | |
| 604 | CH₃ | CH₃ | 6-CH₃ | (CH₃)₂CH— | (CH₃)₂CH— | H | CH₃\CH—/C₂H₅ | |
| 605 | CH₃ | CH₃ | 6-CH₃ | (CH₃)₂CH— | (CH₃)₂CH— | H | (CH₃)₃C—CH₂— | |
| 606 | CH₃ | CH₃ | 6-CH₃ | C₄H₉— | H | H | C₂H₅— | |
| 607 | CH₃ | CH₃ | 6-CH₃ | C₄H₉— | H | H | (CH₃)₂CH— | |
| 608 | CH₃ | CH₃ | 6-CH₃ | C₄H₉— | H | H | (CH₃)₂CH—CH₂— | |
| 609 | CH₃ | CH₃ | 6-CH₃ | C₄H₉— | H | H | CH₃\CH—/C₂H₅ | |
| 610 | CH₃ | CH₃ | 6-CH₃ | C₄H₉— | H | H | (CH₃)₃C—CH₂— | |
| 611 | CH₃ | CH₃ | 6-CH₃ | C₄H₉— | CH₃— | H | C₂H₅— | |
| 612 | CH₃ | CH₃ | 6-CH₃ | C₄H₉— | CH₃— | H | (CH₃)₂CH— | |
| 613 | CH₃ | CH₃ | 6-CH₃ | C₄H₉— | CH₃— | H | (CH₃)₂CH—CH₂— | |
| 614 | CH₃ | CH₃ | 6-CH₃ | C₄H₉— | CH₃— | H | CH₃\CH—/C₂H₅ | |
| 615 | CH₃ | CH₃ | 6-CH₃ | C₄H₉— | CH₃— | H | (CH₃)₃C—CH₂— | |
| 616 | CH₃ | CH₃ | 6-CH₃ | (CH₃)₂CH—CH₂— | H | H | C₂H₅— | |
| 617 | CH₃ | CH₃ | 6-CH₃ | (CH₃)₂CH—CH₂— | H | H | (CH₃)₂CH— | |
| 618 | CH₃ | CH₃ | 6-CH₃ | (CH₃)₂CH—CH₂— | H | H | (CH₃)₂CH—CH₂— | |
| 619 | CH₃ | CH₃ | 6-CH₃ | (CH₃)₂CH—CH₂— | H | H | CH₃\CH—/C₂H₅ | |
| 620 | CH₃ | CH₃ | 6-CH₃ | (CH₃)₂CH—CH₂— | H | H | (CH₃)₃C—CH₂— | |
| 621 | CH₃ | CH₃ | 6-CH₃ | (CH₃)₂CH—CH₂— | CH₃— | H | C₂H₅— | |
| 622 | CH₃ | CH₃ | 6-CH₃ | (CH₃)₂CH—CH₂— | CH₃— | H | (CH₃)₂CH— | |
| 623 | CH₃ | CH₃ | 6-CH₃ | (CH₃)₂CH—CH₂— | CH₃— | H | (CH₃)₂CH—CH₂— | |
| 624 | CH₃ | CH₃ | 6-CH₃ | (CH₃)₂CH—CH₂— | CH₃— | H | CH₃\CH—/C₂H₅ | |
| 625 | CH₃ | CH₃ | 6-CH₃ | (CH₃)₂CH—CH₂— | CH₃— | H | (CH₃)₂CH—CH₂— | |
| 626 | CH₃ | CH₃ | 6-CH₃ | C₂H₅\CH—/CH₃ | H | H | C₂H₅— | |
| 627 | CH₃ | CH₃ | 6-CH₃ | C₂H₅\CH—/CH₃ | H | H | (CH₃)₂CH— | |
| 628 | CH₃ | CH₃ | 6-CH₃ | C₂H₅\CH—/CH₃ | H | H | (CH₃)₂CH—CH₂— | |

TABLE 3-continued (Ic)

| Ex. No. | X | Y | $Z_n$ | A | B | C* | $R^1$ | mp °C. |
|---|---|---|---|---|---|---|---|---|
| 629 | $CH_3$ | $CH_3$ | 6-$CH_3$ | $\begin{array}{c}C_2H_5\\ \diagdown\\ CH-\\ \diagup\\ CH_3\end{array}$ | H | H | $\begin{array}{c}CH_3\\ \diagdown\\ CH-\\ \diagup\\ C_2H_5\end{array}$ | |
| 630 | $CH_3$ | $CH_3$ | 6-$CH_3$ | $\begin{array}{c}C_2H_5\\ \diagdown\\ CH-\\ \diagup\\ CH_3\end{array}$ | H | H | $(CH_3)_3C-CH_2-$ | |
| 631 | $CH_3$ | $CH_3$ | 6-$CH_3$ | $\begin{array}{c}C_2H_5\\ \diagdown\\ CH-\\ \diagup\\ CH_3\end{array}$ | $CH_3-$ | H | $C_2H_5-$ | |
| 632 | $CH_3$ | $CH_3$ | 6-$CH_3$ | $\begin{array}{c}C_2H_5\\ \diagdown\\ CH-\\ \diagup\\ CH_3\end{array}$ | $CH_3-$ | H | $(CH_3)_2CH-$ | |
| 633 | $CH_3$ | $CH_3$ | 6-$CH_3$ | $\begin{array}{c}C_2H_5\\ \diagdown\\ CH-\\ \diagup\\ CH_3\end{array}$ | $CH_3-$ | H | $(CH_3)_2CH-CH_2-$ | |
| 634 | $CH_3$ | $CH_3$ | 6-$CH_3$ | $\begin{array}{c}C_2H_5\\ \diagdown\\ CH-\\ \diagup\\ CH_3\end{array}$ | $CH_3-$ | H | $\begin{array}{c}CH_3\\ \diagdown\\ CH-\\ \diagup\\ C_2H_5\end{array}$ | |
| 635 | $CH_3$ | $CH_3$ | 6-$CH_3$ | $\begin{array}{c}C_2H_5\\ \diagdown\\ CH-\\ \diagup\\ CH_3\end{array}$ | $CH_3-$ | H | $(CH_3)_3C-CH_2-$ | |
| 636 | $CH_3$ | $CH_3$ | 6-$CH_3$ | $CH_2=CH-CH_2-$ | H | H | $C_2H_5-$ | |
| 637 | $CH_3$ | $CH_3$ | 6-$CH_3$ | $CH_2=CH-CH_2-$ | H | H | $(CH_3)_2CH-$ | oil |
| 638 | $CH_3$ | $CH_3$ | 6-$CH_3$ | $CH_2=CH-CH_2-$ | H | H | $(CH_3)_2CH-CH_2-$ | |
| 639 | $CH_3$ | $CH_3$ | 6-$CH_3$ | $CH_2=CH-CH_2-$ | H | H | $\begin{array}{c}CH_3\\ \diagdown\\ CH-\\ \diagup\\ C_2H_5\end{array}$ | |
| 640 | $CH_3$ | $CH_3$ | 6-$CH_3$ | $CH_2=CH-CH_2-$ | H | H | $(CH_3)_3C-CH_2-$ | |
| 641 | $CH_3$ | $CH_3$ | 6-$CH_3$ | $C_6H_5-CH_2-CH_2-$ | H | H | $C_2H_5-$ | |
| 642 | $CH_3$ | $CH_3$ | 6-$CH_3$ | $C_6H_5-CH_2-CH_2-$ | H | H | $(CH_3)_2CH-$ | oil |

TABLE 3-continued (Ic)

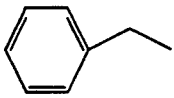

| Ex. No. | X | Y | $Z_n$ | A | B | C* | $R^1$ | mp °C. |
|---|---|---|---|---|---|---|---|---|
| 643 | CH$_3$ | CH$_3$ | 6-CH$_3$ | 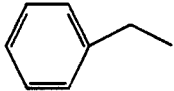 | H | H | (CH$_3$)$_2$CH—CH$_2$— | |
| 644 | CH$_3$ | CH$_3$ | 6-CH$_3$ | 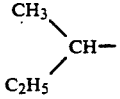 | H | H | CH$_3$<br>CH—<br>C$_2$H$_5$ | |
| 645 | CH$_3$ | CH$_3$ | 6-CH$_3$ | 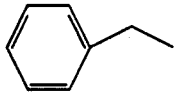 | H | H | (CH$_3$)$_3$C—CH$_2$— | |
| 646 | CH$_3$ | CH$_3$ | 6-CH$_3$ |  | H | H | CH$_3$— | |
| 647 | CH$_3$ | CH$_3$ | 6-CH$_3$ |  | H | H | C$_2$H$_5$— | |
| 648 | CH$_3$ | CH$_3$ | 6-CH$_3$ |  | H | H | (CH$_3$)$_2$CH— | |
| 649 | CH$_3$ | CH$_3$ | 6-CH$_3$ |  | H | H | (CH$_3$)$_2$CH—CH$_2$— | |
| 650 | CH$_3$ | CH$_3$ | 6-CH$_3$ |  | H | H | C$_2$H$_5$<br>CH—<br>CH$_3$ | oil |
| 651 | CH$_3$ | CH$_3$ | 6-CH$_3$ | 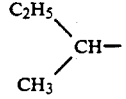 | H | H | (CH$_3$)$_3$C—CH$_2$— | |
| 652 | CH$_3$ | CH$_3$ | 6-CH$_3$ |  | H | H |  | |
| 653 | CH$_3$ | CH$_3$ | 6-CH$_3$ | 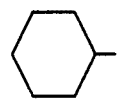 | H | H |  | |
| 654 | CH$_3$ | CH$_3$ | 6-CH$_3$ |  | CH$_3$— | H | CH$_3$— | |
| 655 | CH$_3$ | CH$_3$ | 6-CH$_3$ |  | CH$_3$— | H | C$_2$H$_5$— | |
| 656 | CH$_3$ | CH$_3$ | 6-CH$_3$ |  | CH$_3$— | H | (CH$_3$)$_2$CH— | |

TABLE 3-continued (Ic)

| Ex. No. | X | Y | $Z_n$ | A | B | C* | $R^1$ | mp °C. |
|---|---|---|---|---|---|---|---|---|
| 657 | CH$_3$ | CH$_3$ | 6-CH$_3$ |  | CH$_3$— | H | (CH$_3$)$_2$CH—CH$_2$— | |
| 658 | CH$_3$ | CH$_3$ | 6-CH$_3$ | 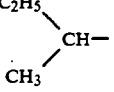 | CH$_3$— | H | C$_2$H$_5$\\CH—/CH$_3$ | |
| 659 | CH$_3$ | CH$_3$ | 6-CH$_3$ |  | CH$_3$— | H | (CH$_3$)$_3$C—CH$_2$— | |
| 660 | CH$_3$ | CH$_3$ | 6-CH$_3$ |  | CH$_3$— | H | 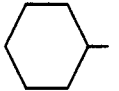 | |
| 661 | CH$_3$ | CH$_3$ | 6-CH$_3$ |  | CH$_3$— | H | 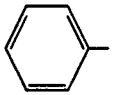 | |
| 662 | CH$_3$ | CH$_3$ | 6-CH$_3$ |  | C$_2$H$_5$— | H | CH$_3$— | |
| 663 | CH$_3$ | CH$_3$ | 6-CH$_3$ |  | C$_2$H$_5$— | H | C$_2$H$_5$— | |
| 664 | CH$_3$ | CH$_3$ | 6-CH$_3$ |  | C$_2$H$_5$— | H | (CH$_3$)$_2$CH— | |
| 665 | CH$_3$ | CH$_3$ | 6-CH$_3$ |  | C$_2$H$_5$— | H | (CH$_3$)$_2$CH—CH$_2$— | |
| 666 | CH$_3$ | CH$_3$ | 6-CH$_3$ |  | C$_2$H$_5$— | H | C$_2$H$_5$\\CH—/CH$_3$ | oil |
| 667 | CH$_3$ | CH$_3$ | 6-CH$_3$ | 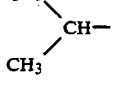 | C$_2$H$_5$— | H | (CH$_3$)$_3$C—CH$_2$— | |
| 668 | CH$_3$ | CH$_3$ | 6-CH$_3$ |  | C$_2$H$_5$— | H |  | |
| 669 | CH$_3$ | CH$_3$ | 6-CH$_3$ | 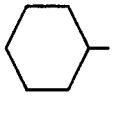 | C$_2$H$_5$— | H |  | |
| 670 | CH$_3$ | CH$_3$ | 6-CH$_3$ | 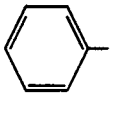 | C$_3$H$_7$— | H | C$_2$H$_5$— | |

TABLE 3-continued (Ic)

| Ex. No. | X | Y | $Z_n$ | A | B | C* | $R^1$ | mp °C. |
|---|---|---|---|---|---|---|---|---|
| 671 | CH₃ | CH₃ | 6-CH₃ |  | C₃H₇— | H | (CH₃)₂CH— | |
| 672 | CH₃ | CH₃ | 6-CH₃ |  | C₃H₇— | H | (CH₃)₂CH—CH₂— | |
| 673 | CH₃ | CH₃ | 6-CH₃ |  | C₃H₇— | H | CH₃<br>\<br>CH—<br>/<br>C₂H₅ | |
| 674 | CH₃ | CH₃ | 6-CH₃ | 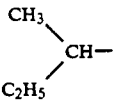 | C₃H₇— | H | (CH₃)₃C—CH₂— | |
| 675 | CH₃ | CH₃ | 6-CH₃ |  | (CH₃)₂CH— | H | C₂H₅— | |
| 676 | CH₃ | CH₃ | 6-CH₃ |  | (CH₃)₂CH— | H | (CH₃)₂CH— | |
| 677 | CH₃ | CH₃ | 6-CH₃ |  | (CH₃)₂CH— | H | (CH₃)₂CH—CH₂— | |
| 678 | CH₃ | CH₃ | 6-CH₃ |  | (CH₃)₂CH— | H | CH₃<br>\<br>CH—<br>/<br>C₂H₅ | |
| 679 | CH₃ | CH₃ | 6-CH₃ |  | (CH₃)₂CH— | H | (CH₃)₃C—CH₂— | |
| 680 | CH₃ | CH₃ | 6-CH₃ | 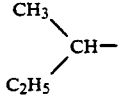 | H | H | CH₃— | 70 |
| 681 | CH₃ | CH₃ | 6-CH₃ |  | H | H | C₂H₅— | 56 |
| 682 | CH₃ | CH₃ | 6-CH₃ | 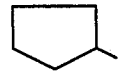 | H | H | (CH₃)₂CH— | 84 |
| 683 | CH₃ | CH₃ | 6-CH₃ | 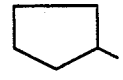 | H | H | (CH₃)₂CH—CH₂— | 69 |
| 684 | CH₃ | CH₃ | 6-CH₃ | 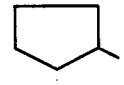 | H | H | C₂H₅<br>\<br>CH—<br>/<br>CH₃ | 64 |
| 685 | CH₃ | CH₃ | 6-CH₃ | 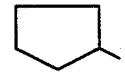 | H | H | (CH₃)₃C—CH₂— | 114 |

TABLE 3-continued

(Ic)

| Ex. No. | X | Y | $Z_n$ | A | B | C* | $R^1$ | mp °C. |
|---|---|---|---|---|---|---|---|---|
| 686 | $CH_3$ | $CH_3$ | 6-$CH_3$ | cyclopentyl | H | H | cyclohexyl | |
| 687 | $CH_3$ | $CH_3$ | 6-$CH_3$ | cyclopentyl | H | H | phenyl | |
| 688 | $CH_3$ | $CH_3$ | 6-$CH_3$ | cyclopentyl | $CH_3-$ | H | $CH_3-$ | |
| 689 | $CH_3$ | $CH_3$ | 6-$CH_3$ | cyclopentyl | $CH_3-$ | H | $C_2H_5-$ | |
| 690 | $CH_3$ | $CH_3$ | 6-$CH_3$ | cyclopentyl | $CH_3$ | H | $(CH_3)_2CH-$ | |
| 691 | $CH_3$ | $CH_3$ | 6-$CH_3$ | cyclopentyl | $CH_3-$ | H | $(CH_3)_2CH-CH_2-$ | |
| 692 | $CH_3$ | $CH_3$ | 6-$CH_3$ | cyclopentyl | $CH_3-$ | H | $\begin{array}{c}C_2H_5\\ \phantom{C_2H_5}CH-\\ CH_3\end{array}$ | |
| 693 | $CH_3$ | $CH_3$ | 6-$CH_3$ | cyclopentyl | $CH_3-$ | H | $(CH_3)_3C-CH_2-$ | |
| 694 | $CH_3$ | $CH_3$ | 6-$CH_3$ | cyclopentyl | $CH_3-$ | H | cyclohexyl | |
| 695 | $CH_3$ | $CH_3$ | 6-$CH_3$ | cyclopentyl | $CH_3-$ | H | phenyl | |
| 696 | $CH_3$ | $CH_3$ | 6-$CH_3$ | cyclopentyl | $C_2H_5-$ | H | $CH_3-$ | |
| 697 | $CH_3$ | $CH_3$ | 6-$CH_3$ | cyclopentyl | $C_2H_5-$ | H | $C_2H_5-$ | |

TABLE 3-continued (Ic)

| Ex. No. | X | Y | $Z_n$ | A | B | C* | $R^1$ | mp °C. |
|---|---|---|---|---|---|---|---|---|
| 698 | $CH_3$ | $CH_3$ | 6-$CH_3$ |  | $C_2H_5$— | H | $(CH_3)_2CH$— | |
| 699 | $CH_3$ | $CH_3$ | 6-$CH_3$ | 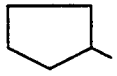 | $C_2H_5$ | H | $(CH_3)_2CH-CH_2$— | |
| 700 | $CH_3$ | $CH_3$ | 6-$CH_3$ |  | $C_2H_5$— | H | $\begin{array}{c}C_2H_5\\|\\CH-\\|\\CH_3\end{array}$ | |
| 701 | $CH_3$ | $CH_3$ | 6-$CH_3$ |  | $C_2H_5$— | H | $(CH_3)_3C-CH_2$— | |
| 702 | $CH_3$ | $CH_3$ | 6-$CH_3$ | 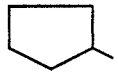 | $C_2H_5$— | H |  | |
| 703 | $CH_3$ | $CH_3$ | 6-$CH_3$ |  | $C_2H_5$— | H |  | |
| 704 | $CH_3$ | $CH_3$ | 6-$CH_3$ | 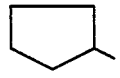 | $C_3H_7$— | H | $C_2H_5$— | |
| 705 | $CH_3$ | $CH_3$ | 6-$CH_3$ | 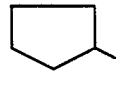 | $C_3H_7$— | H | $(CH_3)_2CH$— | |
| 706 | $CH_3$ | $CH_3$ | 6-$CH_3$ | 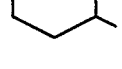 | $C_3H_7$— | H | $(CH_3)_2CH-CH_2$— | |
| 707 | $CH_3$ | $CH_3$ | 6-$CH_3$ |  | $C_3H_7$— | H | $\begin{array}{c}CH_3\\|\\CH-\\|\\C_2H_5\end{array}$ | |
| 708 | $CH_3$ | $CH_3$ | 6-$CH_3$ |  | $C_3H_7$— | H | $(CH_3)_3C-CH_2$— | |
| 709 | $CH_3$ | $CH_3$ | 6-$CH_3$ | 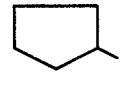 | $(CH_3)_2CH$— | H | $C2H_5$— | |
| 710 | $CH_3$ | $CH_3$ | 6-$CH_3$ |  | $(CH_3)_2CH$— | H | $(CH_3)_2CH$— | |

TABLE 3-continued (Ic)

| Ex. No. | X | Y | $Z_n$ | A | B | C* | $R^1$ | mp °C. |
|---|---|---|---|---|---|---|---|---|
| 711 | CH₃ | CH₃ | 6-CH₃ | cyclopentyl | (CH₃)₂CH— | H | (CH₃)₂CH—CH₂— | |
| 712 | CH₃ | CH₃ | 6-CH₃ | cyclopentyl | (CH₃)₂CH— | H | CH₃\\CH— /C₂H₅ | |
| 713 | CH₃ | CH₃ | 6-CH₃ | cyclopentyl | (CH₃)₂CH— | H | (CH₃)₃C—CH₂— | |
| 714 | CH₃ | CH₃ | 6-CH₃ | cyclohexyl | H | H | CH₃— | |
| 715 | CH₃ | CH₃ | 6-CH₃ | cyclohexyl | H | H | C₂H₅— | |
| 716 | CH₃ | CH₃ | 6-CH₃ | cyclohexyl | H | H | (CH₃)₂CH— | |
| 717 | CH₃ | CH₃ | 6-CH₃ | cyclohexyl | H | H | (CH₃)₂CH—CH₂— | |
| 718 | CH₃ | CH₃ | 6-CH₃ | cyclohexyl | H | H | C₂H₅\\CH— /CH₃ | |
| 719 | CH₃ | CH₃ | 6-CH₃ | cyclohexyl | H | H | (CH₃)₃C—CH₂— | |
| 720 | CH₃ | CH₃ | 6-CH₃ | cyclohexyl | H | H | cyclohexyl | |
| 721 | CH₃ | CH₃ | 6-CH₃ | cyclohexyl | H | H | phenyl | |
| 722 | CH₃ | CH₃ | 6-CH₃ | cyclohexyl | CH₃— | H | CH₃— | |

TABLE 3-continued (Ic)

$$R^2O-\overset{O}{\underset{\|}{C}}-O$$ structure with B, C*, A-N, X, Y, Z_n substituents

| Ex. No. | X | Y | $Z_n$ | A | B | C* | $R^1$ | mp °C. |
|---|---|---|---|---|---|---|---|---|
| 723 | CH₃ | CH₃ | 6-CH₃ | 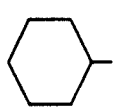 | CH₃— | H | C₂H₅— | |
| 724 | CH₃ | CH₃ | 6-CH₃ | 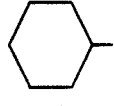 | CH₃— | H | (CH₃)₂CH— | |
| 725 | CH₃ | CH₃ | 6-CH₃ | 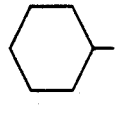 | CH₃— | H | (CH₃)₂CH—CH₂— | |
| 726 | CH₃ | CH₃ | 6-CH₃ | 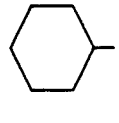 | CH₃— | H | C₂H₅\CH—  /  CH₃ | |
| 727 | CH₃ | CH₃ | 6-CH₃ | 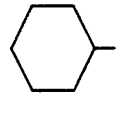 | CH₃— | H | (CH₃)₃C—CH₂— | |
| 728 | CH₃ | CH₃ | 6-CH₃ | 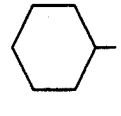 | CH₃— | H | 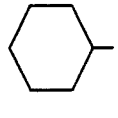 | |
| 729 | CH₃ | CH₃ | 6-CH₃ | 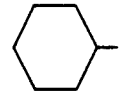 | CH₃— | H | 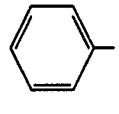 | |
| 730 | CH₃ | CH₃ | 6-CH₃ | 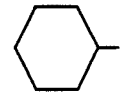 | C₂H₅— | H | CH₃— | |
| 731 | CH₃ | CH₃ | 6-CH₃ | 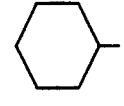 | C₂H₅— | H | C₂H₅— | |
| 732 | CH₃ | CH₃ | 6-CH₃ | 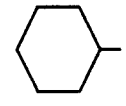 | C₂H₅— | H | (CH₃)₂CH— | |
| 733 | CH₃ | CH₃ | 6-CH₃ | 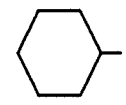 | C₂H₅— | H | (CH₃)₂CH—CH₂— | |

TABLE 3-continued
(Ic)
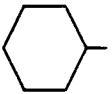
| Ex. No. | X | Y | $Z_n$ | A | B | C* | $R^1$ | mp °C. |
|---|---|---|---|---|---|---|---|---|
| 734 | CH₃ | CH₃ | 6-CH₃ | 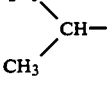 | C₂H₅— | H | C₂H₅\CH—/CH₃ | |
| 735 | CH₃ | CH₃ | 6-CH₃ |  | C₂H₅— | H | (CH₃)₃C—CH₂— | |
| 736 | CH₃ | CH₃ | 6-CH₃ | 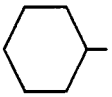 | C₂H₅— | H | 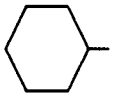 | |
| 737 | CH₃ | CH₃ | 6-CH₃ | 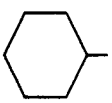 | C₂H₅— | H | 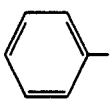 | |
| 738 | CH₃ | CH₃ | 6-CH₃ | 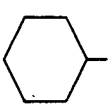 | C₃H₇— | H | C₂H₅— | |
| 739 | CH₃ | CH₃ | 6-CH₃ | 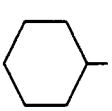 | C₃H₇— | H | (CH₃)₂CH— | |
| 740 | CH₃ | CH₃ | 6-CH₃ | 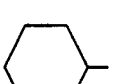 | C₃H₇— | H | (CH₃)₂CH—CH₂ | |
| 741 | CH₃ | CH₃ | 6-CH₃ | 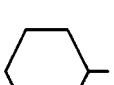 | C₃H₇— | H | CH₃\CH—/C₂H₅ | |
| 742 | CH₃ | CH₃ | 6-CH₃ | 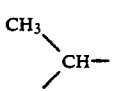 | C₃H₇— | H | (CH₃)₃C—CH₂— | |
| 743 | CH₃ | CH₃ | 6-CH₃ | 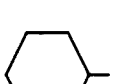 | (CH₃)₂CH— | H | C₂H₅— | |
| 744 | CH₃ | CH₃ | 6-CH₃ | 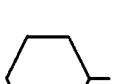 | (CH₃)₂CH— | H | (CH₃)₂CH— | |

TABLE 3-continued (Ic)

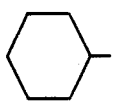

| Ex. No. | X | Y | $Z_n$ | A | B | C* | $R^1$ | mp °C. |
|---|---|---|---|---|---|---|---|---|
| 745 | $CH_3$ | $CH_3$ | 6-$CH_3$ | 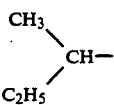 | $(CH_3)_2CH-$ | H | $(CH_3)_2CH-CH_2$ | |
| 746 | $CH_3$ | $CH_3$ | 6-$CH_3$ | 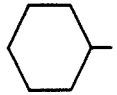 | $(CH_3)_2CH-$ | H | $\begin{array}{c}CH_3\\ \diagdown\\ CH-\\ \diagup\\ C_2H_5\end{array}$ | |
| 747 | $CH_3$ | $CH_3$ | 6-$CH_3$ |  | $(CH_3)_2CH-$ | H | $(CH_3)_3C-CH_2-$ | |
| 748 | $CH_3$ | $CH_3$ | 6-$CH_3$ | $CH_3-O-(CH_2)_2-$ | H | H | $C_2H_5-$ | |
| 749 | $CH_3$ | $CH_3$ | 6-$CH_3$ | $CH_3-O-(CH_2)_2-$ | H | H | $(CH_3)_2CH-$ | |
| 750 | $CH_3$ | $CH_3$ | 6-$CH_3$ | $CH_3-O-(CH_2)_3-$ | H | H | $(CH_3)_2CH-CH_2$ | |
| 751 | $CH_3$ | $CH_3$ | 6-$CH_3$ | $CH_3-O-(CH_2)_2-$ | H | H | $\begin{array}{c}CH_3\\ \diagdown\\ CH-\\ \diagup\\ C_2H_5\end{array}$ | |
| 752 | $CH_3$ | $CH_3$ | 6-$CH_3$ | $CH_3-O-(CH_2)_2-$ | H | H | $(CH_3)_3C-CH_2-$ | |
| 753 | $CH_3$ | $CH_3$ | 6-$CH_3$ | $CH_3-O-(CH_2)_2-$ | $CH_3-$ | H | $C_2H_5-$ | |
| 754 | $CH_3$ | $CH_3$ | 6-$CH_3$ | $CH_3-O-(CH_2)_2-$ | $CH_3-$ | H | $(CH_3)_2CH-$ | |
| 755 | $CH_3$ | $CH_3$ | 6-$CH_3$ | $CH_3-O-(CH_2)_2-$ | $CH_3-$ | H | $(CH_3)_2CH-CH_2-$ | 57 |
| 756 | $CH_3$ | $CH_3$ | 6-$CH_3$ | $CH_3-O-(CH_2)_2-$ | $CH_3-$ | H | $\begin{array}{c}CH_3\\ \diagdown\\ CH-\\ \diagup\\ C_2H_5\end{array}$ | 54 |
| 757 | $CH_3$ | $CH_3$ | 6-$CH_3$ | $CH_3-O-(CH_2)_2-$ | $CH_3-$ | H | $(CH_3)_3C-CH_2-$ | |
| 758 | $CH_3$ | $CH_3$ | 6-$CH_3$ | $CH_3-O-CH_2-CH(CH_3)-$ | H | H | $C_2H_5-$ | 60 |
| 759 | $CH_3$ | $CH_3$ | 6-$CH_3$ | $CH_3-O-CH_2-CH(CH_3)-$ | H | H | $(CH_3)_2CH-$ | |
| 760 | $CH_3$ | $CH_3$ | 6-$CH_3$ | $CH_3-O-CH_2-CH(CH_3)-$ | H | H | $(CH_3)_2CH-CH_2-$ | |
| 761 | $CH_3$ | $CH_3$ | 6-$CH_3$ | $CH_3-O-CH_2-CH(CH_3)-$ | H | H | $\begin{array}{c}CH_3\\ \diagdown\\ CH-\\ \diagup\\ C_2H_5\end{array}$ | |
| 762 | $CH_3$ | $CH_3$ | 6-$CH_3$ | $CH_3-O-CH_2-CH(CH_3)-$ | H | H | $(CH_3)_3C-CH_2-$ | |
| 763 | $CH_3$ | $CH_3$ | 6-$CH_3$ | $CH_3-O-CH_2-CH(CH_3)-$ | $CH_3-$ | H | $C_2H_5-$ | |
| 764 | $CH_3$ | $CH_3$ | 6-$CH_3$ | $CH_3-O-CH_2-CH(CH_3)-$ | $CH_3-$ | H | $(CH_3)_2CH-$ | |
| 765 | $CH_3$ | $CH_3$ | 6-$CH_3$ | $CH_3-O-CH_2-CH(CH_3)-$ | $CH_3-$ | H | $(CH_3)_2CH-CH_2-$ | |
| 766 | $CH_3$ | $CH_3$ | 6-$CH_3$ | $CH_3-O-CH_2-CH(CH_3)-$ | $CH_3-$ | H | $\begin{array}{c}CH_3\\ \diagdown\\ CH-\\ \diagup\\ C_2H_5\end{array}$ | |

TABLE 3-continued

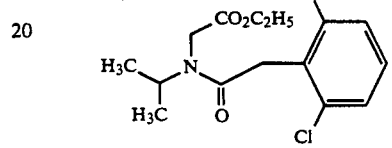

(Ic)

| Ex. No. | X | Y | $Z_n$ | A | B | C* | $R^1$ | mp °C. |
|---|---|---|---|---|---|---|---|---|
| 767 | $CH_3$ | $CH_3$ | 6-$CH_3$ | $CH_3$—O—$CH_2$—CH($CH_3$)— | $CH_3$— | H | $(CH_3)_3C$—$CH_2$— | |

Preparation of the intermediates

EXAMPLE I

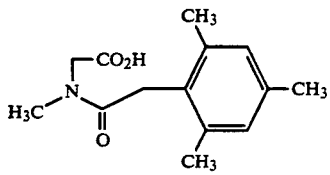

11.25 g (0.15 mol) of sarcosine and 3 g (0.075 mol) of NaOH are dissolved in 210 ml of water. While cooking the solution in a water bath 9 g (0.225 mol) of NaOH, dissolved in 45 ml of water, and 29.6 g (0.15 mol) of mesityleneacetyl chloride are added synchronously dropwise, during which addition the temperature is kept at <40 ° C. After 1 hour the mixture is acidified with concentrated HCl at 0° to 20° C., filtered off and the filtrate is dried in vacuo over $P_2O_5$ at 70° C. 37.1 g (99.3 % of theory) of N-(2,4,6-trimethyl-phenyl-acetyl)-sarcosine of a melting point of 140° C. are obtained.

EXAMPLE II

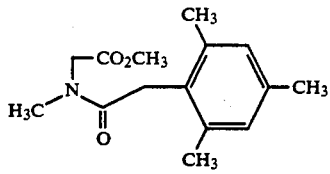

37.1 g (0.149 mol) of N-(2,4,6-trimethyl-phenyl-acetyl)-sarcosine are suspended in 150 ml of methanol, 22 ml (0.165 mol) of dimethoxypropane are added and, after adding 1,43 g (7 5 mmol) of p-toluenesulphonic acid monohydrate,the mixture is refluxed for 3 hours.

After evaporating off the solvent, the residue is taken up in $CH_2Cl_2$, washed with bicarbonate solution, dried and evaporated on a rotary evaporator. 34 g (about 86.7% of theory) of N-(2,4)6-trimethylphenyl-acetyl)-sarcosine methyl ester are obtained in the form of a pale yellow oil.

$^1$H-NMR(200 MHz, $CDCl_3$): δ=2.18, 2 2, 2 28 (s, 9H Ar-$CH_3$); 3.0, 3.2 (s, 3H, N$CH_3$), 3.64, 3.67 (s, 2H, $CH_2$-Ar), 3.66, 3.69 (s, 3H, O$CH_3$), 3.79, 4.14 (s, 2H, N-$CH_2$-CO), 6.82 (s, 2H, Ar 3-H, 5-H)

EXAMPLE III 17.4 g (0.12 mol) of N-isopropylglycine ethyl ester are dissolved in 180 ml of absolute THF and 16.8 ml (0.12 mol) of triethylamine are added. 26.82 g (0.12 mol) of 2,6-dichlorophenylacetyl chloride in 20 ml of absolute THF are added dropwise at 0°-10° C. After 1 hour the mixture is stirred into 1 l of ice water +100 ml of 1 N/HCl,the product is extracted with $CH_2Cl_2$ and the organic phase is dried and concentrated by evaporation. 36.8 g (89.1% of theory) of a yellow oil are obtained.

$^1$H-NMR(200 MHz, $CDCl_3$): δ=1.11-1.32 (m, 9H $CH_2$-$CH_3$ CH($CH_3$)$_2$), 7.08-7.15 (1H, m, Ar 4-H), 7.25-7.32 (m, 2H, Ar-3-H, 5-H).

Crystallization from ether/n-hexane gives 3.8 g (80.4% of theory) of 4-(pivaloyloxy)-3-(2,4,6-trimethyl-phenyl)-1-methyl-3-pyrrolin-2-one of melting point 75° C.

The active compounds are suitable for combating animal pests, preferably arthropods and nematodes, in particular insects and arachnida encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus* corporis, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdecus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Acanthoscelides obtectus, Hylotrupes bajulus Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus, hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus, Latrodectus mactans.*

From the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphenema spp. and Trichodorus spp..

The active compounds according to the invention can furthermore be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

It is characteristic of the compounds according to the invention that they have a selective effect against monocotyledon weeds when used in the pre-and postemergence method, combined with a good tolerance by crop plants.

The active compounds according to the invention can be used, for example, in connection with the following plants:

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Here, the compounds according to the invention show a good tolerance by important crop plants, such as, for example, wheat, cotton, soy beans, citrus fruit and sugar beets, besides having an excellent action against harmful plants, and they can therefore be employed as selective weedkillers.

The active compounds can be converted into the customary formulations, such as solutions, emulsions, suspensions, powders, foams, pastes, granules, aerosols, natural and synthetic materials impregnated with active compound, and very fine capsules in polymeric substances and in coating compositions for seeds, furthermore in formulations using burning equipment such as fumigating cartridges, cans, coils,etc., and in ULV cold mist and warm mist formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; liquefied gaseous extenders or carriers are those liquids which are gaseous at normal temperature and under atmospheric pressure, for example aerosol propellant, such as halogenohydrocarbons as well as butane, propane, nitrogen or carbon dioxide. As solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphcnates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, herbicides or fungicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds which can be used according to the invention are also suitable for combating midges, ticks,etc.,in the sectors of animal keeping and cattle breeding; better results, for example higher milk production, greater weight, more attractive animal pelt, longer life,etc., can be achieved by combating the pests.

The application of the active compounds which can be used according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as molded articles (collar, ear tag) is also possible.

EXAMPLE A

Nephotettix test

Solvent: 7 parts by weight of dimethyl formamide
Emulsifier: 1 part by weight of alkylaryl polyglycol ether To produce a suitable preparation of active compound, I part by weight of active compound is mixed with the stated amount of solvent and the stated amount of emulsifier, and the concentrate is diluted to the desired concentration with water.

Rice seedlings (oryza sativa) are treated by being dipped into the preparation of active compound at the desired concentration, and larvae of the green rice leaf hopper (*Nephotettix cincticeps*) are placed on the seedlings while they are still wet.

After the desired time, destruction is determined in %. 100% denotes here that all the leaf hoppers have been destroyed; 0% denotes that none of the leaf hoppers have been destroyed.

In this test, for example the following compounds of the Preparation Examples show a superior activity compared with the prior art: (5), (54), (55), (56), (57), (58).

The compounds of the formula (I) according to the invention show antimicrobial, and particularly powerful antibacterial and antimycotic, actions. They have a very broad range of antimycotic actions, in particular against dermatophytes and yeasts, as well as biphasic fungi, for example against Candida species, such as *Candida albicans,* Epidermophyton species, such as *Epidermophyton floccosum,* Aspergillus species, such as *Aspergillus niger* and *Aspergillus fumigatus,* Trichophyton species, such as *Trichophyton mentagrophytes,* Microsporon species, such as *Microsporon felineum,* as well as Torulopsis species, such as *Torulopsis glabrata.* This list of microorganisms in no way intends to limit the germs which can be combated, but only serves for illustration.

Examples of indication in human medicine which may be mentioned are: Dermatomycoses and systemic mycoses caused by *Trichophyton mentagrophytes* and other Trichophyton species, Microsporon species as well as *Epidermophyton floccosum,* yeasts and biphasic fungi, as well as molds.

The following may be mentioned as examples of a field of indication in veterinary medicine:

All dermatomycoses and systemic mycoses, in particular those caused by the abovementioned pathogens.

The present invention includes pharmaceutical preparations which, besides non-toxic, inert pharmaceutically suitable excipients, contain one or more active compounds according to the invention, or which consist of one or more active compounds according to the invention.

The present invention also includes pharmaceutical preparations in dosage units. This means that the preparations are in the form of individual parts, for example tablets, coated tablets, capsules, pills, suppositories and ampoules, whose active compound content corresponds to a fraction, or a multiple, of a single dose. The dosage units can contain, for example, 1, 2, 3 or 4 simple doses or ½, ⅓ or ¼ of a simple dose. A single dose preferably contains the amount of active compound which is administered during one application, and which usually corresponds to a whole, half, a third, or a quarter of a daily dose.

Non-toxic, inert pharmaceutically suitable excipients are taken to mean solid, semi-solid or liquid diluents, fillers or formulation auxiliaries of any type. Preferred pharmaceutical preparations which may be mentioned are tablets, coated tablets, capsules, pills, granules, suppositories, solutions, suspensions and emulsions, pastes, ointments, gels, creams, lotions, powders or sprays.

Tablets, coated tablets, capsules, pills and granules can contain the active compound(s) besides conventional excipients, such as (a) fillers and extenders, for example starches, lactose, sucrose, glucose, mannitol and silicic acid, (b) binders, for example carboxymethylcellulose, alginates, gelantine, polyvinyl pyrrolidone, (c) humectants, for example glycerol, (d) disintegrants, for example agar-agar, calcium carbonate and sodium bicarbonate, (e) solution retardants, for example paraffin and (f) resorption accelerators, for example quaternary ammonium compounds, (g) wetting agents, for example cetyl alcohol and glycerol monostearate, (h) adsorption agents, for example kaolin and bentonite and (i) lubricants, for example talc, calcium stearate and magnesium stearate and solid polyethylene glycols, or mixtures of the substances listed under (a) to (i).

The tablets, coated tablets, capsules, pills and granules may be provided with the conventional coatings and shells, optionally containing opacifying agents, and they can be composed in a manner such that they release the active compound(s) only, or preferably, in a specific part of the intestinal tract, if appropriate in a retarded manner, suitable embedding compositions which can be used being, for example, polymeric substances and waxes.

The active compound(s) can also be present in microencapsulated form, if appropriate together with one or more of the abovementioned excipients.

Suppositories can contain, besides the active compound(s), the conventional water-soluble or water-insoluble excipients, for example polyethylene glycols, fats, for example cocoa fat, and higher esters (for example $C_{14}$-alcohol with $C_{16}$-fatty acid), or mixtures of these substances.

Ointments, pastes, creams and gels can contain, besides the active compound(s), the conventional excipients, for example animal and vegetable fats, waxes, paraffins, starch, tragacanth, cellulose derivatives, polyethylene glycols, silicones, bentonites, silicic acid, talc and zinc oxide, or mixtures of these substances.

Powders and sprays can contain, besides the active compound(s), the conventional excipients, for example lactose, talc, silicic acid, aluminium hydroxide, calcium silicate and polyamide powder, or mixtures of these substances, and sprays can additionally contain the conventional propellants, for example chlorofluorohydrocarbons.

Solutions and emulsions can contain, besides the active compound(s), the conventional excipients, such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethyl formamide, oils, in particular cottonseed oil, groundnut oil, corn germ oil, olive oil, castor oil and sesame seed oil, glycerol, glycerol formal, tetrahydrofurfuryl alcohol, polyethylene glycols and fatty acid esters of sorbitan, or mixtures of these substances.

For parenteral application, the solutions and emulsions can also be in sterile form and a form isotonic which is with blood.

Suspensions can contain, besides the active compound(s), the conventional excipients, such as liquid diluents, for example water, ethyl alcohol, propyl alcohol, suspending agents, for example ethoxylated isostearyl alcohols, polyoxyethylene sorbitol ester and polyoxyethylene sorbitan ester, microcrystalline cellulose, aluminium metahydroxide, bentonite, agar-agar and tragacanth, or mixtures of these substances.

The formulation types mentioned can also contain colourants, preservatives and additives which improve the odour and flavour, for example peppermint oil and eucalylptus oil, and sweeteners, for example saccharin.

The therapeutically active compounds in the abovementioned pharmaceutical preparations should preferably be present in a concentration of about 0.1 to 99.5, preferably of 0.5 to 95%, by weight of the total mixture.

In addition to the active compounds according to the invention, the abovementioned pharmaceutical preparations can also contain other pharmaceutical active compounds.

The preparation of the abovementioned pharmaceutical preparations is carried out in a customary manner by known methods, for example by mixing the active compound(s) with the excipient(s).

The present invention also includes the use of the active compounds according to the invention, as well as the use of pharmaceutical preparations which contain one or more active compounds according to the invention, in human and veterinary medicine for the prevention, ease and/or cure of the abovementioned diseases.

The active substances or the pharmaceutical preparations can be administered locally, orally, parenterally, intraperitoneally and/or rectally, preferably parenterally, in particular intravenously.

In general, it has proven advantageous both in human and in veterinary medicine, to administer the active compound(s) according to the invention in total amounts of about 2.5 to about 200, preferably of 5 to 150, mg/kg of body weight every 24 hours, where appropriate in the form of several individual doses, in order to achieve the desired results.

In the case of oral administration, the active compounds according to the invention are administered in total amounts of about 2.5 to about 200, preferably of 5 to 150, mg/kg of body weight every 24 hours, and in the case of parenteral application in total amounts of about 2.5 to about 50, preferably from 1 to 25, mg/kg of body weight every 24 hours.

However, it may be necessary to deviate from the dosages mentioned, namely as a function of the species and the bodyweight of the object to be treated, the type and severity of the disease, the type of preparation and the way the medicament is administered, as well as of the period or interval within which the medicament is administered. Thus, in some cases it may suffice to use less than the abovementioned amount of active compound, while in other cases the abovementioned amount of active compound must be exceeded. The decision concerning the specific optimum dosage required and the way in which the active compounds are administered can easily be made by anyone skilled in the art on the basis of his expert knowledge.

EXAMPLE B

Antimycotic in-vitro activity

Experimental set-up:

The in-vitro tests were carried out using inocula of an average of $1 \times 10^4$ microorganisms/ml of substrate. The nutrient medium used was Yeast Nitrogen Base medium for yeasts and Kimmig medium for moulds and dermatophytes.

The incubation temperature was 37° C. in the case of yeasts and 28° C. in the case of moulds and dermatophytes, the incubation time was 24 to 96 hours in the case of yeasts and 96 to 120 hours in the case of dermatophytes and moulds.

The fungicides were assessed by plating and reincubation of fully inhibited batches, fungicidal concentrations being those containing fewer than 100 microorganisms c.f.n. (colony-forming unit) per ml.

In this test, the compounds of the formula (I) according to the invention of Preparation Examples 45, 46, 47 showed a highly pronounced antimycotic activity.

It is understood that the specification and examples are illustrative but not limitative of the present invention and that other embodiments within the spirit and scope of the invention will suggest themselves to those skilled in the art. In the following claims, substituent "C*" is expressed as D.

We claim:

1. A method combating unwanted vegetation which comprises applying thereto or to a locus from which it is desired to exclude such vegetation, a herbicidally effective amount of a 3-aryl-pyrrolidine-2,4-dione of the formula

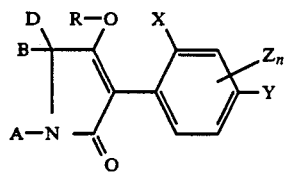

in which

X represents $C_1-C_6$-alkyl, halogen or $C_1-C_6$-alkoxy,

Y represents hydrogen, $C_1-C_6$-alkyl, halogen, $C_1-C_6$-alkoxy or $(C_1-C_3)$-halogenoalkyl, Z represents $C_1-C_6$-alkyl, halogen or $C_1-C_6$-alkoxy, n represents a number from 0–3, R represents hydrogen (Ia) or represents the groups of the formula —CO—$R^1$ or —CO—O—$R^2$, in which $R^1$ represents $C_1-C_{20}$-alkyl, $C_2-C_{20}$-alkenyl, $C_1-C_8$-alkoxy-$C_2-C_8$-alkyl, $C_1-C_8$-alkylthio-$C_2-C_8$-alkyl, $C_1-C_8$-polyalkoxy-$C_2-C_8$-alkyl or cycloalkyl which has 3–8 ring atoms and which can be interrupted by oxygen and/or sulphur, each of which radicals is optionally substituted by halogen, or represents phenyl which is optionally substituted by halogen, or represents phenyl which is optionally substituted by halogen, nitro, $C_1-C_6$-alkyl, $C_1-C_6$-alkoxy, $C_1-C_6$-halogenoalkyl or $C_1-C_6$-halogenoalkoxy, or represents phenyl-$C_1-C_6$-alkyl which is optionally substituted by halogen, $C_1-C_6$-alkyl, $C_1-C_6$-alkoxy, $C_1-C_6$-halogenoalkyl or $C_1-C_6$-halogenoalkoxy, $R^2$ represents $C_1-C_{20}$-alkyl, $C_2-C_{20}$-alkenyl, $C_1-C_8$-alkoxy-$C_2-C_8$-alkyl or $C_1-C_8$-polyalkoxy-$C_2-C_8$-alkyl, each of which radicals is optionally substituted by halogen, or represents phenyl or cycloalkyl which has 3–8 ring atoms, each of which radicals is optionally substituted by halogen, nitro, $C_1-C_6$-alkyl, $C_1-C_6$-alkoxy or $C_1-C_6$-halogenoalkyl, A represents straight-chain or branched $C_1-C_{12}$-alkyl, $C_3-C_8$-alkenyl, $C_3-C_8$-alkinyl, $C_1-C_{10}$-alkoxy-$C_2-C_8$-alkyl, $C_1-C_8$-polyalkoxy-$C_2-C_8$-alkyl, $C_1-C_{10}$-alkylthio-$C_2-C_8$-alkyl or cycloalkyl which has 3–8 ring atoms and which can be interrupted by oxygen and/or sulphur, each of which radicals is optionally substituted by halogen, or represents aryl-$C_1-C_6$-alkyl which is optionally substituted by halogen, $C_1-C_6$-alkyl-$C_1-C_6$-haloalkyl, $C_1-C_6$-alkoxy or nitro, and B and D independently of one another represent hydrogen, straight-chain or branched $C_1-C_{12}$-alkyl or $C_1-C_8$-alkoxyalkyl.

2. A method according to claim 1, in which

X represents $C_1-C_4$-alkyl, halogen or $C_1-C_4$-alkoxy,

Y represents hydrogen, $C_1-C_6$-alkyl, halogen, $C_1-C_4$-alkoxy or $C_1-C_2$-halogenoalkyl, Z represents $C_1-C_4$-alkyl, halogen or $C_1-C_4$-alkoxy, n represents a number from 0–3

R represents hydrogen or represents the groups of the formula

—CO—$R^1$ or —CO—O—$R^2$, in which $R^1$ represents $C_1-C_{16}$-alkyl, $C_2-C_{16}$-alkenyl, $C_1-C_6$-alkoxy-$C_2-C_6$-alkyl, $C_1-C_6$-alkylthio-$C_2-C_6$-alkyl, $C_1-C_6$-polyalkoxy-$C_2-C_6$-alkyl or cycloalkyl which has 3–7 ring atoms and which can be interrupted by 1–2 oxygen and/or sulphur atoms, each of which radicals is optionally substituted by halogen, or represents phenyl which is optionally substituted by halogen, nitro, $C_1-C_4$-alkyl, $C_1-C_4$-alkoxy, $C_1-C_3$-halogenoalkyl or $C_1-C_3$-halogenoalkoxy, or represents phenyl-$C_1-C_4$-alkyl which is optionally substituted by halogen, $C_1-C_4$-alkyl, $C_1-C_4$-alkoxy, $C_1-C_3$-halogenoalkyl or $C_1-C_3$-halogenoalkoxy, or represents hetaryl which is optionally substituted by halogen or $C_1-C_6$-alkyl, or represents phenoxy- $C_1-C_5$-alkyl which is optionally substituted by halogen or $C_1-C_4$-alkyl, $R^2$ represents $C_1-C_{16}$-alkyl, $C_2-C_{16}$-alkenyl, $C_1-C_{16}$-alkoxy-$C_2-C_6$-alkyl or $C_1-C_6$-polyalkoxy-$C_2-C_6$-alkyl, each of which radicals is optionally substituted by halogen or represents phenyl or cycloalkyl which has 3-7 ring atoms, each of which radicals is optionally substituted by halogen, nitro, $C_1-C_4$-alkyl, $C_1-C_3$-alkoxy or $C_1-C_3$-halogenoalkyl, A represents straight-chain or branched $C_1-C_{10}$-alkyl, $C_3-C_6$-alkenyl, $C_3-C_6$-alkinyl, $C_1-C_6$-alkoxy-$C_2-C_6$-alkyl, $C_1-C_6$-polyalkoxy-$C_2-C_6$-alkyl, $C_1-C_8$-alkylthio-$C_2-C_6$-alkyl or cycloalkyl which has 3-7 ring atoms and which can be interrupted by 1-2 oxygen and/or sulphur atoms, each of which radicals is optionally substituted by halogen, or represents aryl-$C_1-C_4$-alkyl which is optionally substituted by halogen, $C_1-C_4$-alkyl, $C_1-C_4$-halogenoalkyl-$C_1-C_4$-alkoxy or nitro, and B and C* independently of one another represent hydrogen, straight-chain or branched $C_1-C_{10}$-alkyl or $C_1-C_6$-alkoxyalkyl.

3. A method according to claim 1, in which

X represents methyl, ethyl, propyl, i-propyl, fluorine, chlorine, bromine, methoxy or ethoxy, Y represents hydrogen, methyl, ethyl, propyl, i-propyl, butyl, i-butyl, tert.-butyl, fluorine, chlorine, bromine, methoxy, ethoxy or trifluoromethyl, Z represents methyl, ethyl, i-propyl, butyl, i-butyl, tert.-butyl, fluorine, chlorine, bromine, methoxy or ethoxy, n represents a number from 0-3, R represents hydrogen or represents the groups of the formula —CO—$R^1$ or —CO—O—$R^2$, in which $R^1$ represents $C_1-C_{14}$-alkyl, $C_2-C_{14}$-alkenyl, $C_1-C_4$-alkoxy-$C_2-C_6$-alkyl, $C_1-C_4$-alkylthio-$C_2-C_6$-alkyl, $C_1-C_4$-polyalkoxyl-$C_2-C_4$-alkyl or cycloalkyl which has 3-6 ring atoms and which can be interrupted by 1-2 oxygen and/or sulphur atoms, each of which radicals is optionally substituted by fluorine or chlorine, or represents phenyl which is optionally substituted by fluorine, chlorine, bromine, methyl, ethyl, propyl, i-propyl, methoxy, ethoxy, trifluoromethyl, trifluoromethoxy or nitro, or represents phenyl-$C_1-C_3$-alkyl which is optionally substituted by fluorine, chlorine, bromine, methyl, ethyl, propyl, i-propyl, methoxy, ethoxy, trifluoromethyl or trifluoromethoxy, or represents phenoxy-$C_1-C_4$-alkyl which is optionally substituted by fluorine, chlorine, methyl or ethyl, $R^2$ represents $C_1-C_{14}$-alkyl, $C_2-C_{14}$-alkenyl, $C_1-C_4$-alkoxy-$C_2-C_6$-alkyl or $C_1-C_4$-polyalkoxy-$C_2-C_6$-alkyl, each of which radicals is optionally substituted by fluorine or chlorine, or represents phenyl or cycloalkyl which has 3-6 ring atoms, each of which radicals is optionally substituted by fluorine, chlorine, nitro, methyl, ethyl, propyl, i-propyl, methoxy, ethoxy or trifluoromethyl, A represents straight-chain or branched $C_1-C_8$-alkyl, $C_3-C_4$-alkenyl, $C_3-C_4$-alkinyl, $C_1-C_6$-alkoxy-$C_2-C_4$-alkyl, $C_1-C_4$-polyalkoxy-$C_2-C_4$-alkyl, $C_1-C_6$-alkylthio-$C_2-C_4$-alkyl or cycloalkyl which has 3-6 ring atoms and which can be interrupted by 1-2 oxygen and/or sulphur atoms, each of which radicals is optionally substituted by halogen, or represents aryl-$C_1-C_3$-alkyl which is optionally substituted by fluorine, chlorine, bromine, methyl, ethyl, propyl, isopropyl, methoxy, ethoxy, trifluoromethyl or nitro, and B and C* independently of one another represent hydrogen, straight-chain or branched $C_1-C_8$-alkyl and $C_1-C_4$-alkoxyalkyl.

4. A method according to claim 1, wherein such compound is 3-(2,6-dichlorophenyl)-1-methyl-pyrrolidine-2,4-dione of the formula

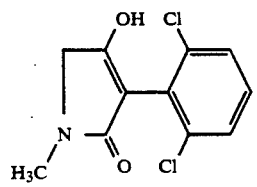

5. A method according to claim 1, wherein such compound is 3-(2,4,6-trimethylphenyl)-1-(1,2,2-trimethylpropyl)-pyrrolidine-2,4-dione of the formula

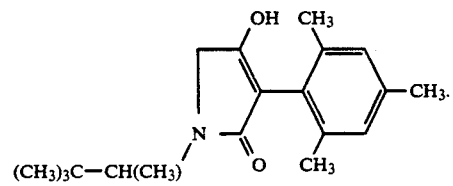

6. A method according to claim 1, wherein such compound is 3-(2,4,6-trimethylphenyl)-1-(1,1,3,3-tetramethyl-butyl)-pyrrolidine-2,4-dione of the formula

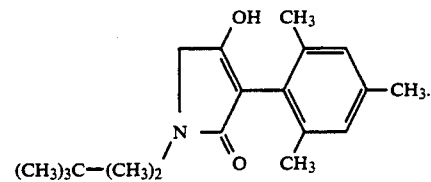

7. A method according to claim 1, wherein such compound is 3-(2,4,6-trimethylphenyl)-1-allyl-pyrrolidine-2,4-dione of the formula

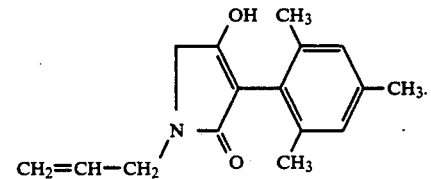

8. A method according to claim 1, wherein such compound is 3-(2,4,6-trimethylphenyl)-1-cyclopropyl-5,5-dimethyl-pyrollidine-2,4-dione of the formula

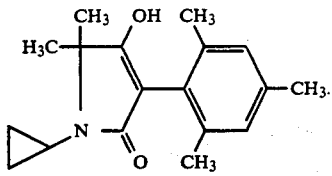

9. A method according to claim 1, wherein such compound is 3-(2,4,6-trimethylphenyl)-1-cyclopentyl-pyrrollidine-2,4-dione of the formula

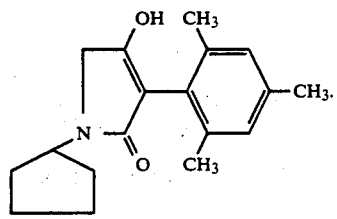

10. A method according to claim 1, wherein such compound is 3-(2,4,6-trimethylphenyl)-1-cyclopentyl-5-methyl-pyrrolidine-2,4-dione of the formula

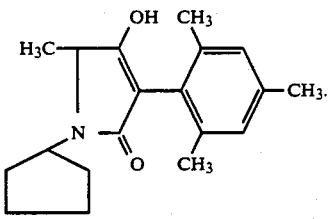

11. A method according to claim 1, wherein such compound is 3-(2,4,6-trimethylphenyl)-1-cyclopentyl-5-ethyl-pyrrolidine-2,4-dione of the formula

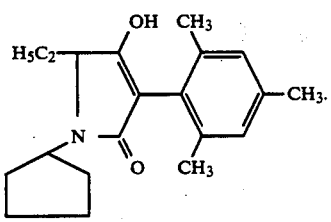

12. A method according to claim 1, wherein such compound is 3-(2,4,6-trimethylphenyl)-1-cyclopentyl-5-propyl-pyrrolidine-2,4-dione of the formula

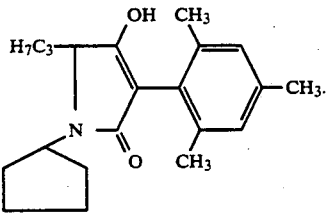

* * * * *

UNITED STATES PATENT AND TRADEMARK OFFICE
CERTIFICATE OF CORRECTION

PATENT NO.    : 5,186,737
DATED         : February 16, 1993
INVENTOR(S)   : Fischer, et al.

It is certified that error appears in the above-identified patent and that said Letters Patent is hereby corrected as shown below:

Title Page Item    [75] Inventors: 3rd Inventor delete
                   " Hageman " and substitute -- Hagemann --

Title Page         ABSTRACT: Line 31 delete " subsituted " and
                   substitute -- substituted --

Col. 96, line 47   After " 0-3 " insert -- , --

Col. 97, line 12   Delete " $C_1-C_6-$ " and substitute -- $C_1-C_8-$ --

Signed and Sealed this

Twenty-seventh Day of September, 1994

Attest:

BRUCE LEHMAN

Attesting Officer        Commissioner of Patents and Trademarks